United States Patent
Lin et al.

(10) Patent No.: US 11,913,043 B2
(45) Date of Patent: *Feb. 27, 2024

(54) CELL-TARGETED CYTOTOXIC CONSTRUCTS

(71) Applicant: Research Development Foundation, Carson City, NV (US)

(72) Inventors: Xinjian Lin, La Jolla, CA (US); Xiying Shang, La Jolla, CA (US); Stephen B. Howell, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 16 days.

This patent is subject to a terminal disclaimer.

(21) Appl. No.: 17/519,545

(22) Filed: Nov. 4, 2021

(65) Prior Publication Data

US 2022/0267752 A1 Aug. 25, 2022

Related U.S. Application Data

(63) Continuation of application No. 15/434,648, filed on Feb. 16, 2017, now Pat. No. 11,193,117.

(60) Provisional application No. 62/295,636, filed on Feb. 16, 2016.

(51) Int. Cl.

| | |
|---|---|
| C12N 9/64 | (2006.01) |
| C12N 9/52 | (2006.01) |
| A61K 47/68 | (2017.01) |
| A61K 47/65 | (2017.01) |
| C07K 14/435 | (2006.01) |
| C07K 14/59 | (2006.01) |
| C12N 9/96 | (2006.01) |
| A61K 48/00 | (2006.01) |

(52) U.S. Cl.
CPC ............ *C12N 9/6467* (2013.01); *A61K 47/65* (2017.08); *A61K 47/6889* (2017.08); *C07K 14/43504* (2013.01); *C07K 14/59* (2013.01); *C12N 9/52* (2013.01); *C12N 9/6424* (2013.01); *C12N 9/96* (2013.01); *C12Y 304/21079* (2013.01); *C12Y 304/2207* (2013.01); *C12Y 304/22007* (2013.01); *A61K 48/00* (2013.01); *C07K 2319/00* (2013.01); *C07K 2319/21* (2013.01); *C07K 2319/33* (2013.01); *C07K 2319/40* (2013.01); *C07K 2319/55* (2013.01); *C07K 2319/70* (2013.01); *C07K 2319/74* (2013.01); *C07K 2319/90* (2013.01)

(58) Field of Classification Search
None
See application file for complete search history.

(56) References Cited

U.S. PATENT DOCUMENTS

| | | | |
|---|---|---|---|
| 9,096,840 B2 | 8/2015 | Rosenblum et al. | |
| 11,193,117 B2 * | 12/2021 | Lin | A61K 47/65 |
| 11,370,827 B2 * | 6/2022 | Chhabra | A61P 7/04 |
| 2014/0140976 A1 | 5/2014 | Rosenblum et al. | |
| 2015/0010556 A1 | 1/2015 | Rosenblum et al. | |

FOREIGN PATENT DOCUMENTS

| | | |
|---|---|---|
| WO | WO 2010-087994 | 8/2010 |
| WO | WO 2011/133704 | 10/2011 |
| WO | WO 2014/088928 | 6/2014 |

OTHER PUBLICATIONS

Beerli et al. (Plos One, 10(7), 2015, pp. 1-17).*
Chen et al. (Genes and Development, vol. 27, pp. 1345-1350, 2013).*
Aulabaugh et al., "Development of an HPLC assay for *Staphylococcus aureus* sortase: evidence for the formation of the kinetically competent acyl enzyme intermediate," *Anal Biochem.*, 360:14-22, 2007.
Beerli et al., "Sortase enzyme-mediated generation of site-specifically conjugated antibody drug conjugates with high in vitro and in vivo potency," *Plos One*, 10(7):1-17, 2015.
Binnerts et al., "R-spondin1 regulates Wnt signaling by inhibiting internalization of LRP6," *PNAS*, 104(37):14700-14705, 2007.
Bradshaw et al., "Molecular features of the sortase enzyme family," *FEBS Journal*, 282:2097-2114, 2015.
Cao et al., "Design optimization and characterization of Her2/neu-targeted immunotoxins: comparative in vitro and in vivo efficacy studies," *Oncogene*, 33:429-39, 2014.
Carmon et al., "R-spondins function as ligands of the orphan receptors LGR4 and LGR5 to regulate Wnt/β-catenin signaling", *Proc Natl Acad Sci USA*, 108(28):11452-11457, 2011.
Chen et al., "The Structural basis of R-spondin recognition by LGR5 and RNF43", *Genes & Development*, 27:1345-1350, 2019.
De Cian et al., "Amplification of R-spondin1 signaling induces granulosa cell fate defects and cancers in mouse adult ovary", *Oncogene*, 36(2):208-218, 2017.
Ge et al., "Rspo1/LGR5 pathway promotes cervical cancer cell growth and is correlated with the high pathological grade", *Int. J. Clin. Exp. Pathol*, 9(():9048-9057, 2016.
Glinka et al., "LGR4 and LGR5 are R-spondin receptors mediating Wnt/beta-catenin and Wnt/PCP signaling," *EMBO Rep.*, 12:1055-1061, 2011.

(Continued)

*Primary Examiner* — Hope A Robinson
(74) *Attorney, Agent, or Firm* — Parker Highlander PLLC

(57) ABSTRACT

The invention is directed to cell-targeted cytotoxic agents, including sortase serine protease constructs. Methods for targeted cell killing for treatment of proliferative diseases, for example, cancer, are provided. Exemplary embodiments comprise an R-spondin ligand for targeting the cytotoxic agents to effect the cell killing.

15 Claims, 21 Drawing Sheets

Specification includes a Sequence Listing.

(56) References Cited

OTHER PUBLICATIONS

Gong et al., "LGR6 is a high affinity receptor of R-spondins and potentially functions as a tumor suppressor," *Plos One*, 7(5):e37137, 2012.

Guimaraes et al., "Identification of host cell factors required for intoxication through use of modified cholera toxin," *J Cell Biol*, 195:751-764, 2011.

Jin and Yoon, "The R-spondin family of proteins: emerging regulators of WNT signaling," *Int J Biochem Cell Biol.*, 44(12):2278-2287, 2012.

Junttila et al., "Targeting LGR5+ cells with an antibody-drug conjugate for the treatment of colon cancer", *Sci Trans Med*, 7(314):314ra186, 2015.

Kanatani et al., "Targeting granzyme B to tumor cells using a yoked human chorionic gonadotropin," *Cancer Chemotherapy and Pharmacology*, 68(4):979-990, 2011.

Kessler et al., "The Notch and Wnt pathways regulate stemness and differentiation in human fallopian tube organoids," *Nature communications*, 6:8989, 2015.

Kornberger et al., "Sortase-catalyzed in vitro functionalization of a HER2-specific recombinant Fab for tumor targeting of the plant cytotoxin gelonin," *MABS*, 6(2):354-366, 2014.

Kovtun et al., "Antibody-maytansinoid conjugates designed to bypass multidrug resistance," *Cancer Res.*, 70:2528-2537, 2010.

Lau et al., "The R-spondin/Lgr5/Rnf43 module: regulator of Wnt signal strength," *Genes & Development*, 28:305-316, 2014.

Liu et al., "Targeted apoptosis activation with GrB/scFvMEL modulates melanoma growth, metastatic spread, chemosensitivity, and radiosensitivity," *Neoplasia*, 8:125-35, 2006.

Maderna and Leverett, "Recent advances in the development of new auristatins: structural modifications and application in antibody drug conjugates," *Mol. Pharmaceutics*, 12:1798-1812, 2015.

Mao et al., "Sortase-Mediated Protein Ligation: A New Method for Protein Engineering", *J. Am. Chem. Soc.*, 126, 2670-2671, 2004.

PCT International Search Report and Written Opinion issued in Internatinal Application No. PCT/US2017/018116, dated May 15, 2017.

PIR database R_spondin2 diversity A0A024R914A0A024R914_HUMAN R-s-spondin2. Performed Nov. 15, 2019.

PIR database R_spondin1 diversity D3ZBDID3ZBD1_RAT R-spondin1 vs W5MFN8W5MFN8_LEPOC R-spondin1. Performed Nov. 15, 2019.

Polakis, "Wnt signaling in cancer," *Cold Spring Harb Perspect Biol.*, 4:a008052, 2012.

Popp et al., "Making and Breaking Peptide Bonds: Protein Engineering Using Sortase," *Angew Chem Int Ed*, 50:5024-5032, 2011.

Popp et al., "Sortagging: a versatile method for protein labeling," *Nature Chemical Biology*, 3(11):707-708, 2007.

Snippert et al., "Lgr6 marks stem cells in the hair follicle that generate all cell lineages of the skin," *Science*, 327: 1385-1389, 2010.

Ton-That et al., "Anchoring of surface proteins to the cell wall of *Staphylococcus aureus*. Sortase catalyzed in vitro transpeptidation reaction using LPXTG peptide and NH(2)-Gly(3) substrates," *J Biol Chem.*, 275:9876-9881, 2000.

Tsukiji et al., "Sortase-mediated ligation: a gift from Gram-positive bacteria to protein engineering," *Chembiochem.*, 10:787-98, 2009.

Yamamoto et al., "In Vitro and In Vivo Correlates of Physiologic and Neoplastic Human Fallopian Tube Stem Cells," *The Journal of Pathology*, 238(4):519-530, 2016.

Zhou et al., "Rspo1-activated signalling molecules are sufficient to induce ovarian differentiation in XY medaka (*Oryzias latipes*)," *Scientific Reports*, 6:19543, 2016.

* cited by examiner

GrB-(G4S)2-LPETGG cDNA sequence (729 bp) (SEQ ID NO: 1)

ATCATCGGGGACATGAGGCCCAAGCCCCACTCCCGCCCCTACATGGCTTATCTTATGATCTG
GGATCAGAAGTCTCTGAAGAGCTGCGGTGGCTTCCTGATACAAGACTTCGTGCTGACAG
CTGCTCACTGTTGGGGAAGCTCCATAAATGTCACCTTGGGCCACATATCAAAGAACAG
GAGCCGACCCAGCAGTTTATCCCTGTGAAAGACCCCATCCCAGCCTATAATCCTAA
GAACTTCTCCAACGACATCATGCTACTGCAACTGGAGAGAAAGGCCAAGCGGACCAGAGCTG
TGCAGCCCCCTCAGCTACCTAGCAACAAGGCCCAGGCAAGTGAAGCACACACAGAGCTG
GCCGGGCTGGGCAGAAGATCGAAAGTCGACTTACGCCATTATTACGACAGAGGTGAAGAT
AGTTGTGCTGGGGACCCAGAGATTAAAAAGACTTCCTTTAAGGGGACTCTGGAGCCCT
CTTGTGTGTAACAAGGTCGCAGTCTCAAGTTTGTACACTGGATAAAGAAAACCATGAAACGCTACG
ACGAGCCTGCACCAAAGTCTCCAAGTCTCCGGTGGCGGTGGCTCCCCCGAAAACGGGTGGA

FIG. 5A

GrB-(G4S)2-LPETGG amino acid sequence (243 aa) (SEQ ID NO: 2)

IIGGHEAKPHSRPYMAYLMIWDQKSLKRCGGFLIQDDFVLTAAHCWGSSINVTLGAHNIKEQ
EPTQQFIPVKRPIPHPAYNPKNFSNDIMLLQLERKAKRTRAVQPLRLPSNKAQVKPGQTCSV
AGWGQTAPLGKHSHTLQEVKMTVQEDRKCESDLRHYDSTIELCVGDPEIKKTSFKGDSGGP
LVCNKVAQGIVSYGRNNGMPPRACTKVSSFVHWIKKTMKRYGGGGSGGGGSLPETGG

FIG. 5B

```
H_sapiens*        slkrcggflirdd dfvltaahcwgssin vtlgahni    iiggheakphsrpymaylmiwdqk-
P_troglodytes     tlkrdggflired dfvltaahcwgssin vtlgahni    iiggheakphsrpymaylmiwdqk-
P_paniscus        tlkrcggflired dfvltaahcwgssin vtlgahni    iiggheakphsrpymaylmiwdqk-
P_abelii          slkrcggflired dfvltaahcwgssin vtlgahni    iiggheakphsrpymaylmiwdqk-
M_nemestrina      slkrcggflired dfvltaahcwgssin vtlgahni    iiggheakphsrpymaylmiwdqm-
M_mulatta         slkrcggflired dfvltaahcwgssin vtlgahni    iiggheakphsrpymaylmiwdqm-
M_fascicularis    slkrcggflired dfvltaahcwgssin vtlgahni    iiggheakphsrpymaylmiwdqm-
S_scrofa          nrsrcggflired dfvltaahcwgssin vtlgahni    iiggheakphsrpymaylqiqdqd-
B_taurus          vqsrcggflvrqd dfvltaahcngssik vtlgahni    iiggheakphsrpymaylqywnqd-
R_norvegicus      iiggheakphsrpymaylqimdeysgskkcggflired dfvltaahcsgskin vtlgahni
M_musculus        iigghevkphsrpymallsikdqq-
                  peaicggflired dfvltaahcegsii nvtlgahni
                  *******            *******  *  ************          ******* * ************
```

*FIG. 6A*

| Species | Sequence |
|---|---|
| H_sapiens | keqeptqqfipvkrpiphpaynpkhnfsndimlliqlerkakrtravqpirlpsnkaqvkpg |
| P_troglodytes | keqeptqqfipvkrpiphpaynpkhnfsndimlliqlerkakrtravqpirlpsnkaqvkpg |
| P_paniscus | keqeptqqfipvkrpiphpaynpkhnysndimlliqlerkakrtravqpirlpsnkaqvkpg |
| P_abelii | keqeptqqfipvkrpiphpaynpkhysndimlliqlerkakrtravqpirlpsnkaqvkpg |
| M_nemestrina | keqeqtqqlipvkravrhpaynpkhnfsndimlliqlekkakrttavqpirlpsnkaqvkpg |
| M_mulatta | keqertqqiipvkraiphpaynpehfsndimlliqlerkakrttavqpirlprnkaqvkpg |
| M_fascicularis | keqertqqiipvkraiphpaynpkhnfsndimlliqlerkakrttavqpirlprnkaqvkpg |
| S_scrofa | keqertqqiipvkraiphpaynpkhnfsndimlliqlerkakiitkavktiglpgakarvkpg |
| B_taurus | kkqeetqqvipvrkairhpdynekrisndimlliklerkakqtsavkpislprakarvkpg |
| R_norvegicus | kqqetqqvirvrraishpdynpkhnfsndimlliklerkakqtsavkpislprakarvkpg |
| M_musculus | keqekmqqiipvvkiiphpaynsktisndimliklkskakrssavkpinlprrnvkvkpg |
|  | keqektqqvipmvkciphpdynpktfsndimliklkskakrtravrpinlprrnvnvkpg |

```
H_sapiens
qtcsvagwgqtaplgkhshtltqevkmtvqedrkcesdlrhyydstielcvgdpeikktsf
P_troglodytes
qvcsvagwgqtaplgkhshtlqevkmtvqedrkcesdlrhyydstielcvgdpeikktsf
P_paniscus
qacsvagwgqtaplgkhshtlqevkmtvqedrkcesdlrhyydstielcvgdpeikktsf
P_abelii
qacsvagwgqtaptgkyshtlqevemtvqedrkcksdlrhyydstielcvgdpeikkasf
M_nemestrina
qacdvagwgqtaptgkyshtlqevkltveedqtcksrlghyydstvelcvgdpeiqkasf
M_mulatta
qacdvagwgqttpdgkyshtlqevkltveedqtcksrlgryydstvelcvgdpeiqkasf
M_fascicularis
qacdvagwgqttpdgkyshtlqevkltveedqtcksrlgryydstvelcvgdpeiqkasf
S_scrofa       qvcsvagwgqve-   qecdsylpnyyngntqlcvgdpkkkqatf
rgiytdtlqevkltiqkd
B_taurus       qtcsvagwgrds-
tdtyadtlqevklivqedqkceaylrnfynraiqlcvgdpktkkasf
R_norvegicus
dvcyvagwgklgpmgkysdtlqeveltvqedqkcesylknyfdkaneicagdpkikrasf
M_musculus
dvcyvagwgrmapmgkysntlqeveltvqkdrecesyfknrynktnqicvgdpktkrasf
     *****       *****       *        *     *     ****
```

FIG. 6A
(Cont'd)

```
H_sapiens       kgdsggplvcnkvaggivsygrnngmppract kvssfvhwikktmkry
P_troglodytes   kgdsggplvcnkvaggivsygrnngmppract kvssfvhwikktmkrh
P_paniscus      kgdsggplvcnkvaggivsygrnngmppract kvssfvhwikktmkrh
P_abelii        kgdsggplvcnkvaggivsygrnngmppract kvssfvhwikktmkrh
M_nemestrina    kgdsggplvcnkvaggivsygrnngmpprvct kvssfvhwikktmkrh
M_mulatta       kgdsggplvcnkvaggivsygqrngkpprvct kvssfvrwikktmkrh
M_fascicularis  kgdsggplvcnkvaggivsygqrngkpprvct kvssfvrwikktmkrh
S_scrofa        kgdsggplvcnnvaggivsygkkngtppract kvssfvrwikktmkrh
B_taurus        qgdsggplvcdnvaggivsygkrdgstpraft kvstfvrwikkimksl
R_norvegicus    rgdsggplvckkvaagivsyggqndgstpraft kvstflswikktmkks
M_musculus      rgdsggplvckkvaagivsyggykdgspppraft kvssflswikktmkss
                *****  ***  ** ****** *          ***  * ****   *
```

*FIG. 6A (Cont'd)*

```
Gzm B    1  IIGGHEAKPHSRPYMAYLMIWDQKSLKRCGGFLIRDDFVLTAAHCWG----SSINVTLG    55
Gzm A    1  IIGGNEVTPHSRPYMVLLSLD----RKTICAGALIAKDWVLTAAHCNLN----KRSQVILG   53
Gzm H    1  IIGGHEAKPHSRPYMAFVQFLQEKSRKRCGGILVRKDFVLTAAHCQG----SSINVTLG    55
Gzm K    1  IIGGKEVSPHSRPFMASIQYG----GHHVCGGVLIDPQWVLTAAHCQYRFTKGQSPTVVLG   57
Gzm M    1  IIGGREVIPHSRPYMASLQRN----GSHLCGGVLVHPKWVLTAAHCLAQRM--AQLRLVLG   55
             ** *  ***** *          .    * *    *****   .:

Gzm B   56  AHNIKEQEPTQQFIPVKRPIPHPAYNPKN-FSNDIMLLQLERKAKRTRAVQPLRLPSNKA   114
Gzm A   54  AHSITREEPTKQIMLVKKEFPYPCYDPAT-REGDLKLLQLMEKAKINKYVTILHLPKKGD   112
Gzm H   56  AHNIKEQERTQQFIPVKRPIPHPAYNPKN-FSNDIMLLQLERKAKWTTAVRPLRLPSSKA   114
Gzm K   58  AHSLSKNEASKQTLEIKKFIPFSRVTSDP-QSNDIMLVKLQTAAKLNKHVKMLHIRSK-T  115
Gzm M   56  LHTLDSP----GLTFEHIKAAIQHPRYKPVPALENDLALLQLDGKVKPSRTIRPLALPSKRQ 112
             *   .          : *           .  :*::*      *

Gzm B  115  QVKPGQTCSVAGWGQTAP-LGKHSHTLQEVKMTVQEDRKCESDLRHYYDST---IELCVG   170
Gzm A  113  DVKPGTMCQVAGWGRTHN-SASWSDTLREVNITIIDRKVCNDRNHYNFNPVIGMNMVCAG  171
Gzm H  115  QVKPGQLCSVAGWGYVS--MSTLATTLQEVLLTVQKDCQCERLFHGNYSRA---TEICVG  169
Gzm K  116  SLRSGTKCKVTGWGATDPDSLRPSDTLREVTVTVLSRKLCNSQSYYNGDPFITKDMVCAG  175
Gzm M  113  VVAAGTRCSMAGWGLTHQ-GGRLSRVLRELDLQVLDTRMCNNSRFWNGS--LSPSMVCLA  169
             .      *  ***           *      *    .  :          . .

FIG. 6B
```

| | | | |
|---|---|---|---|
| Gzm B | 171 | DPEIKKTSFKGDSGGPLVCNK---VAQGIVSYGRN---NG---MPPRACTKVS-SFVHWIKKT | 223 |
| Gzm A | 172 | SLRGGRDSCNGDSGSPLLCEG---VFRGVTSFGLENKCCGDPRGPGVYILLSKKHLNWIIMT | 229 |
| Gzm H | 170 | DPKKTQTGFKGDSGGPLVCKD---VAQGILSYGNK---KG---TPPGVYIKVS-HFLPWIKRT | 222 |
| Gzm K | 176 | DAKGQKDSCKGDSGGPLICKG---VFHAIVSGG---HECGVATKPGIYTLLTKKYQTWIKSN | 231 |
| Gzm M | 170 | ADSKDQAPCKGDSGGPLVCGKGRVLARVLSFSSR-VCTDIFKPPVATAVA-PYVSWIRKV | 227 |
| | | .:****.:.**.*.***:.*      *     .:           :  .   ** | |
| Gzm B | 224 | MKRY---- | 227 |
| Gzm A | 230 | IKGAV--- | 234 |
| Gzm H | 223 | MKRL---- | 226 |
| Gzm K | 232 | LVPPHTN- | 238 |
| Gzm M | 228 | TGRSA--- | 232 |

FIG. 6B
(Cont'd)

```
Granzyme B            1   IIGGHEAKPHSRPYMAYLMIWDQKS-LKRCGGFLIRDDFVLTAAHCWG-----SSINVTLG   55
Cathepsin G           1   IIGGRESRPHSRPYMAYLQIQSPAG-QSRCGGFLVREDFVLTAAHCWG-----SNINVTLG   55
Chymase               1   IIGGTECKPHSRPYMAYLEIVTSNGPSKFCGGFLIRRNFVLTAAHCAG-----RSITVTLG   56
Myeloblastin          1   IVGGHEAQPHSRPYMASLQMRGNPG-SHFCGGTLIHPSFVLTAAHCLRDIPQRLVNVVLG   59
Kallikrein-14         1   IIGGHTCTRSSQPWQAALLAGP---RRRFLCGGALLSGQWVITAAHCGR-----PILQVALG   54
Complement factor D   1   ILGGREAEAHARPYMASVQLNG----AHLCGGVIVAEQWVLSAAHCLEDAADGKVQVLLG   56
PRSS3 protein         1   IVGGYTCEENSLPYQVSLNSG----SHFCGGSLISEQWVSAAHCYK-----TRIQVRLG   51
Trypsin-1             1   IVGGYNCEENSVPYQVSLNSG----YHFCGGSLINEQWVSAGHCYK-----SRIQVRLG   51
Serine protease 57    1   IIGGHEVTPHSRPYMASVRFGG----QHHCGGFLLRARWVSAAHCFSHRDLRTGLVVLG   56
PRSSL1 protein        1   IIGGHEVTPHSRPYMASVRFGG----QHHCGGFLLRARWVSAAHCFSHRDLRTGLVVLG   56
                          *:*      *:*          .     . *** *  *  :: :*.*   .*

Granzyme B           56   AHNIKEQEPTQQFIPVKRPIPHPAYNPKNFSNDIMLLQLERKAKRTRAVQPLRLP-SNKA   114
Cathepsin G          56   AHNIQRRENTQQHITARRAIRHPQYNQRTIQNDIMLLQLERKAKRTRAVQPLRLP-SNKA   114
Chymase              57   AHNITEEEDTWQKLEVIKQFRHPKYNTSTLHHDIMLLKLKEKASLTLAVGTLPFP-SQFN   115
Myeloblastin         60   AHNVRTQEPTQQHFSVAQVFL-NNYDAENKLNDVLLIQLSSPANLSASVATVQLP-QQDQ   117
Kallikrein-14        55   KHNLRRWEATQQVLRVVRQVTHPNYNSRTHDNDLMLLQLQQPARIGRAVRPIEVT----QA   111
Complement factor D  57   AHSLSQPEPSKRLYDVLRAVPHPDSQPDTIDHDLLLLQLSEKATLGPAVRPLP-WQRVDR   115
PRSS3 protein        52   EHNIKVLEGNEQFINAAKIIRHPQYDRKTLNNDIMLIKLSSRAVINARVSTISLP----TA   108
Trypsin-1            52   EHNIEVLEGNEQFINAAKIIRHPQYDRKTLNNDIMLIKLSSRAVINARVSTISLP----TA   108
Serine protease 57   57   AHVLSTAEPTQQVFGIDALTTHPDYHPMTHANDICLLRLNGSAVLGPAVGLLRPPGRRAR   116
PRSSL1 protein       57   AHVLSTAEPTQQVFGIDALTTHPDYHPMTHANDICLLRLNGSAVLGPAVGLLRLPGRRAR   116
                           *      .          .          . *:.:  *::. .    ..
```

FIG. 6C

| | | | |
|---|---|---|---|
| Granzyme B | 115 | QVKPGQTCSVAGWGQTA-PLGKHSHTLQEVKMTVQEDRKCESDLRHYYDST-IELCVG-D | 171 |
| Cathepsin G | 115 | GLRPGTLCTVAGWGRVS--MRRGTDTLREVQLRVQRDRQCLRIFG-SYDPR-RQICVG-D | 169 |
| Chymase | 116 | FVPPGRMCRVAGWGRTG-VLKPGSDTLQEVKLRLIMDPQACSHFR--DFDHN-LQLCVG-N | 170 |
| Myeloblastin | 118 | PVPHGTQCLAMGWGRVG-AHDPPAQVLQELNVTVT-------FFCRP-HNICTF-V | 164 |
| Kallikrein-14 | 112 | CASPGTSCRVSGWGTISSPIARYPASLQCVNINISPDEVCQKAY--PRTITPGMVCAG-V | 168 |
| Complement factor D | 116 | DVAPGTLCDVAGWGIVN-HAGRRPDSLQHVLLPVLDRATCNRRTHHDGAITERLMCA--- | 171 |
| PRSS3 protein | 109 | PPATGTKCLISGWGNTASSGADYPDELQCLDAPVLSQAKCEASY--PGKITSNMFCVG-F | 165 |
| Trypsin-1 | 109 | PPATGTKCLISGWGNTASSGADYPDELQCLDAPVLSQAKCEASY--PGKITSNMFCVG-F | 165 |
| Serine protease 57 | 117 | PPTAGTRCRVAGWGFVS-DFEELPPGLMEAKVRVLDPDVCNSSW--KGHLTLTMLCTRSG | 173 |
| PRSSL1 protein | 117 | PPTAGTRCRVAGWGFVS-DFEELPPGLMEAKVRVLDPDVFNSSW--KGHLTLTMLCTRSG | 173 |
| | | *    *   *               *:                         : | |
| Granzyme B | 172 | PEIKKTSFKGDSGGPLVCNKVAQGIVS----YGRNNGMPPRACTKVSSFVHWIKKTMKRY- | 227 |
| Cathepsin G | 170 | RRERKAAFKGDSGGPLLCNNVAHGIVS----YGKSSGVPPEVFTRVSSFLPWIRTTMRSFK | 226 |
| Chymase | 171 | PRKTKSAFKGDSGGPLLCAGVAQGIVS----YGRSDAKPPAVFTRISHYRPWINQILQAN- | 226 |
| Myeloblastin | 165 | PRRKAGICFGDSGGPLICDGIIQGIDSFVIWGCATRLFPDFFTRVALYVDWIRSTLRRVE | 224 |
| Kallikrein-14 | 169 | PQGGKDSCQGDSGGPLVCRGQLQGLVSWGMERCALPGYPGVYTNLCKYRSWIEETMRDK-- | 227 |
| Complement factor D | 172 | ESNRRDSCKGDSGGPLVCGGVLEGVTSGSRVCGNRKKPGIYTRVASYAAWIDSVLA---- | 228 |
| PRSS3 protein | 166 | LEGGKDSCQGDSGGPVVCNGQLQGVVSWGD-GCAQKNKPGVYTKVYNYVKWIKNTIAANS | 224 |
| Trypsin-1 | 166 | LEGGKDSCQGDSGGPVVCNGQLQGVVSWGD-GCAQKNKPGVYTKVYNYVKWIKNTIAANS | 224 |
| Serine protease 57 | 174 | DSHRRGFCSADSGGPLVCRNRAHGLVSFSGLWCGDPKTPDVYTQVSAFVAWIWDVVRSS | 233 |
| PRSSL1 protein | 174 | DSHRRGFCSADSGGPLVCRNRAHGLVSFSGLWCGDPKTPDVYTQVSAFVAWIWDVVRSS | 233 |
| | | .  : ****:.*                   :        *:                 | |

FIG. 6C (Cont'd)

| | | | |
|---|---|---|---|
| Granzyme B | 228 | ---------- | 227 |
| Cathepsin G | 227 | LLDQMETPL- | 235 |
| Chymase | 227 | ---------- | 226 |
| Myeloblastin | 225 | AKGRP----- | 229 |
| Kallikrein-14 | 228 | ---------- | 227 |
| Complement factor D | 229 | ---------- | 228 |
| PRSS3 protein | 225 | ---------- | 224 |
| Trypsin-1 | 225 | ---------- | 224 |
| Serine protease 57 | 234 | PQPGPLPGTTRPPGEAA | 250 |
| PRSSL1 protein | 234 | PQPGPLPGTTRPPGEAA | 250 |

*FIG. 6C (Cont'd)*

SEQUENCE LISTING

<160> NUMBER OF SEQ ID NOS: 110

<210> SEQ ID NO 1
<211> LENGTH: 729
<212> TYPE: DNA
<213> ORGANISM: Artificial Sequence
<220> FEATURE:
<223> OTHER INFORMATION: Synthetic nucleic acid

<400> SEQUENCE: 1

```
atcatcgggg gacatgaggc caagcccac tcccgcccct acatggctta tcttatgatc      60
tgggatcaga agtctctgaa gaggtgcggt ggcttcctga tacaagacga cttcgtgctg     120
acagctgctc actgttgggg aagctccata aatgtcacct tggggcccca caatatcaaa     180
gaacaggagc cgacccagca gtttatccct gtgaaaagac ccatccccca tccagcctat     240
aatcctaaga acttctccaa cgacatcatg ctactgcagc tggagagaaa ggccaagcgg     300
accagagctg tgcagcccct caggctacct agcaacaagg cccaggtgaa gccagggcag     360
acatgcagtg tggccggctg ggggcagacg gccccctgg gaaaacactc acacacacta     420
caagaggtga agatgacagt gcaggaagat cgaaagtgcg aatctgactt acgccattat     480
tacgacagta ccattgagtt gtgcgtgggg gacccagaga ttaaaaagac ttcctttaag     540
ggggactctg gaggccctct tgtgtgtaac aaggtggccc agggcattgt ctcctatgga     600
cgaaacaatg gcatgcctcc acgagcctgc accaaagtct caagctttgt acactggata     660
aagaaaacca tgaaacgcta cggtggcggt ggctccggtg gcggtggctc cctcccggaa     720
acgggtgga                                                            729
```

-continued

<210> SEQ ID NO 2
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 2

```
Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Gly Gly Gly Ser Gly Gly Gly Ser Leu Pro Glu
225                 230                 235                 240

Thr Gly Gly
```

<210> SEQ ID NO 3
<211> LENGTH: 227
<212> TYPE: PRT
<213> ORGANISM: Homo sapiens

<400> SEQUENCE: 3

```
Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
```

```
            65                  70                  75                  80
Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
            115                 120                 125

Gln Thr Ala Pro Leu Gly Lys His Ser His Thr Leu Gln Glu Val Lys
            130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
            195                 200                 205

Ala Cys Thr Lys Val Ser Ser Phe Val His Trp Ile Lys Lys Thr Met
210                 215                 220

Lys Arg Tyr
225

<210> SEQ ID NO 4
<211> LENGTH: 227
<212> TYPE: PRT
<213> ORGANISM: Pan troglodytes

<400> SEQUENCE: 4

Ile Ile Gly Gly His Glu Ala Lys Pro His Ser Arg Pro Tyr Met Ala
1               5                   10                  15

Tyr Leu Met Ile Trp Asp Gln Lys Thr Leu Lys Arg Cys Gly Gly Phe
                20                  25                  30

Leu Ile Arg Glu Asp Phe Val Leu Thr Ala Ala His Cys Trp Gly Ser
            35                  40                  45

Ser Ile Asn Val Thr Leu Gly Ala His Asn Ile Lys Glu Gln Glu Pro
        50                  55                  60

Thr Gln Gln Phe Ile Pro Val Lys Arg Pro Ile Pro His Pro Ala Tyr
65                  70                  75                  80

Asn Pro Lys Asn Tyr Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Val Cys Ser Val Ala Gly Trp Gly
            115                 120                 125

Gln Thr Ala Pro Leu Gly Lys His Ser His Thr Leu Gln Glu Val Lys
            130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
            195                 200                 205
```

-continued

```
Ala Cys Thr Lys Val Ser Ser Phe Val His Trp Ile Lys Lys Thr Met
    210                 215                 220

Lys Arg His
225

<210> SEQ ID NO 5
<211> LENGTH: 227
<212> TYPE: PRT
<213> ORGANISM: Pan paniscus

<400> SEQUENCE: 5

Ile Ile Gly Gly His Glu Ala Lys Pro His Ser Arg Pro Tyr Met Ala
1               5                   10                  15

Tyr Leu Met Ile Trp Asp Gln Lys Thr Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Pro
50                  55                  60

Thr Gln Gln Phe Ile Pro Val Lys Arg Pro Ile Pro His Pro Ala Tyr
65                  70                  75                  80

Asn Pro Lys Asn Tyr Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Ala Cys Ser Val Ala Gly Trp Gly
        115                 120                 125

Gln Thr Ala Pro Leu Gly Lys His Ser His Thr Leu Gln Glu Val Lys
130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg His
225

<210> SEQ ID NO 6
<211> LENGTH: 227
<212> TYPE: PRT
<213> ORGANISM: Pongo abelii

<400> SEQUENCE: 6

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Gln
50                  55                  60
```

```
Thr Gln Gln Leu Ile Pro Val Lys Arg Ala Val Arg His Pro Ala Tyr
 65                  70                  75                  80

Asn Pro Lys Asn Phe Ser Asn Asp Ile Met Leu Leu Gln Leu Glu Lys
                 85                  90                  95

Lys Ala Lys Arg Thr Thr Ala Val Gln Pro Leu Arg Leu Pro Ser Asn
            100                 105                 110

Lys Ala Gln Val Lys Pro Gly Gln Ala Cys Ser Val Ala Gly Trp Gly
        115                 120                 125

Gln Thr Ala Pro Thr Gly Lys Tyr Ser His Thr Leu Gln Glu Val Glu
    130                 135                 140

Met Thr Val Gln Glu Asp Arg Lys Cys Lys Ser Asp Leu Arg His Tyr
145                 150                 155                 160

Tyr Asp Ser Thr Ile Glu Leu Cys Val Gly Asp Pro Glu Ile Lys Lys
                165                 170                 175

Ala Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Val Cys Thr Lys Val Ser Ser Phe Val His Trp Ile Lys Lys Thr Met
    210                 215                 220

Lys Arg His
225

<210> SEQ ID NO 7
<211> LENGTH: 227
<212> TYPE: PRT
<213> ORGANISM: Macaca nemestrina

<400> SEQUENCE: 7

Ile Ile Gly Gly His Glu Ala Lys Pro His Ser Arg Pro Tyr Met Ala
  1               5                  10                  15

Tyr Leu Met Ile Trp Asp Gln Met Ser Leu Lys Arg Cys Gly Gly Phe
                 20                  25                  30

Leu Ile Arg Glu Asp Phe Val Leu Thr Ala Ala His Cys Trp Gly Ser
             35                  40                  45

Ser Ile Asn Val Thr Leu Gly Ala His Asn Ile Lys Glu Gln Glu Arg
 50                  55                  60

Thr Gln Gln Ile Ile Pro Val Lys Arg Ala Ile Pro His Pro Ala Tyr
 65                  70                  75                  80

Asn Pro Glu Asn Phe Ser Asn Asp Ile Met Leu Leu Gln Leu Glu Arg
                 85                  90                  95

Lys Ala Lys Arg Thr Thr Ala Val Gln Pro Leu Arg Leu Pro Arg Asn
            100                 105                 110

Lys Ala Gln Val Lys Pro Gly Gln Ala Cys Asp Val Ala Gly Trp Gly
        115                 120                 125

Gln Thr Thr Pro Asp Gly Lys Tyr Ser His Thr Leu Gln Glu Val Lys
    130                 135                 140

Leu Thr Val Glu Glu Asp Gln Thr Cys Lys Ser Arg Leu Gly His Tyr
145                 150                 155                 160

Tyr Asp Ser Thr Val Glu Leu Cys Val Gly Asp Pro Glu Ile Gln Lys
                165                 170                 175

Ala Ser Phe Lys Gly Asp Ser Gly Gly Pro Leu Val Cys Asn Lys Val
            180                 185                 190

Ala Gln Gly Ile Val Ser Tyr Gly Gln Arg Asn Gly Lys Pro Pro Arg
        195                 200                 205
```

```
Val Cys Thr Lys Val Ser Ser Phe Val Arg Trp Ile Lys Lys Thr Met
    210                 215                 220

Lys Arg His
225

<210> SEQ ID NO 8
<211> LENGTH: 227
<212> TYPE: PRT
<213> ORGANISM: Macaca mulatta

<400> SEQUENCE: 8

Ile Ile Gly Gly His Glu Ala Lys Pro His Ser Arg Pro Tyr Met Ala
1               5                   10                  15

Tyr Leu Met Ile Trp Asp Gln Met Ser Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Arg
    50                  55                  60

Thr Gln Gln Ile Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Thr Ala Val Lys Pro Leu Arg Leu Pro Arg Asn
            100                 105                 110

Lys Ala Gln Val Lys Pro Gly Gln Ala Cys Asp Val Ala Gly Trp Gly
        115                 120                 125

Gln Thr Thr Pro Asp Gly Lys Tyr Ser His Thr Leu Gln Glu Val Lys
    130                 135                 140

Leu Thr Val Glu Glu Asp Gln Thr Cys Lys Ser Arg Leu Gly Arg Tyr
145                 150                 155                 160

Tyr Asp Ser Thr Val Glu Leu Cys Val Gly Asp Pro Glu Ile Gln Lys
                165                 170                 175

Ala Ser Phe Lys Gly Asp Ser Gly Gly Pro Leu Val Cys Asn Lys Val
            180                 185                 190

Ala Gln Gly Ile Val Ser Tyr Gly Gln Arg Asn Gly Lys Pro Pro Arg
        195                 200                 205

Val Cys Thr Lys Val Ser Ser Phe Val Arg Trp Ile Lys Lys Thr Met
    210                 215                 220

Lys Arg His
225

<210> SEQ ID NO 9
<211> LENGTH: 227
<212> TYPE: PRT
<213> ORGANISM: Macaca fascicularis

<400> SEQUENCE: 9

Ile Ile Gly Gly His Glu Ala Lys Pro His Ser Arg Pro Tyr Met Ala
1               5                   10                  15

Tyr Leu Met Ile Trp Asp Gln Met Ser Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Arg
    50                  55                  60
```

```
Thr Gln Gln Ile Ile Pro Val Lys Arg Ala Ile Pro His Pro Ala Tyr
 65                  70                  75                  80

Asn Pro Lys Asn Phe Ser Asn Asp Ile Met Leu Leu Gln Leu Glu Arg
                 85                  90                  95

Lys Ala Lys Arg Thr Thr Ala Val Lys Pro Leu Arg Leu Pro Arg Asn
            100                 105                 110

Lys Ala Gln Val Lys Pro Gly Gln Ala Cys Asp Val Ala Gly Trp Gly
            115                 120                 125

Gln Thr Thr Pro Asp Gly Lys Tyr Ala His Thr Leu Gln Glu Val Lys
130                 135                 140

Leu Thr Val Glu Glu Asp Gln Thr Cys Lys Ser Arg Leu Gly Arg Tyr
145                 150                 155                 160

Tyr Asp Ser Thr Val Glu Leu Cys Val Gly Asp Pro Glu Ile Gln Lys
                165                 170                 175

Ala Ser Phe Lys Gly Asp Ser Gly Gly Pro Leu Val Cys Asn Lys Val
            180                 185                 190

Ala Gln Gly Ile Val Ser Tyr Gly Gln Arg Asn Gly Lys Pro Pro Arg
            195                 200                 205

Val Cys Thr Lys Val Ser Ser Phe Val Arg Trp Ile Lys Lys Thr Met
210                 215                 220

Lys Arg His
225

<210> SEQ ID NO 10
<211> LENGTH: 226
<212> TYPE: PRT
<213> ORGANISM: Sus scrofa

<400> SEQUENCE: 10

Ile Ile Gly Gly His Glu Ala Lys Pro His Ser Arg Pro Tyr Met Ala
 1               5                  10                  15

Tyr Leu Gln Ile Gln Asp Gln Asp Asn Arg Ser Arg Cys Gly Gly Phe
             20                  25                  30

Leu Ile Arg Glu Asp Phe Val Leu Thr Ala Ala His Cys Trp Gly Ser
         35                  40                  45

Ser Ile Asn Val Thr Leu Gly Ala His Asn Ile Lys Lys Gln Glu Glu
 50                  55                  60

Thr Gln Gln Val Ile Pro Val Arg Lys Ala Ile Arg His Pro Asp Tyr
 65                  70                  75                  80

Asn Glu Lys Arg Ile Ser Asn Asp Ile Met Leu Leu Gln Leu Glu Arg
                 85                  90                  95

Lys Ala Lys Leu Thr Lys Ala Val Lys Thr Leu Gly Leu Pro Gly Ala
            100                 105                 110

Lys Ala Arg Val Lys Pro Gly Gln Val Cys Ser Val Ala Gly Trp Gly
            115                 120                 125

Gln Val Glu Arg Gly Ile Tyr Thr Asp Thr Leu Gln Glu Val Lys Leu
130                 135                 140

Thr Leu Gln Lys Asp Gln Glu Cys Asp Ser Tyr Leu Pro Asn Tyr Tyr
145                 150                 155                 160

Asn Gly Asn Thr Gln Leu Cys Val Gly Asp Pro Lys Lys Lys Gln Ala
                165                 170                 175

Thr Phe Lys Gly Asp Ser Gly Gly Pro Leu Val Cys Asn Asn Val Ala
            180                 185                 190

Gln Gly Ile Val Ser Tyr Gly Lys Lys Asp Gly Thr Pro Pro Arg Ala
```

```
                195                 200                 205
Cys Thr Lys Val Ser Ser Phe Leu Pro Trp Ile Lys Lys Ile Met Lys
    210                 215                 220

Ser Leu
225

<210> SEQ ID NO 11
<211> LENGTH: 226
<212> TYPE: PRT
<213> ORGANISM: Bos taurus

<400> SEQUENCE: 11

Ile Ile Gly Gly His Glu Ala Lys Pro His Ser Arg Pro Tyr Met Ala
1               5                   10                  15

Tyr Leu Gln Tyr Trp Asn Gln Asp Val Gln Ser Arg Cys Gly Gly Phe
            20                  25                  30

Leu Val Arg Gln Asp Phe Val Leu Thr Ala Ala His Cys Asn Gly Ser
        35                  40                  45

Ser Ile Lys Val Thr Leu Gly Ala His Asn Ile Lys Gln Gln Glu Arg
    50                  55                  60

Thr Gln Gln Val Ile Arg Val Arg Arg Ala Ile Ser His Pro Asp Tyr
65                  70                  75                  80

Asn Pro Lys Asn Phe Ser Asn Asp Ile Met Leu Leu Lys Leu Glu Arg
                85                  90                  95

Lys Ala Lys Gln Thr Ser Ala Val Lys Pro Leu Ser Leu Pro Arg Ala
            100                 105                 110

Lys Ala Arg Val Lys Pro Gly Gln Thr Cys Ser Val Ala Gly Trp Gly
        115                 120                 125

Arg Asp Ser Thr Asp Thr Tyr Ala Asp Thr Leu Gln Glu Val Lys Leu
    130                 135                 140

Ile Val Gln Glu Asp Gln Lys Cys Glu Ala Tyr Leu Arg Asn Phe Tyr
145                 150                 155                 160

Asn Arg Ala Ile Gln Leu Cys Val Gly Asp Pro Lys Thr Lys Lys Ala
                165                 170                 175

Ser Phe Gln Gly Asp Ser Gly Gly Pro Leu Val Cys Asp Asn Val Ala
            180                 185                 190

Gln Gly Ile Val Ser Tyr Gly Lys Arg Asp Gly Ser Thr Pro Arg Ala
        195                 200                 205

Phe Thr Lys Val Ser Ser Phe Leu Pro Trp Ile Lys Lys Thr Met Lys
    210                 215                 220

Ser Leu
225

<210> SEQ ID NO 12
<211> LENGTH: 228
<212> TYPE: PRT
<213> ORGANISM: Rattus norvegicus

<400> SEQUENCE: 12

Ile Ile Gly Gly His Glu Ala Lys Pro His Ser Arg Pro Tyr Met Ala
1               5                   10                  15

Tyr Leu Gln Ile Met Asp Glu Tyr Ser Gly Ser Lys Lys Cys Gly Gly
            20                  25                  30

Phe Leu Ile Arg Glu Asp Phe Val Leu Thr Ala Ala His Cys Ser Gly
        35                  40                  45

Ser Lys Ile Asn Val Thr Leu Gly Ala His Asn Ile Lys Glu Gln Glu
```

```
            50                  55                  60
Lys Met Gln Gln Ile Ile Pro Val Val Lys Ile Ile Pro His Pro Ala
 65                  70                  75                  80

Tyr Asn Ser Lys Thr Ile Ser Asn Asp Ile Met Leu Leu Lys Leu Lys
                 85                  90                  95

Ser Lys Ala Lys Arg Ser Ser Ala Val Lys Pro Leu Asn Leu Pro Arg
            100                 105                 110

Arg Asn Val Lys Val Lys Pro Gly Asp Val Cys Tyr Val Ala Gly Trp
                115                 120                 125

Gly Lys Leu Gly Pro Met Gly Lys Tyr Ser Asp Thr Leu Gln Glu Val
130                 135                 140

Glu Leu Thr Val Gln Glu Asp Gln Lys Cys Glu Ser Tyr Leu Lys Asn
145                 150                 155                 160

Tyr Phe Asp Lys Ala Asn Glu Ile Cys Ala Gly Asp Pro Lys Ile Lys
                165                 170                 175

Arg Ala Ser Phe Arg Gly Asp Ser Gly Gly Pro Leu Val Cys Lys Lys
                180                 185                 190

Val Ala Ala Gly Ile Val Ser Tyr Gly Gln Asn Asp Gly Ser Thr Pro
                195                 200                 205

Arg Ala Phe Thr Lys Val Ser Thr Phe Leu Ser Trp Ile Lys Lys Thr
            210                 215                 220

Met Lys Lys Ser
225

<210> SEQ ID NO 13
<211> LENGTH: 227
<212> TYPE: PRT
<213> ORGANISM: Mus musculus

<400> SEQUENCE: 13

Ile Ile Gly Gly His Glu Val Lys Pro His Ser Arg Pro Tyr Met Ala
 1               5                  10                  15

Leu Leu Ser Ile Lys Asp Gln Gln Pro Glu Ala Ile Cys Gly Gly Phe
                20                  25                  30

Leu Ile Arg Glu Asp Phe Val Leu Thr Ala Ala His Cys Glu Gly Ser
            35                  40                  45

Ile Ile Asn Val Thr Leu Gly Ala His Asn Ile Lys Glu Gln Glu Lys
         50                  55                  60

Thr Gln Gln Val Ile Pro Met Val Lys Cys Ile Pro His Pro Asp Tyr
 65                  70                  75                  80

Asn Pro Lys Thr Phe Ser Asn Asp Ile Met Leu Leu Lys Leu Lys Ser
                 85                  90                  95

Lys Ala Lys Arg Thr Arg Ala Val Arg Pro Leu Asn Leu Pro Arg Arg
            100                 105                 110

Asn Val Asn Val Lys Pro Gly Asp Val Cys Tyr Val Ala Gly Trp Gly
                115                 120                 125

Arg Met Ala Pro Met Gly Lys Tyr Ser Asn Thr Leu Gln Glu Val Glu
130                 135                 140

Leu Thr Val Gln Lys Asp Arg Glu Cys Glu Ser Tyr Phe Lys Asn Arg
145                 150                 155                 160

Tyr Asn Lys Thr Asn Gln Ile Cys Val Gly Asp Pro Lys Thr Lys Arg
                165                 170                 175

Ala Ser Phe Arg Gly Asp Ser Gly Gly Pro Leu Val Cys Lys Lys Val
                180                 185                 190
```

```
Ala Ala Gly Ile Val Ser Tyr Gly Tyr Lys Asp Gly Ser Pro Pro Arg
            195                 200                 205

Ala Phe Thr Lys Val Ser Ser Phe Leu Ser Trp Ile Lys Lys Thr Met
210                 215                 220

Lys Ser Ser
225

<210> SEQ ID NO 14
<211> LENGTH: 234
<212> TYPE: PRT
<213> ORGANISM: Homo sapiens

<400> SEQUENCE: 14

Ile Ile Gly Gly Asn Glu Val Thr Pro His Ser Arg Pro Tyr Met Val
1               5                   10                  15

Leu Leu Ser Leu Asp Arg Lys Thr Ile Cys Ala Gly Ala Leu Ile Ala
            20                  25                  30

Lys Asp Trp Val Leu Thr Ala Ala His Cys Asn Leu Asn Lys Arg Ser
        35                  40                  45

Gln Val Ile Leu Gly Ala His Ser Ile Thr Arg Glu Glu Pro Thr Lys
    50                  55                  60

Gln Ile Met Leu Val Lys Lys Glu Phe Pro Tyr Pro Cys Tyr Asp Pro
65                  70                  75                  80

Ala Thr Arg Glu Gly Asp Leu Lys Leu Leu Gln Leu Met Glu Lys Ala
                85                  90                  95

Lys Ile Asn Lys Tyr Val Thr Ile Leu His Leu Pro Lys Lys Gly Asp
            100                 105                 110

Asp Val Lys Pro Gly Thr Met Cys Gln Val Ala Gly Trp Gly Arg Thr
        115                 120                 125

His Asn Ser Ala Ser Trp Ser Asp Thr Leu Arg Glu Val Asn Ile Thr
    130                 135                 140

Ile Ile Asp Arg Lys Val Cys Asn Asp Arg Asn His Tyr Asn Phe Asn
145                 150                 155                 160

Pro Val Ile Gly Met Asn Met Val Cys Ala Gly Ser Leu Arg Gly Gly
                165                 170                 175

Arg Asp Ser Cys Asn Gly Asp Ser Gly Ser Pro Leu Leu Cys Glu Gly
            180                 185                 190

Val Phe Arg Gly Val Thr Ser Phe Gly Leu Glu Asn Lys Cys Gly Asp
        195                 200                 205

Pro Arg Gly Pro Gly Val Tyr Ile Leu Leu Ser Lys Lys His Leu Asn
    210                 215                 220

Trp Ile Ile Met Thr Ile Lys Gly Ala Val
225                 230

<210> SEQ ID NO 15
<211> LENGTH: 226
<212> TYPE: PRT
<213> ORGANISM: Homo sapiens

<400> SEQUENCE: 15

Ile Ile Gly Gly His Glu Ala Lys Pro His Ser Arg Pro Tyr Met Ala
1               5                   10                  15

Phe Val Gln Phe Leu Gln Glu Lys Ser Arg Lys Arg Cys Gly Gly Ile
            20                  25                  30

Leu Val Arg Lys Asp Phe Val Leu Thr Ala Ala His Cys Gln Gly Ser
        35                  40                  45
```

```
Ser Ile Asn Val Thr Leu Gly Ala His Asn Ile Lys Glu Gln Glu Arg
    50                  55                  60

Thr Gln Gln Phe Ile Pro Val Lys Arg Pro Ile Pro His Pro Ala Tyr
 65                  70                  75                  80

Asn Pro Lys Asn Phe Ser Asn Asp Ile Met Leu Leu Gln Leu Glu Arg
                 85                  90                  95

Lys Ala Lys Trp Thr Thr Ala Val Arg Pro Leu Arg Leu Pro Ser Ser
            100                 105                 110

Lys Ala Gln Val Lys Pro Gly Gln Leu Cys Ser Val Ala Gly Trp Gly
            115                 120                 125

Tyr Val Ser Met Ser Thr Leu Ala Thr Thr Leu Gln Glu Val Leu Leu
    130                 135                 140

Thr Val Gln Lys Asp Cys Gln Cys Glu Arg Leu Phe His Gly Asn Tyr
145                 150                 155                 160

Ser Arg Ala Thr Glu Ile Cys Val Gly Asp Pro Lys Lys Thr Gln Thr
                165                 170                 175

Gly Phe Lys Gly Asp Ser Gly Gly Pro Leu Val Cys Lys Asp Val Ala
            180                 185                 190

Gln Gly Ile Leu Ser Tyr Gly Asn Lys Lys Gly Thr Pro Pro Gly Val
            195                 200                 205

Tyr Ile Lys Val Ser His Phe Leu Pro Trp Ile Lys Arg Thr Met Lys
    210                 215                 220

Arg Leu
225

<210> SEQ ID NO 16
<211> LENGTH: 238
<212> TYPE: PRT
<213> ORGANISM: Homo sapiens

<400> SEQUENCE: 16

Ile Ile Gly Gly Lys Glu Val Ser Pro His Ser Arg Pro Phe Met Ala
  1               5                  10                  15

Ser Ile Gln Tyr Gly Gly His His Val Cys Gly Gly Val Leu Ile Asp
                 20                  25                  30

Pro Gln Trp Val Leu Thr Ala Ala His Cys Gln Tyr Arg Phe Thr Lys
             35                  40                  45

Gly Gln Ser Pro Thr Val Val Leu Gly Ala His Ser Leu Ser Lys Asn
 50                  55                  60

Glu Ala Ser Lys Gln Thr Leu Glu Ile Lys Lys Phe Ile Pro Phe Ser
 65                  70                  75                  80

Arg Val Thr Ser Asp Pro Gln Ser Asn Asp Ile Met Leu Val Lys Leu
                 85                  90                  95

Gln Thr Ala Ala Lys Leu Asn Lys His Val Lys Met Leu His Ile Arg
            100                 105                 110

Ser Lys Thr Ser Leu Arg Ser Gly Thr Lys Cys Lys Val Thr Gly Trp
            115                 120                 125

Gly Ala Thr Asp Pro Asp Ser Leu Arg Pro Ser Asp Thr Leu Arg Glu
    130                 135                 140

Val Thr Val Thr Val Leu Ser Arg Lys Leu Cys Asn Ser Gln Ser Tyr
145                 150                 155                 160

Tyr Asn Gly Asp Pro Phe Ile Thr Lys Asp Met Val Cys Ala Gly Asp
                165                 170                 175

Ala Lys Gly Gln Lys Asp Ser Cys Lys Gly Asp Ser Gly Gly Pro Leu
            180                 185                 190
```

Ile Cys Lys Gly Val Phe His Ala Ile Val Ser Gly Gly His Glu Cys
        195                 200                 205

Gly Val Ala Thr Lys Pro Gly Ile Tyr Thr Leu Leu Thr Lys Lys Tyr
        210                 215                 220

Gln Thr Trp Ile Lys Ser Asn Leu Val Pro Pro His Thr Asn
225                 230                 235

<210> SEQ ID NO 17
<211> LENGTH: 232
<212> TYPE: PRT
<213> ORGANISM: Homo sapiens

<400> SEQUENCE: 17

Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
                20                  25                  30

Pro Lys Trp Val Leu Thr Ala Ala His Cys Leu Ala Gln Arg Met Ala
            35                  40                  45

Gln Leu Arg Leu Val Leu Gly Leu His Thr Leu Asp Ser Pro Gly Leu
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
        115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
            180                 185                 190

Val Leu Ala Arg Val Leu Ser Phe Ser Ser Arg Val Cys Thr Asp Ile
        195                 200                 205

Phe Lys Pro Pro Val Ala Thr Ala Val Ala Pro Tyr Val Ser Trp Ile
    210                 215                 220

Arg Lys Val Thr Gly Arg Ser Ala
225                 230

<210> SEQ ID NO 18
<211> LENGTH: 235
<212> TYPE: PRT
<213> ORGANISM: Homo sapiens

<400> SEQUENCE: 18

Ile Ile Gly Gly Arg Glu Ser Arg Pro His Ser Arg Pro Tyr Met Ala
1               5                   10                  15

Tyr Leu Gln Ile Gln Ser Pro Ala Gly Gln Ser Arg Cys Gly Gly Phe
                20                  25                  30

Leu Val Arg Glu Asp Phe Val Leu Thr Ala Ala His Cys Trp Gly Ser
            35                  40                  45

Asn Ile Asn Val Thr Leu Gly Ala His Asn Ile Gln Arg Arg Glu Asn
            50                  55                  60

Thr Gln Gln His Ile Thr Ala Arg Arg Ala Ile Arg His Pro Gln Tyr
 65                  70                  75                  80

Asn Gln Arg Thr Ile Gln Asn Asp Ile Met Leu Leu Gln Leu Ser Arg
                 85                  90                  95

Arg Val Arg Arg Asn Arg Asn Val Asn Pro Val Ala Leu Pro Arg Ala
            100                 105                 110

Gln Glu Gly Leu Arg Pro Gly Thr Leu Cys Thr Val Ala Gly Trp Gly
                115                 120                 125

Arg Val Ser Met Arg Arg Gly Thr Asp Thr Leu Arg Glu Val Gln Leu
            130                 135                 140

Arg Val Gln Arg Asp Arg Gln Cys Leu Arg Ile Phe Gly Ser Tyr Asp
145                 150                 155                 160

Pro Arg Arg Gln Ile Cys Val Gly Asp Arg Arg Glu Arg Lys Ala Ala
                165                 170                 175

Phe Lys Gly Asp Ser Gly Gly Pro Leu Leu Cys Asn Asn Val Ala His
            180                 185                 190

Gly Ile Val Ser Tyr Gly Lys Ser Ser Gly Val Pro Pro Glu Val Phe
            195                 200                 205

Thr Arg Val Ser Ser Phe Leu Pro Trp Ile Arg Thr Thr Met Arg Ser
210                 215                 220

Phe Lys Leu Leu Asp Gln Met Glu Thr Pro Leu
225                 230                 235

<210> SEQ ID NO 19
<211> LENGTH: 226
<212> TYPE: PRT
<213> ORGANISM: Homo sapiens

<400> SEQUENCE: 19

Ile Ile Gly Gly Thr Glu Cys Lys Pro His Ser Arg Pro Tyr Met Ala
 1                   5                  10                  15

Tyr Leu Glu Ile Val Thr Ser Asn Gly Pro Ser Lys Phe Cys Gly Gly
                 20                  25                  30

Phe Leu Ile Arg Arg Asn Phe Val Leu Thr Ala Ala His Cys Ala Gly
             35                  40                  45

Arg Ser Ile Thr Val Thr Leu Gly Ala His Asn Ile Thr Glu Glu Glu
             50                  55                  60

Asp Thr Trp Gln Lys Leu Glu Val Ile Lys Gln Phe Arg His Pro Lys
 65                  70                  75                  80

Tyr Asn Thr Ser Thr Leu His His Asp Ile Met Leu Leu Lys Leu Lys
                 85                  90                  95

Glu Lys Ala Ser Leu Thr Leu Ala Val Gly Thr Leu Pro Phe Pro Ser
            100                 105                 110

Gln Phe Asn Phe Val Pro Pro Gly Arg Met Cys Arg Val Ala Gly Trp
            115                 120                 125

Gly Arg Thr Gly Val Leu Lys Pro Gly Ser Asp Thr Leu Gln Glu Val
            130                 135                 140

Lys Leu Arg Leu Met Asp Pro Gln Ala Cys Ser His Phe Arg Asp Phe
145                 150                 155                 160

Asp His Asn Leu Gln Leu Cys Val Gly Asn Pro Arg Lys Thr Lys Ser
                165                 170                 175

Ala Phe Lys Gly Asp Ser Gly Gly Pro Leu Leu Cys Ala Gly Val Ala

```
                180                 185                 190
Gln Gly Ile Val Ser Tyr Gly Arg Ser Asp Ala Lys Pro Pro Ala Val
            195                 200                 205

Phe Thr Arg Ile Ser His Tyr Arg Pro Trp Ile Asn Gln Ile Leu Gln
            210                 215                 220

Ala Asn
225

<210> SEQ ID NO 20
<211> LENGTH: 229
<212> TYPE: PRT
<213> ORGANISM: Homo sapiens

<400> SEQUENCE: 20

Ile Val Gly Gly His Glu Ala Gln Pro His Ser Arg Pro Tyr Met Ala
1               5                   10                  15

Ser Leu Gln Met Arg Gly Asn Pro Gly Ser His Phe Cys Gly Gly Thr
            20                  25                  30

Leu Ile His Pro Ser Phe Val Leu Thr Ala Ala His Cys Leu Arg Asp
        35                  40                  45

Ile Pro Gln Arg Leu Val Asn Val Val Leu Gly Ala His Asn Val Arg
    50                  55                  60

Thr Gln Glu Pro Thr Gln Gln His Phe Ser Val Ala Gln Val Phe Leu
65                  70                  75                  80

Asn Asn Tyr Asp Ala Glu Asn Lys Leu Asn Asp Val Leu Leu Ile Gln
                85                  90                  95

Leu Ser Ser Pro Ala Asn Leu Ser Ala Ser Val Ala Thr Val Gln Leu
            100                 105                 110

Pro Gln Gln Asp Gln Pro Val Pro His Gly Thr Gln Cys Leu Ala Met
        115                 120                 125

Gly Trp Gly Arg Val Gly Ala His Asp Pro Pro Ala Gln Val Leu Gln
130                 135                 140

Glu Leu Asn Val Thr Val Val Thr Phe Phe Cys Arg Pro His Asn Ile
145                 150                 155                 160

Cys Thr Phe Val Pro Arg Arg Lys Ala Gly Ile Cys Phe Gly Asp Ser
                165                 170                 175

Gly Gly Pro Leu Ile Cys Asp Gly Ile Ile Gln Gly Ile Asp Ser Phe
            180                 185                 190

Val Ile Trp Gly Cys Ala Thr Arg Leu Phe Pro Asp Phe Phe Thr Arg
        195                 200                 205

Val Ala Leu Tyr Val Asp Trp Ile Arg Ser Thr Leu Arg Arg Val Glu
    210                 215                 220

Ala Lys Gly Arg Pro
225

<210> SEQ ID NO 21
<211> LENGTH: 227
<212> TYPE: PRT
<213> ORGANISM: Homo sapiens

<400> SEQUENCE: 21

Ile Ile Gly Gly His Thr Cys Thr Arg Ser Ser Gln Pro Trp Gln Ala
1               5                   10                  15

Ala Leu Leu Ala Gly Pro Arg Arg Phe Leu Cys Gly Gly Ala Leu
            20                  25                  30

Leu Ser Gly Gln Trp Val Ile Thr Ala Ala His Cys Gly Arg Pro Ile
```

```
                 35                  40                  45
Leu Gln Val Ala Leu Gly Lys His Asn Leu Arg Arg Trp Glu Ala Thr
 50                  55                  60
Gln Gln Val Leu Arg Val Val Arg Gln Val Thr His Pro Asn Tyr Asn
 65                  70                  75                  80
Ser Arg Thr His Asp Asn Asp Leu Met Leu Gln Leu Gln Gln Pro
                 85                  90                  95
Ala Arg Ile Gly Arg Ala Val Arg Pro Ile Glu Val Thr Gln Ala Cys
                100                 105                 110
Ala Ser Pro Gly Thr Ser Cys Arg Val Ser Gly Trp Gly Thr Ile Ser
                115                 120                 125
Ser Pro Ile Ala Arg Tyr Pro Ala Ser Leu Gln Cys Val Asn Ile Asn
130                 135                 140
Ile Ser Pro Asp Glu Val Cys Gln Lys Ala Tyr Pro Arg Thr Ile Thr
145                 150                 155                 160
Pro Gly Met Val Cys Ala Gly Val Pro Gln Gly Gly Lys Asp Ser Cys
                165                 170                 175
Gln Gly Asp Ser Gly Gly Pro Leu Val Cys Arg Gly Gln Leu Gln Gly
                180                 185                 190
Leu Val Ser Trp Gly Met Glu Arg Cys Ala Leu Pro Gly Tyr Pro Gly
                195                 200                 205
Val Tyr Thr Asn Leu Cys Lys Tyr Arg Ser Trp Ile Glu Glu Thr Met
210                 215                 220
Arg Asp Lys
225

<210> SEQ ID NO 22
<211> LENGTH: 228
<212> TYPE: PRT
<213> ORGANISM: Homo sapiens

<400> SEQUENCE: 22

Ile Leu Gly Gly Arg Glu Ala Glu Ala His Ala Arg Pro Tyr Met Ala
  1                   5                  10                  15
Ser Val Gln Leu Asn Gly Ala His Leu Cys Gly Gly Val Leu Val Ala
                 20                  25                  30
Glu Gln Trp Val Leu Ser Ala Ala His Cys Leu Glu Asp Ala Ala Asp
                 35                  40                  45
Gly Lys Val Gln Val Leu Leu Gly Ala His Ser Leu Ser Gln Pro Glu
 50                  55                  60
Pro Ser Lys Arg Leu Tyr Asp Val Leu Arg Ala Val Pro His Pro Asp
 65                  70                  75                  80
Ser Gln Pro Asp Thr Ile Asp His Asp Leu Leu Leu Leu Gln Leu Ser
                 85                  90                  95
Glu Lys Ala Thr Leu Gly Pro Ala Val Arg Pro Leu Pro Trp Gln Arg
                100                 105                 110
Val Asp Arg Asp Val Ala Pro Gly Thr Leu Cys Asp Val Ala Gly Trp
                115                 120                 125
Gly Ile Val Asn His Ala Gly Arg Arg Pro Asp Ser Leu Gln His Val
130                 135                 140
Leu Leu Pro Val Leu Asp Arg Ala Thr Cys Asn Arg Arg Thr His His
145                 150                 155                 160
Asp Gly Ala Ile Thr Glu Arg Leu Met Cys Ala Glu Ser Asn Arg Arg
                165                 170                 175
```

```
Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
        195                 200                 205

Lys Pro Gly Ile Tyr Thr Arg Val Ala Ser Tyr Ala Ala Trp Ile Asp
    210                 215                 220

Ser Val Leu Ala
225

<210> SEQ ID NO 23
<211> LENGTH: 224
<212> TYPE: PRT
<213> ORGANISM: Homo sapiens

<400> SEQUENCE: 23

Ile Val Gly Gly Tyr Thr Cys Glu Glu Asn Ser Leu Pro Tyr Gln Val
1               5                   10                  15

Ser Leu Asn Ser Gly Ser His Phe Cys Gly Gly Ser Leu Ile Ser Glu
            20                  25                  30

Gln Trp Val Val Ser Ala Ala His Cys Tyr Lys Thr Arg Ile Gln Val
        35                  40                  45

Arg Leu Gly Glu His Asn Ile Lys Val Leu Glu Gly Asn Glu Gln Phe
50                  55                  60

Ile Asn Ala Ala Lys Ile Ile Arg His Pro Gln Tyr Asp Arg Lys Thr
65                  70                  75                  80

Leu Asn Asn Asp Ile Met Leu Ile Lys Leu Ser Ser Arg Ala Val Ile
                85                  90                  95

Asn Ala Arg Val Ser Thr Ile Ser Leu Pro Thr Ala Pro Pro Ala Thr
            100                 105                 110

Gly Thr Lys Cys Leu Ile Ser Gly Trp Gly Asn Thr Ala Ser Ser Gly
        115                 120                 125

Ala Asp Tyr Pro Asp Glu Leu Gln Cys Leu Asp Ala Pro Val Leu Ser
130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Val Val Ser
            180                 185                 190

Trp Gly Asp Gly Cys Ala Gln Lys Asn Lys Pro Gly Val Tyr Thr Lys
        195                 200                 205

Val Tyr Asn Tyr Val Lys Trp Ile Lys Asn Thr Ile Ala Ala Asn Ser
210                 215                 220

<210> SEQ ID NO 24
<211> LENGTH: 224
<212> TYPE: PRT
<213> ORGANISM: Homo sapiens

<400> SEQUENCE: 24

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Lys Ser Arg Ile Gln Val
        35                  40                  45
```

-continued

```
Arg Leu Gly Glu His Asn Ile Glu Val Leu Glu Gly Asn Glu Gln Phe
 50                  55                  60

Ile Asn Ala Ala Lys Ile Ile Arg His Pro Gln Tyr Asp Arg Lys Thr
 65                  70                  75                  80

Leu Asn Asn Asp Ile Met Leu Ile Lys Leu Ser Ser Arg Ala Val Ile
                     85                  90                  95

Asn Ala Arg Val Ser Thr Ile Ser Leu Pro Thr Ala Pro Pro Ala Thr
                100                 105                 110

Gly Thr Lys Cys Leu Ile Ser Gly Trp Gly Asn Thr Ala Ser Ser Gly
                115                 120                 125

Ala Asp Tyr Pro Asp Glu Leu Gln Cys Leu Asp Ala Pro Val Leu Ser
130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                    165                 170                 175

Ser Gly Gly Pro Val Val Cys Asn Gly Gln Leu Gln Gly Val Val Ser
                180                 185                 190

Trp Gly Asp Gly Cys Ala Gln Lys Asn Lys Pro Gly Val Tyr Thr Lys
                195                 200                 205

Val Tyr Asn Tyr Val Lys Trp Ile Lys Asn Thr Ile Ala Ala Asn Ser
210                 215                 220

<210> SEQ ID NO 25
<211> LENGTH: 250
<212> TYPE: PRT
<213> ORGANISM: Homo sapiens

<400> SEQUENCE: 25

Ile Ile Gly Gly His Glu Val Thr Pro His Ser Arg Pro Tyr Met Ala
 1               5                  10                  15

Ser Val Arg Phe Gly Gly Gln His His Cys Gly Gly Phe Leu Leu Arg
                 20                  25                  30

Ala Arg Trp Val Val Ser Ala Ala His Cys Phe Ser His Arg Asp Leu
                 35                  40                  45

Arg Thr Gly Leu Val Val Leu Gly Ala His Val Leu Ser Thr Ala Glu
 50                  55                  60

Pro Thr Gln Gln Val Phe Gly Ile Asp Ala Leu Thr Thr His Pro Asp
 65                  70                  75                  80

Tyr His Pro Met Thr His Ala Asn Asp Ile Cys Leu Leu Arg Leu Asn
                     85                  90                  95

Gly Ser Ala Val Leu Gly Pro Ala Val Gly Leu Leu Arg Pro Pro Gly
                100                 105                 110

Arg Arg Ala Arg Pro Pro Thr Ala Gly Thr Arg Cys Arg Val Ala Gly
                115                 120                 125

Trp Gly Phe Val Ser Asp Phe Glu Glu Leu Pro Pro Gly Leu Met Glu
130                 135                 140

Ala Lys Val Arg Val Leu Asp Pro Asp Val Cys Asn Ser Ser Trp Lys
145                 150                 155                 160

Gly His Leu Thr Leu Thr Met Leu Cys Thr Arg Ser Gly Asp Ser His
                    165                 170                 175

Arg Arg Gly Phe Cys Ser Ala Asp Ser Gly Gly Pro Leu Val Cys Arg
                180                 185                 190

Asn Arg Ala His Gly Leu Val Ser Phe Ser Gly Leu Trp Cys Gly Asp
                195                 200                 205
```

Pro Lys Thr Pro Asp Val Tyr Thr Gln Val Ser Ala Phe Val Ala Trp
    210                 215                 220

Ile Trp Asp Val Val Arg Arg Ser Ser Pro Gln Pro Gly Pro Leu Pro
225                 230                 235                 240

Gly Thr Thr Arg Pro Pro Gly Glu Ala Ala
                245                 250

<210> SEQ ID NO 26
<211> LENGTH: 250
<212> TYPE: PRT
<213> ORGANISM: Homo sapiens

<400> SEQUENCE: 26

Ile Ile Gly Gly His Glu Val Thr Pro His Ser Arg Pro Tyr Met Ala
1               5                   10                  15

Ser Val Arg Phe Gly Gly Gln His His Cys Gly Gly Phe Leu Leu Arg
                20                  25                  30

Ala Arg Trp Val Val Ser Ala Ala His Cys Phe Ser His Arg Asp Leu
            35                  40                  45

Arg Thr Gly Leu Val Val Leu Gly Ala His Val Leu Ser Thr Ala Glu
    50                  55                  60

Pro Thr Gln Gln Val Phe Gly Ile Asp Ala Leu Thr Thr His Pro Asp
65                  70                  75                  80

Tyr His Pro Met Thr His Ala Asn Asp Ile Cys Leu Leu Arg Leu Asn
                85                  90                  95

Gly Ser Ala Val Leu Gly Pro Ala Val Gly Leu Leu Arg Leu Pro Gly
            100                 105                 110

Arg Arg Ala Arg Pro Pro Thr Ala Gly Thr Arg Cys Arg Val Ala Gly
        115                 120                 125

Trp Gly Phe Val Ser Asp Phe Glu Glu Leu Pro Pro Gly Leu Met Glu
130                 135                 140

Ala Lys Val Arg Val Leu Asp Pro Asp Val Phe Asn Ser Ser Trp Lys
145                 150                 155                 160

Gly His Leu Thr Leu Thr Met Leu Cys Thr Arg Ser Gly Asp Ser His
                165                 170                 175

Arg Arg Gly Phe Cys Ser Ala Asp Ser Gly Gly Pro Leu Val Cys Arg
            180                 185                 190

Asn Arg Ala His Gly Leu Val Ser Phe Ser Gly Leu Trp Cys Gly Asp
        195                 200                 205

Pro Lys Thr Pro Asp Val Tyr Thr Gln Val Ser Ala Phe Val Ala Trp
    210                 215                 220

Ile Trp Asp Val Val Arg Arg Ser Ser Pro Gln Pro Gly Pro Leu Pro
225                 230                 235                 240

Gly Thr Thr Arg Pro Pro Gly Glu Ala Ala
                245                 250

<210> SEQ ID NO 27
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 27

Gly Arg Lys Lys Arg Arg Gln Arg Arg Arg Pro Pro Gln
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 28

Arg Gln Ile Lys Ile Trp Phe Gln Asn Arg Arg Met Lys Trp Lys Lys
1               5                   10                  15

<210> SEQ ID NO 29
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 29

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 30
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 30

Thr Lys Ile Glu Ser Leu Lys Glu His Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 31

Thr Gln Ile Glu Asn Leu Lys Glu Lys Gly
1               5                   10

<210> SEQ ID NO 32
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 32

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic polypeptide

```
<400> SEQUENCE: 33

Gly Leu Phe Glu Ala Ile Glu Gly Phe Ile Glu Asn Gly Trp Glu Gly
1               5                   10                  15
Met Ile Glu Gly Trp Tyr Gly Cys Gly
            20                  25

<210> SEQ ID NO 34
<211> LENGTH: 18
<212> TYPE: PRT
<213> ORGANISM: Artificial Sequence
<220> FEATURE:
<223> OTHER INFORMATION: Synthetic peptide

<400> SEQUENCE: 34

Gly Ser Thr Ser Gly Ser Gly Lys Pro Gly Ser Gly Glu Gly Ser Thr
1               5                   10                  15
Lys Gly

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide

<400> SEQUENCE: 35

Glu Ala Ala Ala Lys
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide

<400> SEQUENCE: 36

Gly Gly Gly Gly Ser
1               5

<210> SEQ ID NO 37
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 37

Gly Ser Thr Ser Gly Ser Gly Lys Pro Gly Ser Gly Gln Gly Ser Thr
1               5                   10                  15
Lys Gly

<210> SEQ ID NO 38
<211> LENGTH: 8
<212> TYPE: PRT
<213> ORGANISM: Artificial sequence
<220> FEATURE:
<223> OTHER INFORMATION: Synthetic peptide

<400> SEQUENCE: 38

Ile Ile Gly Gly His Glu Ala Lys
1               5

<210> SEQ ID NO 39
```

<211> LENGTH: 14
<212> TYPE: PRT
<213> ORGANISM: Artificial sequence
<220> FEATURE:
<223> OTHER INFORMATION: Synthetic peptide

<400> SEQUENCE: 39

Tyr Val Asp Glu Val Asp Ile Ile Gly Gly His Glu Ala Lys
1               5                   10

<210> SEQ ID NO 40
<211> LENGTH: 12
<212> TYPE: PRT
<213> ORGANISM: Artificial sequence
<220> FEATURE:
<223> OTHER INFORMATION: Synthetic peptide

<400> SEQUENCE: 40

Arg Val Arg Arg Ile Ile Gly Gly His Glu Ala Lys
1               5                   10

<210> SEQ ID NO 41
<211> LENGTH: 12
<212> TYPE: PRT
<213> ORGANISM: Artificial sequence
<220> FEATURE:
<223> OTHER INFORMATION: Synthetic peptide

<400> SEQUENCE: 41

Arg Val Arg Arg Ile Ile Gly Gly His Glu Ala Lys
1               5                   10

<210> SEQ ID NO 42
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X = I or A
<220> FEATURE:
<221> NAME/KEY: MISC_FEATURE
<222> LOCATION: (2)..(2)
<223> OTHER INFORMATION: X = E or D

<400> SEQUENCE: 42

Xaa Xaa Gly Arg Ile Ile Gly Gly His Glu Ala Lys
1               5                   10

<210> SEQ ID NO 43
<211> LENGTH: 12
<212> TYPE: PRT
<213> ORGANISM: Artificial sequence
<220> FEATURE:
<223> OTHER INFORMATION: Synthetic peptide

<400> SEQUENCE: 43

Tyr Glu Val Asp Ile Ile Gly Gly His Glu Ala Lys
1               5                   10

<210> SEQ ID NO 44
<211> LENGTH: 12
<212> TYPE: PRT
<213> ORGANISM: Artificial sequence
<220> FEATURE:
<223> OTHER INFORMATION: Synthetic peptide

```
<400> SEQUENCE: 44

Trp Glu His Asp Ile Ile Gly Gly His Glu Ala Lys
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic peptide

<400> SEQUENCE: 45

Asp Val Ala Asp Ile Ile Gly Gly His Glu Ala Lys
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Asp Glu His Asp Ile Ile Gly Gly His Glu Ala Lys
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic peptide

<400> SEQUENCE: 47

Asp Glu Val Asp Ile Ile Gly Gly His Glu Ala Lys
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide

<400> SEQUENCE: 48

Asp Met Gln Asp Ile Ile Gly Gly His Glu Ala Lys
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Leu Glu Val Asp Ile Ile Gly Gly His Glu Ala Lys
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide

<400> SEQUENCE: 50
```

```
Leu Glu His Asp Ile Ile Gly Gly His Glu Ala Lys
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic peptide

<400> SEQUENCE: 51

Val Glu Ile Asp Ile Ile Gly Gly His Glu Ala Lys
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Val Glu His Asp Ile Ile Gly Gly His Glu Ala Lys
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide

<400> SEQUENCE: 53

Ile Glu Thr Asp Ile Ile Gly Gly His Glu Ala Lys
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Leu Glu Thr Asp Ile Ile Gly Gly His Glu Ala Lys
1               5                   10

<210> SEQ ID NO 55
<211> LENGTH: 12
<212> TYPE: PRT
<213> ORGANISM: Artificial sequence
<220> FEATURE:
<223> OTHER INFORMATION: Synthetic peptide

<400> SEQUENCE: 55

Ile Glu Ala Asp Ile Ile Gly Gly His Glu Ala Lys
1               5                   10

<210> SEQ ID NO 56
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
```

```
<223> OTHER INFORMATION: Xaa can be any naturally occurring amino acid

<400> SEQUENCE: 56

Leu Pro Xaa Thr
1

<210> SEQ ID NO 57
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 57

Ser Pro Xaa Thr
1

<210> SEQ ID NO 58
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 58

Leu Ala Xaa Thr
1

<210> SEQ ID NO 59
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 59

Leu Ser Xaa Thr
1

<210> SEQ ID NO 60
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 60

Asn Pro Xaa Thr
1

<210> SEQ ID NO 61
<211> LENGTH: 4
<212> TYPE: PRT
```

```
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 61

Val Pro Xaa Thr
1

<210> SEQ ID NO 62
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 62

Ile Pro Xaa Thr
1

<210> SEQ ID NO 63
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 63

Tyr Pro Xaa Arg
1

<210> SEQ ID NO 64
<211> LENGTH: 5
<212> TYPE: PRT
<213> ORGANISM: Artificial sequence
<220> FEATURE:
<223> OTHER INFORMATION: Synthetic peptide

<400> SEQUENCE: 64

Leu Pro Ala Thr Gly
1               5

<210> SEQ ID NO 65
<211> LENGTH: 5
<212> TYPE: PRT
<213> ORGANISM: Artificial sequence
<220> FEATURE:
<223> OTHER INFORMATION: Synthetic peptide

<400> SEQUENCE: 65

Leu Pro Asn Thr Gly
1               5

<210> SEQ ID NO 66
<211> LENGTH: 5
<212> TYPE: PRT
<213> ORGANISM: Artificial sequence
<220> FEATURE:
```

```
<223> OTHER INFORMATION: Synthetic peptide

<400> SEQUENCE: 66

Leu Pro Glu Thr Gly
1               5

<210> SEQ ID NO 67
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 67

Leu Pro Xaa Ala Gly
1               5

<210> SEQ ID NO 68
<211> LENGTH: 5
<212> TYPE: PRT
<213> ORGANISM: Artificial sequence
<220> FEATURE:
<223> OTHER INFORMATION: Synthetic peptide

<400> SEQUENCE: 68

Leu Pro Asn Ala Gly
1               5

<210> SEQ ID NO 69
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 69

Leu Pro Xaa Thr Ala
1               5

<210> SEQ ID NO 70
<211> LENGTH: 5
<212> TYPE: PRT
<213> ORGANISM: Artificial sequence
<220> FEATURE:
<223> OTHER INFORMATION: Synthetic peptide

<400> SEQUENCE: 70

Leu Pro Asn Thr Ala
1               5

<210> SEQ ID NO 71
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
```

```
<400> SEQUENCE: 71

Leu Gly Xaa Thr Gly
1               5

<210> SEQ ID NO 72
<211> LENGTH: 5
<212> TYPE: PRT
<213> ORGANISM: Artificial sequence
<220> FEATURE:
<223> OTHER INFORMATION: Synthetic peptide

<400> SEQUENCE: 72

Leu Gly Ala Thr Gly
1               5

<210> SEQ ID NO 73
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 73

Ile Pro Xaa Thr Gly
1               5

<210> SEQ ID NO 74
<211> LENGTH: 5
<212> TYPE: PRT
<213> ORGANISM: Artificial sequence
<220> FEATURE:
<223> OTHER INFORMATION: Synthetic peptide

<400> SEQUENCE: 74

Ile Pro Asn Thr Gly
1               5

<210> SEQ ID NO 75
<211> LENGTH: 5
<212> TYPE: PRT
<213> ORGANISM: Artificial sequence
<220> FEATURE:
<223> OTHER INFORMATION: Synthetic peptide

<400> SEQUENCE: 75

Ile Pro Glu Thr Gly
1               5

<210> SEQ ID NO 76
<211> LENGTH: 6
<212> TYPE: PRT
<213> ORGANISM: Artificial sequence
<220> FEATURE:
<223> OTHER INFORMATION: Synthetic peptide

<400> SEQUENCE: 76

Leu Pro Lys Thr Gly Gly
1               5

<210> SEQ ID NO 77
<211> LENGTH: 6
<212> TYPE: PRT
<213> ORGANISM: Artificial sequence
```

```
<220> FEATURE:
<223> OTHER INFORMATION: Synthetic peptide

<400> SEQUENCE: 77

Leu Pro Ala Thr Gly Gly
1               5

<210> SEQ ID NO 78
<211> LENGTH: 6
<212> TYPE: PRT
<213> ORGANISM: Artificial sequence
<220> FEATURE:
<223> OTHER INFORMATION: Synthetic peptide

<400> SEQUENCE: 78

Leu Pro Asn Thr Gly Gly
1               5

<210> SEQ ID NO 79
<211> LENGTH: 6
<212> TYPE: PRT
<213> ORGANISM: Artificial sequence
<220> FEATURE:
<223> OTHER INFORMATION: Synthetic peptide

<400> SEQUENCE: 79

Leu Pro Glu Thr Gly Gly
1               5

<210> SEQ ID NO 80
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 80

Leu Pro Xaa Ala Gly Gly
1               5

<210> SEQ ID NO 81
<211> LENGTH: 6
<212> TYPE: PRT
<213> ORGANISM: Artificial sequence
<220> FEATURE:
<223> OTHER INFORMATION: Synthetic peptide

<400> SEQUENCE: 81

Leu Pro Asn Ala Gly Gly
1               5

<210> SEQ ID NO 82
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 82

Leu Pro Xaa Thr Ala Gly
```

```
<210> SEQ ID NO 83
<211> LENGTH: 6
<212> TYPE: PRT
<213> ORGANISM: Artificial sequence
<220> FEATURE:
<223> OTHER INFORMATION: Synthetic peptide

<400> SEQUENCE: 83

Leu Pro Asn Thr Ala Gly
1               5

<210> SEQ ID NO 84
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 84

Leu Gly Xaa Thr Gly Gly
1               5

<210> SEQ ID NO 85
<211> LENGTH: 6
<212> TYPE: PRT
<213> ORGANISM: Artificial sequence
<220> FEATURE:
<223> OTHER INFORMATION: Synthetic peptide

<400> SEQUENCE: 85

Leu Gly Ala Thr Gly Gly
1               5

<210> SEQ ID NO 86
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 86

Ile Pro Xaa Thr Gly Gly
1               5

<210> SEQ ID NO 87
<211> LENGTH: 6
<212> TYPE: PRT
<213> ORGANISM: Artificial sequence
<220> FEATURE:
<223> OTHER INFORMATION: Synthetic peptide

<400> SEQUENCE: 87

Ile Pro Asn Thr Gly Gly
1               5

<210> SEQ ID NO 88
<211> LENGTH: 6
<212> TYPE: PRT
```

```
<213> ORGANISM: Artificial sequence
<220> FEATURE:
<223> OTHER INFORMATION: Synthetic peptide

<400> SEQUENCE: 88

Ile Pro Glu Thr Gly Gly
1               5

<210> SEQ ID NO 89
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 89

Leu Pro Xaa Thr Gly Gly
1               5

<210> SEQ ID NO 90
<211> LENGTH: 5
<212> TYPE: PRT
<213> ORGANISM: Artificial sequence
<220> FEATURE:
<223> OTHER INFORMATION: Synthetic peptide

<400> SEQUENCE: 90

Leu Pro Lys Thr Gly
1               5

<210> SEQ ID NO 91
<211> LENGTH: 4
<212> TYPE: PRT
<213> ORGANISM: Artificial sequence
<220> FEATURE:
<223> OTHER INFORMATION: Synthetic peptide

<400> SEQUENCE: 91

Ile Ile Gly Gly
1

<210> SEQ ID NO 92
<211> LENGTH: 4
<212> TYPE: PRT
<213> ORGANISM: Artificial sequence
<220> FEATURE:
<223> OTHER INFORMATION: Synthetic peptide

<400> SEQUENCE: 92

Ile Val Gly Gly
1

<210> SEQ ID NO 93
<211> LENGTH: 4
<212> TYPE: PRT
<213> ORGANISM: Artificial sequence
<220> FEATURE:
<223> OTHER INFORMATION: Synthetic peptide

<400> SEQUENCE: 93

Ile Leu Gly Gly
1
```

```
<210> SEQ ID NO 94
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 94

Leu Pro Xaa Thr Gly
1               5

<210> SEQ ID NO 95
<211> LENGTH: 7
<212> TYPE: PRT
<213> ORGANISM: Artificial sequence
<220> FEATURE:
<223> OTHER INFORMATION: Synthetic peptide

<400> SEQUENCE: 95

Leu Pro Glu Thr Gly Gly Gly
1               5

<210> SEQ ID NO 96
<211> LENGTH: 4
<212> TYPE: PRT
<213> ORGANISM: Artificial Sequence
<220> FEATURE:
<223> OTHER INFORMATION: Synthetic peptide

<400> SEQUENCE: 96

Tyr Glu Val Asp
1

<210> SEQ ID NO 97
<211> LENGTH: 4
<212> TYPE: PRT
<213> ORGANISM: Artificial Sequence
<220> FEATURE:
<223> OTHER INFORMATION: Synthetic peptide

<400> SEQUENCE: 97

Trp Glu His Asp
1

<210> SEQ ID NO 98
<211> LENGTH: 4
<212> TYPE: PRT
<213> ORGANISM: Artificial Sequence
<220> FEATURE:
<223> OTHER INFORMATION: Synthetic peptide

<400> SEQUENCE: 98

Asp Val Ala Asp
1

<210> SEQ ID NO 99
<211> LENGTH: 4
<212> TYPE: PRT
<213> ORGANISM: Artificial Sequence
<220> FEATURE:
<223> OTHER INFORMATION: Synthetic peptide

<400> SEQUENCE: 99

Asp Glu His Asp
```

```
<210> SEQ ID NO 100
<211> LENGTH: 4
<212> TYPE: PRT
<213> ORGANISM: Artificial Sequence
<220> FEATURE:
<223> OTHER INFORMATION: Synthetic peptide

<400> SEQUENCE: 100

Asp Glu Val Asp
1

<210> SEQ ID NO 101
<211> LENGTH: 4
<212> TYPE: PRT
<213> ORGANISM: Artificial Sequence
<220> FEATURE:
<223> OTHER INFORMATION: Synthetic peptide

<400> SEQUENCE: 101

Asp Met Gln Asp
1

<210> SEQ ID NO 102
<211> LENGTH: 4
<212> TYPE: PRT
<213> ORGANISM: Artificial Sequence
<220> FEATURE:
<223> OTHER INFORMATION: Synthetic peptide

<400> SEQUENCE: 102

Leu Glu Val Asp
1

<210> SEQ ID NO 103
<211> LENGTH: 4
<212> TYPE: PRT
<213> ORGANISM: Artificial Sequence
<220> FEATURE:
<223> OTHER INFORMATION: Synthetic peptide

<400> SEQUENCE: 103

Leu Glu His Asp
1

<210> SEQ ID NO 104
<211> LENGTH: 4
<212> TYPE: PRT
<213> ORGANISM: Artificial Sequence
<220> FEATURE:
<223> OTHER INFORMATION: Synthetic peptide

<400> SEQUENCE: 104

Val Glu Ile Asp
1

<210> SEQ ID NO 105
<211> LENGTH: 4
<212> TYPE: PRT
<213> ORGANISM: Artificial Sequence
<220> FEATURE:
<223> OTHER INFORMATION: Synthetic peptide

<400> SEQUENCE: 105

Val Glu His Asp
1
```

```
<210> SEQ ID NO 106
<211> LENGTH: 4
<212> TYPE: PRT
<213> ORGANISM: Artificial Sequence
<220> FEATURE:
<223> OTHER INFORMATION: Synthetic peptide

<400> SEQUENCE: 106

Ile Glu Thr Asp
1

<210> SEQ ID NO 107
<211> LENGTH: 4
<212> TYPE: PRT
<213> ORGANISM: Artificial Sequence
<220> FEATURE:
<223> OTHER INFORMATION: Synthetic peptide

<400> SEQUENCE: 107

Leu Glu Thr Asp
1

<210> SEQ ID NO 108
<211> LENGTH: 4
<212> TYPE: PRT
<213> ORGANISM: Artificial Sequence
<220> FEATURE:
<223> OTHER INFORMATION: Synthetic peptide

<400> SEQUENCE: 108

Ile Glu Ala Asp
1

<210> SEQ ID NO 109
<211> LENGTH: 4
<212> TYPE: PRT
<213> ORGANISM: Artificial Sequence
<220> FEATURE:
<223> OTHER INFORMATION: Synthetic peptide

<400> SEQUENCE: 109

Arg Val Arg Arg
1

<210> SEQ ID NO 110
<211> LENGTH: 4
<212> TYPE: PRT
<213> ORGANISM: Artificial Sequence
<220> FEATURE:
<223> OTHER INFORMATION: Synthetic peptide

<400> SEQUENCE: 110

Ile Glu Pro Asp
1
```

CELL-TARGETED CYTOTOXIC CONSTRUCTS

The present application is a continuation of U.S. application Ser. No. 15/434,648, filed Feb. 16, 2017, now U.S. Pat. No. 11,193,117, which claims the priority benefit of U.S. Provisional Application No. 62/295,636, filed Feb. 16, 2016, the entire contents of each of which are hereby incorporated by reference.

BACKGROUND OF THE INVENTION

1. Field of the Invention

The present invention relates generally to the field of molecular biology and recombinant protein production. More particularly, it concerns the linkage of cytotoxic agents, such as serine protease polypeptides (e.g., granzymes) to cell-targeting moieties.

2. Description of Related Art

The successful development of targeted therapeutics (e.g., for cancer applications) depends on the identification of ligands and antigens specific for target cells, generation of molecules capable of targeting those components specifically and, finally, use of highly toxic molecules for killing of target cells. Immunoconjugates composed of antibodies and small, toxic drugs or radioisotopes have been successfully tested in vitro, in animal models and have demonstrated activity in the clinical setting. In addition to the use of small molecules for the toxin component, a number of highly cytotoxic protein components, such as diphtheria toxin, ricin A-chain, Pseudomonas exotoxin, and gelonin (rGel), have been used for targeted therapies. However, problems such as capillary leak syndrome, immunogenicity and inadvertent toxicity (to non-targeted cells) continue to limit implementation of successful therapy, especially for long-term or chronic applications. Thus, there remains a need for highly specific and highly active toxin molecules and cell-targeting constructs comprising such molecules.

SUMMARY OF THE INVENTION

Certain embodiments of the present disclosure concern compositions produced using a sortase reaction. In one embodiment, there is provided a compound comprising a cytotoxic agent conjugated to a sortase recognition sequence.

In some aspects, the cytotoxic agent is a cytotoxic polypeptide, such as a serine protease. Thus, in some aspects, the present disclosure concerns sortase serine protease polypeptides and fusion proteins comprising such sortase serine proteases. In some aspects, a sortase serine protease polypeptide is conjugated to, or fused with, a cell targeting moiety to provide a cell-targeted cytotoxic construct. Such constructs can be used, for example, in the treatment of cell proliferative diseases, such as cancer.

In certain aspects, the serine protease is granzyme B, granzyme A, granzyme H, granzyme K, granzyme M, Cathepsin G, Chymase, Myeloblastin, Kallikrein-14, Complement factor D, PRSS3 protein, Trypsin-1, Serine protease 57 or PRSSL1 protein. In particular aspects, the serine protease is Granzyme B (GrB).

In some aspects, the serine protease is a truncated serine protease having an IIGG (SEQ ID NO:91), IVGG (SEQ ID NO:92) or ILGG (SEQ ID NO:93) at its N-terminus. In certain aspects, the GrB polypeptide comprises an amino acid substitution or deletion at one or more positions selected from the group consisting of Asp 37, Asn 51, Asn 84, Arg 96, Arg 100, Arg 102, Asp 150, Arg 201, Cys 210, Lys 221, Lys 222, Lys 225, or Arg 226.

In some aspects, the cytotoxic agent is a chemotherapeutic or a toxin, such as auristatin, particularly monomethyl-auristatin E (MMAE). In specific aspects, the MMAE comprises a protease-cleavable linker, such as citrulline-valine.

In some aspects, the sortase recognition sequence is a C-terminal sortase donor sequence or an N-terminal sortase acceptor sequence. In certain aspects, the C-terminal sortase donor sequence is LPXT(G). (SEQ ID NO:94) such as LPETGG (SEQ ID NO: 79). In some aspects, the N-terminal sortase acceptor sequence is a poly-glycine sequence, such as GGG.

In additional aspects, the compound further comprises at least one spacer positioned between the serine protease and sortase recognition sequence. In particular aspects, the compound comprises two spacers. In certain aspects, the spacer comprises the $G_4S$ (GGGGS; SEQ ID NO: 36) sequence. In other aspects, the compound does not comprise a spacer.

In certain aspects, the cytotoxic agent is granzyme B and the polypeptide comprises a coding sequence at least 90% identical to SEQ ID NO: 2. In some aspects, the polypeptide comprises a coding sequence at least 95%, 98%, or 99% identical to SEQ ID NO: 2.

In some aspects, the compound is conjugated to or fused with a cell-targeting moiety. In certain aspects, the cell-targeting moiety comprises sortase recognition sequence, such as a C-terminal sortase donor sequence or an N-terminal sortase acceptor sequence. In some aspects, the C-terminal sortase donor sequence is $LPXT(G)_n$, (SEQ ID NO:94) such as LPETGG (SEQ ID NO:79). In certain aspects, the N-terminal sortase recognition sequence comprises 1 to 10 glycine residues. For example, the N-terminal sortase recognition sequence is GGG. In some aspects, the compound is fused with a cell-targeting moiety positioned C-terminally relative to the cytotoxic agent, such as serine protease. In other aspects, the compound is fused with a cell-targeting moiety positioned N-terminally relative to the cytotoxic agent, such as small molecule cytotoxic agents or certain types of serine proteases.

In some aspects, the cell-targeting moiety is a peptide or polypeptide. In certain aspects, the cell-targeting moiety is a polynucleotide. For example, the polynucleotide is RNA or DNA.

In certain aspects, the cell-targeting moiety is an antibody. In some aspects, the antibody is a monoclonal, chimeric antibody, Fab', Fab, F(ab')2, single domain antibody, Fv, single chain Fv (scFv) antibody or VHH nanobody. In certain aspects, the antibody is a human antibody, a humanized antibody or a deimmunized antibody. For example, the antibody is a 15A8, ZME-018, ScFvMEL, cetuximab or trastuzumab antibody.

In some aspects, the cell-targeting moiety binds to a protein, carbohydrate or lipid expressed on cancer cells. For example, the cell-targeting moiety binds to FN14 receptor, VEGFR, GP240, 5T4, HER1, HER2, CD-33, CD-38, fltl, Flk-1, CEA, FGFR3, IGFBP2 or IGF-1R. In some aspects, the cell-targeting moiety is Yoked chorionic gonadotropin (YCG).

In some aspects, the cytotoxic agent or cell-targeting moiety is further conjugated to an imaging agent. For example, the imaging agent can be a radionuclide, a MRI contrast agent or an ultrasound contrast agent. Thus, in some aspects, a method is provided for imaging target cells in a subject comprising administering a cell-targeting compound conjugated to an imaging agent to the subject and imaging the target cells in the subject.

In a further embodiment, there is provided a recombinant fusion polypeptide comprising: (a) a recombinant cytotoxic polypeptide; (b) a sortase linker and (c) a cell-targeting polypeptide, wherein the sortase linker is positioned between the cytotoxic polypeptide and the cell-targeting polypeptide. As used herein the term "sortase linker" refers to the residual sequence after the linkage of two polypeptides by a sortase reaction the LPXT (SEQ ID NO:56) from the C-terminal sortase donor sequence and the G or poly-G (Ge) from the N-terminal sortase recognition sequence. Thus, a sortase linker can comprise the sequence LPXT(G)$_n$. (SEQ ID NO:94) In certain aspects, the recombinant cytotoxic polypeptide is a recombinant serine protease. In some aspects, the recombinant serine protease is a truncated serine protease having an IIGG (SEQ ID NO:91), IVGG (SEQ ID NO:92) or ILGG (SEQ ID NO:93) at its N-terminus.

In some aspects, the serine protease polypeptide is a GrB polypeptide. In other aspects, the GrB polypeptide comprises an amino acid substitution or deletion at one or more positions selected from the group consisting of Asp 37, Asn 51, Asn 84, Arg 96, Arg 100, Arg 102, Asp 150, Arg 201, Cys 210, Lys 221, Lys 222, Lys 225, or Arg 226. In some aspects, the amino acid substitution is for a residue having a polar or positively charged side chain. In certain aspects, the polypeptide further comprises an amino acid sequence comprising a Cys, wherein the amino acid sequence is positioned C-terminally relative to the GrB coding sequence.

In some aspects, the sortase linker has the sequence motif LPXT(G). (SEQ ID NO:94) or other sequence motif recognized by a sortase. For example, the sortase linker comprises the sequence LPETGGG (SEQ ID NO:95).

In certain aspects, the polypeptide comprises from N-terminus to C-terminus a recombinant GrB polypeptide; a sortase linker; and a Yoked chorionic gonadotropin (YCG) polypeptide in which the beta and alpha chains are fused together to form a single polypeptide. In other aspects the polypeptide comprises a GrB linked by sortase to a Yoked chorionic gonadotropin in which the alpha chain is N-terminal to the beta chain. In other aspects, the polypeptide is linked by sortase to a polypeptide consisting of the beta chain of any gonadotropin and the alpha chain of human chorionic gonadotropin.

In another embodiment, there is provided a method of producing a targeted compound comprising: (a) obtaining a compound comprising a cytotoxic agent as provided herein and a cell-targeting moiety comprising a sortase recognition sequence; and (b) contacting the compound and cell-targeting moiety with a transpeptidase, thereby producing the targeted compound. In some aspects, the transpeptidase is Sortase A. In certain aspects, the compound, cell-targeting moiety, and transpeptidase are present at a ratio of about 1:1:3 to about 1:1:6, such as about 1:1:5.

In some aspects, the compound comprises an N-terminal sortase acceptor sequence and the cell-targeting moiety comprises a C-terminal sortase donor sequence. In other aspects, the compound comprises an C-terminal sortase donor sequence and the cell-targeting moiety comprises an N-terminal sortase acceptor sequence. In certain aspects, the C-terminal sortase donor sequence is LPXT(G)$_n$. (SEQ ID NO: 94) such as LPETGG (SEQ ID NO:79). In certain aspects, the N-terminal sortase acceptor sequence comprises 1 to 10 N-terminal glycine residues. For example, the N-terminal sortase acceptor sequence comprises 3 N-terminal glycine residues.

In some aspects, the cell-targeting moiety is a peptide or polypeptide. In certain aspects, the cell-targeting moiety is a polynucleotide. For example, the polynucleotide is RNA or DNA. In some aspects, the RNA is siRNA, miRNA or shRNA. In other aspects, the cell-targeting moiety comprises a short peptide with an N-terminal triglycine sequence conjugated to a polynucleotide.

A further embodiment provides a composition comprising the compound provided herein comprising: (a) a cytotoxic agent, such as a serine protease polypeptide; (b) a sortase linker; and (c) a cell-targeting moiety, such as a polypeptide, in a pharmaceutically acceptable carrier.

In an even further embodiment, there is provided a polynucleotide molecule comprising a nucleic acid sequence encoding the recombinant polypeptide provided herein comprising a serine protease and a sortase recognition sequence or the polypeptide provided herein comprising: (a) a recombinant serine protease polypeptide; (b) a sortase linker; and (c) a cell-targeting polypeptide. Another embodiment provides a host cell comprising said polynucleotide sequence. In some aspects, the host cell is a mammalian cell, a yeast cell, a bacterial cell, a ciliate cell or an insect cell.

A further embodiment provides a method of manufacturing a polypeptide comprising: (a) expressing a polynucleotide provided herein comprising a recombinant serine protease polypeptide, a sortase linker and a cell-targeting polypeptide in a cell under conditions to produce the encoded polypeptide; and (b) purifying the polypeptide from the cell.

In another embodiment, there is provided a method of treating a subject with a cell proliferative disease comprising administering to the subject an effective amount of a compound provided herein. In some aspects, the cell proliferative disease is an autoimmune disease. For example, compound may be used in the treatment of rheumatoid arthritis, psoriasis, osteoarthritis, inflammatory bowel disease, type 1 diabetes, tissue or organ rejection or multiple sclerosis. In these aspects, cell targeting compounds may be used in combination with other treatment regimens, such as steroids.

In other aspects, the cell proliferative disease is a cancer or precancerous condition. For example, the cell proliferative disease is: a myeloma, leukemia or lymphoma; a cancer of the lung, breast, brain, prostate, pancreas, cervix, ovary or Fallopian tube, head and neck, esophagus, liver, skin, kidney, bone, testus, colon, or bladder; or a soft or hard tissue tissue sarcoma. In some aspects, the method further comprises administering at least a second anticancer therapy to the subject. In some aspects, the second anticancer therapy is surgical therapy, chemotherapy, radiation therapy, gene therapy or immunotherapy.

In other embodiments, there is provided a method of treating a bacterial or viral infection comprising administering to the subject an effective amount of a compound provided herein.

In some specific aspects a serine protease for use according to the embodiments comprises a sequence at least about 80%, 85%, 90%, 91%, 92%, 93%, 94%, 95%, 96%, 97%, 98%, 99% or more identical to granzyme B, granzyme A, granzyme H, granzyme K, granzyme M, Cathepsin G, Chymase, Myeloblastin, Kallikrein-14, Complement factor D, PRSS3 protein, Trypsin-1, Serine protease 57 or PRSSL1 protein. In certain aspects, the serine protease is at least about 80%, 85%, 90%, 91%, 92%, 93%, 94%, 95%, 96%, 97%, 98%, 99% or more identical to a human granzyme, such as granzyme B (GrB).

In yet a further embodiment there is a provided a polynucleotide molecule comprising a sequence that encodes a serine protease polypeptide or constructs of the embodiments. In some aspects, the polynucleotide molecule is comprised in an expression cassette operably linked to expression control sequences (e.g., a promoter, enhancer, intron, polyadenylation signal sequence or transcription terminator sequence). In still further aspects, the polynucleotide molecule encodes a serine protease fusion protein such as cell-targeting construct of the embodiments.

It will be understood that in certain cases, a fusion protein may comprise additional amino acids positioned between the truncated serine protease and the cell targeting polypeptide. In general these sequences are interchangeably termed "linker sequences" or "linker regions." One of skill in the art will recognize that linker regions may be one or more amino acids in length and often comprise one or more glycine residue(s) which confer flexibility to the linker. In some specific examples, linkers for use in the current embodiments include, without limitation, the 218 (GST-SGSGKPGSGEGSTKG; SEQ ID NO: 34), the HL (EAAAK; SEQ ID NO: 35) SSG and the G$_4$S (GGGGS; SEQ ID NO: 36) linkers. Such linker sequences can be repeated 1, 2, 3, 4, 5, 6, or more times or combined with one or more different linkers to form an array of linker sequences. For instance, in some applications, a linker region may comprise a protease cleavage site, such as the cleavage site recognized by an endogenous intracellular protease. In this case when the cell targeting construct is internalized into a target cell proteolytic cleavage can separate the serine protease from a cell targeting moiety and/or other polypeptide domains. As such, cell targeting constructs according to this embodiment may have the advantage of enhanced intracellular activity of the targeted serine protease since potential interference from the cell targeting polypeptide will be reduced.

Recombinant fusion polypeptides according to the embodiments may comprise additional amino acids attached to the serine protease, the cell targeting moiety, or both. For example, additional amino acids may be included to aid production or purification of a cell targeting construct. Some specific examples of amino acid sequences that may be attached to cell targeting moiety include, but are not limited to, purification tags (e.g., a T7, MBP. GST, HA, or polyHis tag), proteolytic cleavage sites, such as a thrombin or furin cleavage site, intracellular localization signals or secretion signals.

In still further aspects, a polypeptide of the embodiments further comprises a cell-penetrating peptide (CPP). As used herein the terms CPP and membrane translocation peptide (MTP) as used interchangeably to refer to peptide sequences that enhance the ability of a protein to be internalized by a cell. Examples for CPPs for use according to the embodiments include, without limitation, peptide segments derived from HIV Tat, herpes virus VP22, the Drosophila Antennapedia homeobox gene product, protegrin I, as well as the T1, T2, INF7 and 26 peptides exemplified herein. In certain aspects, a cell-targeting construct of the embodiments comprises CPP positioned between the serine protease and the cell-targeting moiety or positioned C-terminally relative to the cell-targeting moiety. In certain aspects a CPP is separated from a serine protease and/or a cell-targeting moiety by a linker sequence.

A cell targeting construct (e.g., comprising a cell-targeting moiety and a serine protease linked by a sortase) according to the embodiments will desirably have two properties: (1) binding affinity for a specific population of cells; and, (2) the ability to be internalized into cells. It is envisioned, however, that even cell targeting constructs that are poorly internalized may be used in methods according to the embodiments. Methods well known to those in the art may be used to determine whether a particular cell targeting construct is internalized by target cells, for example by immunohistochemical staining or immunoblot of intracellular extracts. It is also envisioned that, in certain cases, cell targeting moieties that cannot, by themselves, be internalized, may be internalized in the context of the cell targeting constructs according to the embodiments. Cell targeting moieties for use in the embodiments include but are not limited to antibodies, growth factors, hormones, peptides, aptamers, avimers (see for example U.S. Patent Publns. 20060234299 and 20060223114, incorporated herein by reference) and cytokines. As discussed above, cell targeting moieties may be conjugated to a serine protease via a covalent or non-covalent linkage, and in certain cases the targeting construct may be a fusion protein.

In certain preferred aspects, cell targeting moieties for use in the embodiments are antibodies or fragments thereof. In general the term antibody includes, but is not limited to, polyclonal antibodies, monoclonal antibodies, single chain antibodies, humanized antibodies, a deimmunized antibodies, minibodies, dibodies, tribodies as well as antibody fragments, such as Fab', Fab, F(ab')$_2$, single domain antibody, Fv, or single chain Fv (scFv) antibody single domain antibodies, VHH antibodies and antibody mimetics, such as anticalins, and any mixture thereof. In some cases the cell targeting moiety is a single chain antibody (scFv). In a related aspect, the cell targeting domain may be an avimer polypeptide. Therefore, in certain cases, the cell targeting constructs of the embodiments are fusion proteins comprising a GrB polypeptide and a scFv or an avimer. For example, in some very specific aspects, the GrB polypeptide is conjugated or fused to a 15A8, scFvMEL, ZME-018, scFv23, cetuximab or trastuzumab antibody. Likewise, a GrB polypeptide may be fused or conjugated to and anti-CD-33 or anti-CD-38 antibody.

Thus, in some embodiments, the invention provides a cell targeting moiety comprising a human antibody heavy chain and light chain, wherein the antibody light chain, heavy chain or both comprise a truncated serine protease of the embodiments positioned C-terminally relative to the antibody light chain and/or heavy chain. For example, the antibody can be a human IgG, such as an IgG1.

In yet further aspects, a cell targeting moiety may be a hormone. Some examples of hormones for use in the embodiments include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin or angiotensinogen. As discussed above targeting constructs that comprise a hormone can be used in methods of targeting cell populations that comprise extracellular receptors for the indicated hormone.

In yet still further aspects of the embodiments, cell targeting moieties may be cytokines. For example, IL1, IL2, IL3, IL4, IL5, IL6, IL7, IL8, IL9, IL10, IL11, IL12, IL13, IL14, IL15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-γ, IFN-α, IFN-β, LT-β, CD40 ligand, Fas ligand, CD27 ligand, CD30 ligand, 4-1BBL, TGF-β, IL 1α, IL-1β, IL-1RA, MIF, TNF-like weak inducer of apoptosis (TWEAK) and IGIF may all be used as targeting moieties according to the embodiments.

From the foregoing description it will be clear to one of skill in the art that cell targeting constructs according to the embodiments may target particular populations of cells depending on the cell targeting moiety that is employed. For instance, the cell targeting moiety may be an infected cell targeting moiety. In this case, the cell targeting moiety may bind to a cellular protein that is primarily expressed on the surface of cells that are infected by a pathogen, such as bacteria, a protozoan or a virus. In certain other aspects, the cell targeting moiety may bind to a factor encoded by the pathogen, such as a bacterial, protozoal or viral protein. In this aspect, it is envisioned that cell targeting constructs may be indirectly targeted to cells by binding to a pathogen before or as it enters a target cell. Thus, the transit of a pathogen into a cell may, in some instances, mediate internalization of the targeting construct. In additional aspects, cell targeting moieties may bind to polypeptides encoded by the pathogen that are expressed on the surface of infected cells. For example, in the case of a cell infected with human immunodeficiency virus (HIV), a cell targeting moiety may bind to, for example, gp120. It is envisioned that any of the foregoing methods may be used to limit the spread of infection. For example, delivery of a serine protease (e.g., GrB) to the infected cell may induce apoptosis or sensitize a cell to undergo apoptosis.

In some aspects of the embodiments a cell-targeting moiety can be defined as an immune cell targeting moiety. In this case, the cell targeting moiety may bind to and/or be internalized by a cell surface molecule that is expressed on a specific populations of immune cells. Thus, targeting a serine protease to certain types of immune cells may be used, for example, to treat autoimmune diseases, cancers, leukemias, myelomas or lymphomas.

In still further aspects of the embodiments a cell targeting moiety can be a cancer cell targeting moiety. It is well known that certain types of cancer cells aberrantly express surface molecules that are unique as compared to surrounding tissue. Thus, cell targeting moieties that bind to these surface molecules enable the targeted delivery of serine proteases specifically to the cancers cells. For example, a cell-targeting moiety may bind to and be internalized by a lung, breast, brain, prostate, spleen, pancreatic, cervical, ovarian, head and neck, esophageal, liver, skin, kidney, leukemia, bone, testicular, colon, sarcoma or bladder cancer cell. Thus, the effectiveness of a cancer cell-targeted serine protease may, in some cases, be contingent upon the expression or expression level of a particular cancer marker on the cancer cell. In certain aspects, there is provided a method for treating a cancer patient with targeted serine protease comprising identifying whether (or to what extent) cancer cells of the patient expresses a particular cell surface marker and administering a targeted serine protease therapy (optionally, in conjunction with a further anticancer therapy) to a patient identified to have a cancer expressing the particular cell surface marker. In further aspects, the dose of a targeted serine protease therapy can be adjusted depending on the expression level of a cell surface marker on the cancer cells.

Accordingly, in certain embodiments, there is provided a method for treating a cell proliferative disease comprising administering a cell-targeting construct according to the embodiments. As used herein the phrase "cell proliferative condition" includes but is not limited to autoimmune diseases, diseases in which there is uncontrolled proliferation of epithelial or mesenchymal components, cancers and precancerous conditions. For example, methods of the embodiments may be used for the treatment of cancers such as lung, breast, brain, prostate, spleen, pancreatic, cervical, ovarian, head and neck, esophageal, liver, skin, kidney, leukemia, bone, testicular, colon, or bladder cancers. For example, there is provided a method for treating a skin cancer, such as a melanoma, by administration of a serine protease targeted to skin cancer cells. Likewise, there is provided a method for treating a gp240 positive skin cancer comprising administering a serine protease of the embodiments that comprises a scFvMEL targeting moiety.

In a further embodiment, there is provided a composition comprising a cell-targeting moiety and a therapeutic agent, wherein the cell-targeting moiety comprises an R-spondin or fragment thereof. In some aspects, the R-spondin is RSPO1 or RSPO2. In particular aspects, the R-spondin is recombinant. In certain aspects, the composition further comprises an imaging agent. The composition may formulated in a liposome or nanoparticle wherein the cell-targeting moiety is conjugated on the surface and the therapeutic agent and/or imaging agent are encapsulated within the particle.

In certain aspects, the therapeutic agent (e.g., an anticancer agent) is a cytotoxic agent, an antibody, a growth factor, a hormone, a peptide, an aptamer, or a cytokine. In some aspects, the cytotoxic agent is further defined as a cytotoxic polypeptide, such as a serine protease, a Bcl-2 family member, cytochrome C, or a caspase. In particular aspects, the serine protease is granzyme B, granzyme A, granzyme H, granzyme K, granzyme M, Cathepsin G, Chymase, Myeloblastin, Kallikrein-14, Complement factor D, PRSS3 protein, Trypsin-1, Serine protease 57 or PRSSL1 protein. In specific aspects, the serine protease is Granzyme B (GrB). In some aspects, the serine protease is a truncated serine protease having an IIGG (SEQ ID NO:91), IVGG (SEQ ID NO:92) or ILGG (SEQ ID NO:93) at its N-terminus. In particular aspects, the GrB polypeptide comprises an amino acid substitution or deletion at one or more positions selected from the group consisting of Asp 37, Asn 51, Asn 84, Arg 96, Arg 100, Arg 102, Asp 150, Arg 201, Cys 210, Lys 221, Lys 222, Lys 225, or Arg 226. Also provided herein are constructs that express R-spondin and a therapeutic polypeptide, optionally fused with a linker.

In some aspects, the cytotoxic agent is a chemotherapeutic or a toxin. In specific aspects, the toxin is auristatin, such as monomethylaurostatin E (MMAE). In one particular aspects, MMAE comprises a protease-cleavable linker (e.g., citrulline-valine).

In certain aspects, the antibody is further defined as a full-length antibody, chimeric antibody, Fab', Fab, F(ab')2, single domain antibody (DAB), Fv, single chain Fv (scFv), minibody, diabody, triabody, or a mixture thereof.

In some aspects, the cell-targeting moiety and the therapeutic agent are chemically conjugated. In certain aspects, the cell-targeting moiety and the therapeutic agent are comprised in a fusion polypeptide. In particular aspects, the cell-targeting moiety and the therapeutic agent are connected by a linker.

In yet another embodiment, there is provided a method of treating cancer in a subject comprising administering to the subject an effective amount of a composition comprising a cell-targeting moiety fused to an anti-cancer agent, wherein the cell-targeting moiety comprises an R-spondin or fragment thereof. In particular aspects, the R-spondin is RSPO1 or RSPO2. In certain aspects, the cancer is a cancer of the lungs, breast, colon, ovary, or endometrium.

In some aspects, the subject has cancer cells that express an LGR receptor. In particular aspects, the cancer cells (e.g., cancer stem cells) overexpress an LGR receptor as compared to normal cells; thus, the anti-cancer agent is selectively delivered to cancer cells. For example, the LGR receptor can be LGR5 or LGR6. In particular aspects, the cancer cells (e.g., cancer stem cells) express LGR6.

In additional aspects, the method further comprises administering at least one additional cancer therapy. In some aspects, the additional cancer therapy is chemotherapy, surgery, radiation, gene therapy, hormone therapy, immunotherapy (e.g., immune checkpoint inhibitor), or a combination thereof. In some aspects, the additional cancer therapy and the composition are administered concomitantly, administered in succession, the composition is administered prior to the additional cancer therapy, or the composition is administered subsequent to the additional cancer therapy.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-5B: GrB-$(G_4S)_2$-LPETGG cDNA (A) (SEQ ID NO: 1) and amino acid sequence (B) (SEQ ID NO: 2).

FIGS. 6A-6C: Graphic alignments of various mammalian granzyme polypeptides and serine proteases having high homology to granzymes. In each case the polypeptide sequences provided are for the mature active polypeptide (i.e., lacking the N-terminal leader sequence). (A) Figure shows an alignment of sequences for GrB from *Homo sapiens* (SEQ ID NO: 3; 100%); *Pan troglodytes* (SEQ ID NO: 4; 98%); *Pan paniscus* (SEQ ID NO: 5; 98%); *Pongo abelii* (SEQ ID NO: 6; 93%); *Macaca nemestrina* (SEQ ID NO: 7; 87%); *Macaca mulatta* (SEQ ID NO: 8; 87%); *Macaca fascicularis* (SEQ ID NO: 9; 86%); *Sus scrofa* (SEQ ID NO: 10; 72%); *Bos taurus* (SEQ ID NO: 11; 72%); *Rattus norvegicus* (SEQ ID NO: 12; 70%); and *Mus musculus* (SEQ ID NO: 13; 71%). Percent values in parenthesis indicate the percent identity to mature *H. sapiens* GrB. The amino acid positions corresponding to human GrB Asp 37, Asn 51, Asn84, Asp150, and Cys210 are each indicated in bold and shaded. * next to *H. sapiens* indicates that certain sequence reads for GrB indicate a "Q" at position 35 rather than the "R" depicted, see e.g., NCBI accession nos. AAA75490.1 versus EAW66003.1. (B) Figure shows an alignment of sequences for various mature Granzyme polypeptides from *Homo sapiens*. Sequences are shown for granzyme B "Gzm B" (SEQ ID NO: 3), granzyme A "Gzm A" (SEQ ID NO: 14), granzyme H "Gzm H" (SEQ ID NO: 15), granzyme K "Gzm K" (SEQ ID NO: 16) and granzyme M "Gzm M" (SEQ ID NO: 17). (C) Figure shows an alignment of sequences for serine protease polypeptides from *Homo sapiens* with high homology to granzyme polypeptides. Sequences are shown for mature granzyme B (SEQ ID NO: 3), Cathepsin G (SEQ ID NO: 18, NCBI accession no. P08311), Chymase (SEQ ID NO: 19, NCBI accession no. P23946), Myeloblastin (SEQ ID NO: 20, NCBI accession no. P24158), Kallikrein-14 (SEQ ID NO: 21, NCBI accession no. Q9P0G3), Complement factor D (SEQ ID NO: 22, NCBI accession no. K7ERG9), PRSS3 protein (SEQ ID NO: 23, NCBI accession no. A1A508), Trypsin-1 (SEQ ID NO: 24, NCBI accession no. P07477), Serine protease 57 (SEQ ID NO: 25, NCBI accession no. Q6UWY2) and PRSSL1 protein (SEQ ID NO: 26, NCBI accession no. B7ZMF6). In the alignments "*" indicated identical amino acid positions, ":" and "." indicate highly similar or similar amino acid positions respectively.

DESCRIPTION OF ILLUSTRATIVE EMBODIMENTS

I. The Present Invention

Figure 1:
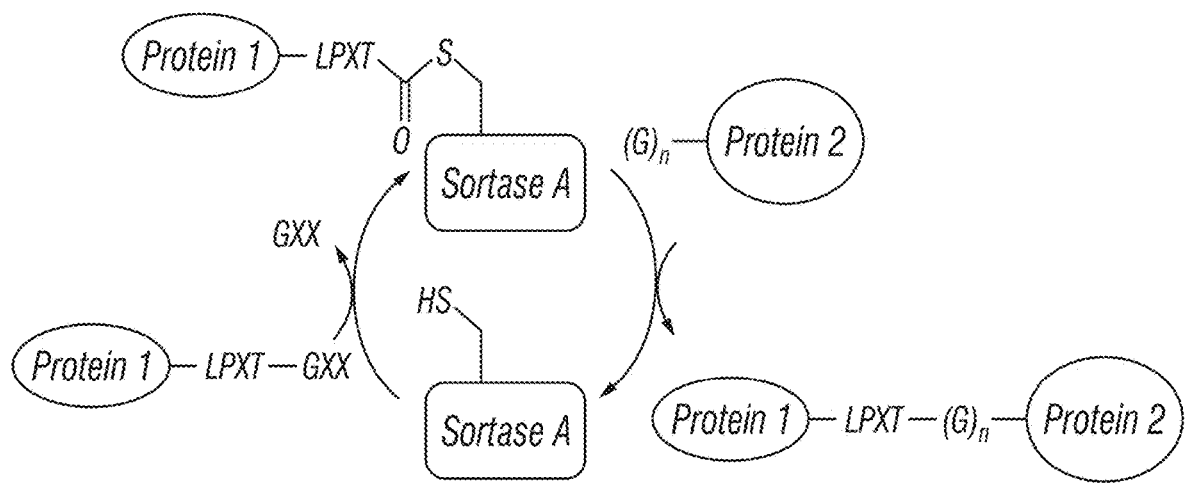
FIG. 1: Schematic of the sortase reaction to form new peptide bonds between two proteins one of which contains LPXTGG (SEQ ID NO:89) at C-terminal end and the other of which contains a GGG sequence at its N-terminal end.

Granzyme B (GrB), a serine-dependent and aspartate-specific protease, is the major effector molecule of cellular immune defense and is released from the granules of activated cytotoxic T lymphocytes or natural killer cells during their attack on other cells. Once in the target cell GrB is activated by removal of two amino acids at the N-terminus; the activated protein then induces apoptosis through either caspase-dependent or independent pathways (Wowk et al., 2004). Engineering the active form of GrB into an immunotoxin not only confines the delivery of the toxin to the antigen-expressing tumor cells, but also eliminates the need for proteolytic activation once internalized into the target cell. GrB has now been used as the warhead in multiple different immunotoxins directed at the FN14 receptor (Zhou et al., 2014), HER2 (Cao et al., 2014), VEGFR (Mohamedali et al., 2009) and melanoma antigens (Liu et al., 2006) each of which has demonstrated nanomolar potency and substantial activity in xenograft models of human cancer. GrB is of particular interest as a warhead because only a few molecules of GrB need to reach the cytoplasm to trigger apoptosis and, as evidenced by the ability of appropriately triggered cytotoxic T cells, there is little resistance to this enzyme. Thus far, GrB immunotoxins have been made with the GrB already fused to the targeting moiety which poses substantial production problems. Thus, the present invention overcome problems associated with current technologies by providing methods and compositions for constructing compounds comprising cytotoxic agents, such as serine protease or MMAE, using the sortase reaction.

In some aspects, there is provided a serine protease (e.g., GrB) cassette that can be snapped onto the N-terminal end of any of a wide variety of cell-targeting proteins using the sortase reaction. For example, the serine protease construct has a C-terminal sortase recognition sequence which can be cleaved by a transpeptidase, such as Sortase A. In some aspects, the sortase recognition sequence has the LPXT (SEQ ID NO:56) motif. In particular aspects, the serine protease and sortase recognition sequence are combined with at least one spacer sequence. In other aspects, the construct does not comprise a spacer. In some aspects, the cell-targeting protein has a polyglycine sequence at its N-terminal.

In further aspects, there are provided methods of producing a cell-targeting fusion protein by combining a serine protease with a C-terminal sortase recognition sequence, a transpeptidase and a cell-targeting peptide or polypeptide with an N-terminal glycine. In this method, the serine protease and cell-targeting moiety are coupled together to form a fusion protein.

In a further aspect, a recombinant fusion protein of the embodiments comprises from N-terminus to C-terminus a serine protease polypeptide; a sortase linker; and a cell-targeting moiety such as yoked human chorionic gonadotropin (YCG). The term "sortase linker" as used herein refers to the amino acid segment which results after a sortase reaction fuses a donor molecule with a C-terminal sortase donor sequence (e.g., LPXT(G)$_n$) (SEQ ID NO:94) and a acceptor molecule with a N-terminal sortase acceptor sequence (e.g., GGG) by cleaving the Thy-Gly bond of the sortase donor sequence and forms a new peptide bond with the sortase acceptor sequence. Thus, the sortase reaction results in the loss of at least 1 Gly from the sortase donor sequence and may result in the loss of 2, 3, or more Gly residues. Such constructs are exemplified herein in Example 2 and demonstrate highly selective toxicity to luteinizing hormone receptor-expressing cells. Accordingly, the fusion proteins provided herein can be used to treat cancers such as ovarian, breast, endometrial and prostate carcinomas.

Certain aspects of the embodiments concern compounds that comprise a cyotoxic agent, such as a serine protease, and a sortase recognition sequence. In preferred aspects, a serine protease for use according to the embodiments is a human or substantially human polypeptide. For example, the truncated serine protease can be a granzyme selected from granzyme B, granzyme A, granzyme H, granzyme K or granzyme M, or a polypeptide at least about 80%, 85%, 90% or 95% identical to one these granzyme polypeptides. In still further aspects, the serine protease is a protease from *Homo sapiens* having an N-terminal amino acid sequence of IIGG (SEQ ID NO:91), IVGG (SEQ ID NO:92) or ILGG (SEQ ID NO:93) (when in its mature, active form). For example, the serine protease can be Cathepsin G (NCBI accession no. P08311), Chymase (NCBI accession no. P23946), Myeloblastin (NCBI accession no. P24158), Kallikrein-14 (NCBI accession no. Q9P0G3), Complement factor D (NCBI accession no. K7ERG9), PRSS3 protein (NCBI accession no. A1A508), Trypsin-1 (NCBI accession no. P07477), Serine protease 57 (NCBI accession no. Q6UWY2) or PRSSL1 protein (NCBI accession no. B7ZMF6) or a polypeptide at least about 80%, 85%, 90% or 95% identical to one these protease polypeptides.

II. Cytotoxic and Cytostatic Agents

A. Serine Protease Polypeptides

Certain aspects of the embodiments concern compounds that comprise a cyotoxic agent, such as a serine protease, and a sortase recognition sequence. In preferred aspects, a serine protease for use according to the embodiments is a human or substantially human polypeptide. For example, the truncated serine protease can be a granzyme selected from granzyme B, granzyme A, granzyme H, granzyme K or granzyme M, or a polypeptide at least about 80%, 85%, 90% or 95% identical to one these granzyme polypeptides. In still further aspects, the serine protease is a protease from Homo sapiens having an N-terminal amino acid sequence of IIGG, IVGG or ILGG (when in its mature, active form). For example, the serine protease can be Cathepsin G (NCBI accession no. P08311), Chymase (NCBI accession no. P23946), Myeloblastin (NCBI accession no. P24158), Kallikrein-14 (NCBI accession no. Q9P0G3), Complement factor D (NCBI accession no. K7ERG9), PRSS3 protein (NCBI accession no. A1A508), Trypsin-1 (NCBI accession no. P07477), Serine protease 57 (NCBI accession no. Q6UWY2) or PRSSL1 protein (NCBI accession no. B7ZMF6) or a polypeptide at least about 80%, 85%, 90% or 95% identical to one these protease polypeptides.

In certain cases, serine protease polypeptides or portions thereof may be from a non-human source or may be from a homologous human polypeptide. For example, in the case of GrB, a polypeptide may comprise one or more amino acid substitutions to an amino acid at a corresponding position in a Pan troglodytes; Pan paniscus; Pongo abelii; Macaca nemestrina; Macaca mulatta; Macaca fascicularis; Sus scrofa; Bos taurus; Rattus norvegicus; or Mus musculus GrB (see, FIG. 6A). Likewise, a granzyme polypeptide of the embodiments may comprise one or more amino acid substitutions to an amino acid at a corresponding position in a different granzyme coding sequence (see, e.g., FIG. 6B). In yet further aspects, a serine protease of the embodiments may comprise one or more amino acid substitutions to an amino acid at a corresponding position in a different, homologous, serine protease coding sequence (see, e.g., FIG. 6C). Because of the high homology shared between these polypeptides, such substitutions for corresponding amino acid positions discussed above would be expected to result in a coding sequences that, when expressed, maintains protease activity.

In certain aspects, a serine protease for use according to the embodiments is a GrB polypeptide. Thus, one or more of the molecules for use in the current embodiments include, but are not limited to, human GrB polypeptide that is at least 70%, 80%, 90%, 95%, 98% or more identical to human GrB (SEQ ID NO: 3). In certain aspects a recombinant GrB sequence is provided wherein one or more amino acid has been substituted for an amino acid at a corresponding position of GrB from another species (other than human).

In some aspects, the serine protease is one described in U.S. Pat. No. 9,096,840 or U.S. Patent Application Nos. 2014/0140976 and 2015/0010556, each incorporated herein by reference in their entirety. For example, in certain specific aspects, a granzyme for use according to the embodiments is a GrB coding sequence comprising one or more amino acid deletions and/or substitutions relative to a human GrB sequence such as SEQ ID NO: 3 (see also NCBI accession numbers nos. AAA75490.1 and EAW66003.1, incorporated herein by reference). For example, the recombinant GrB can be at least 80% identical to SEQ ID NO: 3 (e.g., at least about or about 85%, 90%, 91%, 92%, 93%, 94%, 95%, 96%, 97%, 98% or 99% identical to SEQ ID NO: 3). In certain aspects, a GrB polypeptide comprises one or more amino acid substitution to a corresponding amino acid from a GrB of a different species. For instance, a substantially human GrB polypeptide can comprise 1, 2, 3, 4, 5, or more substitutions at amino acid positions for a corresponding amino acid from one of the GrB polypeptides provided in FIG. 6 (e.g., a primate, porcine, bovine or murine GrB). In some aspects, the recombinant GrB comprises one or more of the following features: (a) an amino acid substitution or deletion at the position corresponding to Asp 37; (b) an amino acid substitution or deletion at the position corresponding to Asp 150; (c) an amino acid substitution or deletion at the position corresponding to Asn 51; (d) an amino acid substitution or deletion at the position corresponding to Asn 84; and/or (e) an amino acid substitution or deletion at the position corresponding to Cys 210. In further aspects, a GrB polypeptide comprises two, three, four or five of the features (a)-(e). In certain aspects, a recombinant GrB is defined as a substantially un-glycosylated GrB polypeptide.

In a further embodiment a recombinant GrB polypeptide of the embodiments comprises one or more of the following features: (a) an amino acid substitution or deletion at the position corresponding to Asp 37; (b) an amino acid substitution or deletion at the position corresponding to Asn 51; (c) an amino acid substitution or deletion at the position corresponding to Asn 84; (d) an amino acid substitution or deletion at the position corresponding to Arg 96; (e) an amino acid substitution or deletion at the position corresponding to Arg 100; (f) an amino acid substitution or deletion at the position corresponding to Arg 102; (g) an amino acid substitution or deletion at the position corresponding to Asp 150; (h) an amino acid substitution or deletion at the position corresponding to Arg 201; (i) an amino acid substitution or deletion at the position corresponding to Cys 210; (j) an amino acid substitution or deletion at the position corresponding to Lys 221; (k) an amino acid substitution or deletion at the position corresponding to Lys 222; (l) an amino acid substitution or deletion at the position corresponding to Lys 225; and/or (m) an amino acid substitution or deletion at the position corresponding to Arg 226. Thus, in some aspects, a recombinant polypeptide of the embodiments comprises 1, 2, 3, 4, 5, 6, 7, 8, 9, 10, 11, 12, or all 13 of the features (a)-(m).

In certain aspects, a recombinant GrB polypeptide lacks glycosylation at an amino acid position corresponding to human amino acid position Asn 51 and/or Asn 84. In some aspects, a GrB polypeptide of the embodiments comprises an amino acid substitution or deletion at a position corresponding to human amino acid position Asn 51 and/or Asn 84. In further aspects, a GrB polypeptide comprises a Arg, His, Lys, Asp, Glu, Ser, Thr, Gln, Cys, Gly, Pro, Ala, Val, Ile, Leu, Met, Phe, Tyr or Trp substitution at human amino acid position Asn 51 and/or Asn 84. For example, in one aspect, a recombinant GrB comprises an Ala, Ser, Thr, Lys or Gln substitution at a position corresponding to human amino acid position Asn 51. Alternatively or additionally, a recombinant GrB comprises an Ala, Ser, Thr, Arg or Gln substitution at a position corresponding to human amino acid position Asn 84.

In some aspects, a recombinant GrB polypeptide comprises an amino acid substitution or deletion at the positions corresponding to Lys 27 and/or Arg 28. For example, a recombinant GrB may comprise a substitution at both the positions corresponding to Lys 27 and Arg 28. In some cases, the substitution is selected from K27E or K27L and R28A. In still further aspects, a recombinant GrB coding sequence one, two or three amino acid substitutions or deletions at the positions corresponding to $^{82}PKN^{84}$. For example, in some specific aspects, a GrB coding sequence comprises the sequence PVPN substituted at the positions corresponding to $^{82}P_{KN}{}^{84}$.

In further aspects, a recombinant GrB polypeptide of the embodiments comprises an amino acid deletion or substitution (e.g., a substitution of an amino acid having a polar side chain) at an amino acid position corresponding to human amino acid position Asp 37 and/or Asp 150. Thus, in some aspects a recombinant GrB polypeptide comprises a Arg, His, Lys, Glu, Ser, Thr, Asn, Gln, Cys, Gly, Pro, Ala, Val, Ile, Leu, Met, Phe, Tyr or Trp substitution at at to human amino acid position Asp 37 and/or Asp 150. For example, a recombinant GrB can comprise a Ser, Thr, Gln, Glu or Asn substitution at a position corresponding to human amino acid position Asp 37. Alternatively or additionally, a recombinant GrB comprises a Ser, Thr, Gln, Glu or Asn substitution at a position corresponding to human amino acid position Asp 150.

In some aspects, a recombinant GrB polypeptide of the embodiments comprises an amino acid substitution or deletion at a position corresponding to human amino acid position Arg 96, Arg 100, Arg 102, Arg 201, and/or Arg 226. In further aspects, a GrB polypeptide comprises a Asn, His, Lys, Asp, Glu, Ser, Thr, Gln, Cys, Gly, Pro, Ala, Val, Ile, Leu, Met, Phe, Tyr or Trp substitution at human amino acid position Arg 96, Arg 100, Arg 102, Arg 201, and/or Arg 226. In certain aspects, a recombinant GrB comprises a substitution at a position corresponding to Arg 96, Arg 100, Arg 102, Arg 201, and/or Arg 226 for an amino acid residue having a polar or positively charged side chain. For example, a recombinant GrB can comprise an Ala, Asn, Ser, Thr, Lys, His or Gln substitution at a position corresponding to human amino acid position Arg 96, Arg 100, Arg 102, Arg 201, and/or Arg 226. In still further aspects, a recombinant polypeptide comprises a deletion or substitution at 2, 3, 4 or 5 of said Arg positions.

In certain aspects, a recombinant GrB polypeptide of the embodiments comprises an amino acid substitution or deletion at a position corresponding to human amino acid position Lys 221, Lys 222 and/or Lys 225. In further aspects, a GrB polypeptide comprises a Asn, His, Arg, Asp, Glu, Ser, Thr, Gln, Cys, Gly, Pro, Ala, Val, Ile, Leu, Met, Phe, Tyr or Trp substitution at human amino acid position Lys 221, Lys 222 and/or Lys 225. In certain aspects, a recombinant GrB comprises a substitution at a position corresponding to Lys 221, Lys 222 and/or Lys 225 for an amino acid residue having a polar or positively charged side chain. For example, a recombinant GrB can comprise an Ala, Asn, Ser, Thr, Arg, His or Gln substitution at a position corresponding to human amino acid position Lys 221, Lys 222 and/or Lys 225. In still further aspects, a recombinant polypeptide comprises a deletion or substitution at 2 or 3 of said Lys positions.

In still further aspects, a recombinant GrB polypeptide of the embodiments comprises an amino acid deletion or substitution at the position corresponding to Cys 210. In some aspects, recombinant GrB comprises a Arg, His, Lys, Asp, Glu, Ser, Thr, Asn, Gln, Gly, Pro, Ala, Val, Ile, Leu, Met, Phe, Tyr or Trp amino acid substitution at the position corresponding to Cys 210. For example, the recombinant GrB polypeptide can comprise an Ala, Val, Ile, Leu, Met, Ser, Thr, Asn, Phe, Tyr or Gln substitution at the position corresponding to Cys 210.

In still a further embodiment, the serine protease is a truncated serine protease such that the leader sequence, positioned N-terminally relative to a IIGG (SEQ ID NO:91), IVGG (SEQ ID NO:92) or ILGG (SEQ ID NO:93) sequence has been removed or replaced with a heterologous sequence. Thus, in certain embodiments the serine protease is a recombinant polypeptide comprising a cleavage site that is susceptible to cleavage by a selected protease fused to a truncated serine protease having an IIGG (SEQ ID NO:91), IVGG (SEQ ID NO:92) or ILGG (SEQ ID NO:93) at its N-terminus, such that, upon cleavage of the polypeptide by the selected protease, the truncated serine protease having an N-terminal isoleucine will be released from the polypeptide. In some aspects, the protease cleavage site is a caspase, furin, granzyme B or factor Xa cleavage sequence. In some aspects, the protease cleavage site is for an intracellular or extracellular protease. For instance, the cleavage site can be a caspase 1-10 cleavage site (e.g., YEVD (SEQ ID NO:96), WEHD (SEQ ID NO:97), DVAD (SEQ ID NO:98), DEHD (SEQ ID NO:99), DEVD (SEQ ID NO:100), DMQD (SEQ ID NO:101), LEVD (SEQ ID NO:102), LEHD (SEQ ID NO:103), VEID (SEQ ID NO:104), VEHD (SEQ ID NO:105), IETD (SEQ ID NO:106), LETD (SEQ ID NO:107) or LEAD (SEQ ID NO:108), a furin cleavage site (RVRR) (SEQ ID NO:109), a granzyme B cleavage site (IEPD) (SEQ ID NO:110) or a factor Xa cleavage site ((UA)(E/D)GR).

Thus, in the case of GrB, upon protease cleavage free GrB is released having an amino terminal sequence of IIGGHEAK (SEQ ID NO: 38). In certain aspects, the protease cleavage site is a site cleaved by a mammalian intracellular protease (e.g., a protease that cleaves at the C-terminus of its recognition sequence). In some aspects, the recombinant serine protease is a GrB polypeptide and comprises the sequence YVDEVDIIGGHEAK (SEQ ID NO: 39); RVRRIIGGHEAK (SEQ ID NO: 40); RVRRIIGGHEAK (SEQ ID NO: 41); (I/A)(E/D)GRIIGGHEAK (SEQ ID NO: 42); YEVDIIGGHEAK (SEQ ID NO: 43); WEHDIIGGHEAK (SEQ ID NO: 44); DVADIIGGHEAK (SEQ ID NO: 45); DEHDIIGGHEAK (SEQ ID NO: 46); DEVDIIGGHEAK (SEQ ID NO: 47); DMQDIIGGHEAK (SEQ ID NO: 48); LEVDIIGGHEAK (SEQ ID NO: 49); LEHDIIGGHEAK (SEQ ID NO: 50); VEIDIIGGHEAK (SEQ ID NO: 51); VEHDIIGGHEAK (SEQ ID NO: 52); IETDIIGGHEAK (SEQ ID NO: 53); LETDIIGGHEAK (SEQ ID NO: 54) or IEADIIGGHEAK (SEQ ID NO: 55).

In additional aspects, serine protease polypeptides may be further modified by one or more other amino substitutions while maintaining their enzymatic activity. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in GrB and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the GrB polypeptides described herein may be modified by the substitution of an amino acid, for different, but homologous amino acid with a similar hydrophilicity value. Amino acids with hydrophilicities within +/−1.0, or +/−0.5 points are considered homologous. Furthermore, it is envisioned that serine protease sequences may be modified by amino acid deletions, substitutions, additions or insertions while retaining its enzymatic activity.

B. Additional Cytotoxic and Cytostatic Agents

Cytotoxic proteins for use in the present disclosure may further be selected from apoptotic factors or apoptosis related proteins including AIF, Apaf e.g. Apaf-1, Apaf-2, Apaf-3, oder APO-2 (L), APO-3 (L), Apopain, Bad, Bak, Bax, Bcl-2, Bcl-$x_L$, Bcl-$x_S$, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and transglutaminase.

In further embodiments, the cytotoxic agent may be selected from bispecific antibodies and bioactive compounds including nucleic acids like DNA, mRNA, siRNA, and fragments of these; pharmaceutical compounds such as various therapeutic drugs; and radionuclides and cytotoxins, which can be targeted to a desired tissue or cell by the targeting moiety. These agents may act while they remain conjugated to the targeting protein or a portion thereof, or they may first detach from the targeting protein if the linking group is one that can readily cleave in vivo.

Suitable cytotoxic agents for use with the present disclosure include microtubule inhibitors, topoisomerase I inhibitors, intercalating agents, inhibitors of intracellular signaling pathways, kinase inhibitors, transcription inhibitors such as siRNAs, aRNAs, and miRNAs, and DNA minor groove binders. The cytotoxic agents may include compound classes such as maytansinoids, auristatins, amanitins, calicheamycins, psymberins, duocarmycins, anthracyclins, camptothecins, doxoru bicins, taxols, and pyrrolobenzodiazepines. Specific examples of cytotoxic agents include paclitaxel, docetaxel, etoposide, tenoposide, vincristine, vinblastine, colchicine, doxorubicin, daunorubicin, mithramycin, actinomycin, glucorticoids, puromycin, epirubicin, cyclophosphamide, methotrexate, cytarabine, f-fluorouracil, platins, streptozotocin, minomycin C, anthracyclines, dactinomycin or actinomycin, bleomycin, mithramycin, anthramycin, duocarmycins, ifosfamide, mitoxantrone, daunomycin, carminomycin, animoterin, melphalan, esperamicins, lexitropsins, auristatins (e.g., auristatin E, auristatin F, AEB, AEVB, AEFP, MMAE, MMAF), eleuthorobin, netropsin, podophyllotoxins, maytansiods including maytansine and DM1, and combretestatins.

II. Sortases

Certain embodiments concern sortase recognition sequences and the corresponding sortases. In some aspects, sortase-catalyzed transacylation reactions allow the preparation of head-to-tail protein-protein fusions under native conditions, with excellent specificity and in near-quantitative yields (Popp M W, Ploegh H L (2011) Making and Breaking Peptide Bonds: Protein Engineering Using Sortase. Angew Chem Int Ed 50:5024-5032; Guimaraes C P et al. (2011) Identification of host cell factors required for intoxication through use of modified cholera toxin. *J Cell Biol* 195:751-764; and Popp M W, Antos J M, Grotenbreg G M, Spooner E, Ploegh H L (2007) Sortagging: a versatile method for protein labeling. *Nat Chem Biol* 3:707-708; the entire contents of each of which are incorporated herein by reference).

Sortases, sortase-mediated transacylation reactions, and their use in transacylation (sometimes also referred to as transpeptidation) for protein engineering are well known to those of skill in the art (see, e.g., Ploegh et al., International Patent Application PCT/US2010/000274, and Ploegh et al., International Patent Application PCT/US2011/033303, the entire contents of each of which are incorporated herein by reference). In general, the transpeptidation reaction catalyzed by sortase results in the ligation of species containing a transamidase recognition motif with those bearing one or more N-terminal glycine residues. In some embodiments, the sortase recognition motif is an LPXT (SEQ ID NO:56) motif or an LPXT(G)$_n$ (SEQ ID NO:94) motif. As is known in the art, the substitution of the C-terminal residue of the recognition sequence with a moiety exhibiting poor nucleophilicity once released from the sortase provides for a more efficient ligation.

Sortase-mediated transacylation reactions are catalyzed by the transamidase activity of sortase. A transamidase is an enzyme that can form a peptide linkage (i.e., amide linkage) between an acyl donor compound and a nucleophilic acyl acceptor containing a $NH_2$—$CH_2$-moiety. In some embodiments, the sortase is sortase A (SrtA). However, it should be noted that any sortase, or transamidase catalyzing a transacylation reaction can be used in embodiments of this invention.

In some embodiments, the sortase, or transamidase, recognition sequence is LPXT (SEQ ID NO: 56), wherein X is a standard or non-standard amino acid. In some embodiments, X is selected from D, E, A, N, Q, K, or R. In some embodiments, the recognition sequence is selected from LPXT (SEQ ID NO: 56), SPXT (SEQ ID NO: 57), LAXT (SEQ ID NO: 58), LSXT (SEQ ID NO: 59), NPXT (SEQ ID NO: 60), VPXT (SEQ ID NO: 61), IPXT (SEQ ID NO: 62), and YPXR (SEQ ID NO: 63). In some embodiments, X is selected to match a naturally occurring transamidase recognition sequence. Variant sortase recognition sequences are known and described in PCT international patent application WO 2013003555, U.S. Pat. No. 7,238,489 and U.S. Patent Application publication 20140030697, which are fully incorporated by reference herein in their entirety. Examples of other sortase recognition sequences, include, but are not limited to LPKTG (SEQ ID NO: 90), LPATG (SEQ ID NO: 64), LPNTG (SEQ ID NO: 65), LPETG (SEQ ID NO: 66), LPXAG (SEQ ID NO: 67), LPNAG (SEQ ID NO: 68), LPXTA (SEQ ID NO: 69), LPNTA (SEQ ID NO: 70), LGXTG (SEQ ID NO: 71), LGATG (SEQ ID NO: 72), IPXTG (SEQ ID NO: 73), IPNTG (SEQ ID NO: 74), and IPETG (SEQ ID NO: 75). Further examples of sortase recognition sequences, include, but are not limited to LPKTGG (SEQ ID NO: 76), LPATGG (SEQ ID NO: 77), LPNTGG (SEQ ID NO: 78), LPETGG (SEQ ID NO: 79), LPXAGG (SEQ ID NO: 80), LPNAGG (SEQ ID NO: 81), LPXTAG (SEQ ID NO: 82), LPNTAG (SEQ ID NO: 83), LGXTGG (SEQ ID NO: 84), LGATGG (SEQ ID NO: 85), IPXTGG (SEQ ID NO: 86), IPNTGG (SEQ ID NO: 87), and IPETGG (SEQ ID NO: 88).

In some embodiments, the coding sequence of sortase recognition is operably linked to the coding sequence of the serine protease via a linker. Any suitable linker known to one of skilled in the art can be used. In a particular embodiment, the linker is a (GGS) or (G$_4$S) linker. The (G$_4$S) linker facilitates the sortase domain to have the conformational freedom to recognize the sortase recognition motif.

III. Cell Targeting Moieties

As discussed above cell targeting moieties according to the embodiments may be, for example, an antibody, a growth factor, a hormone, a peptide, an aptamer or a cytokine. For instance, a cell targeting moiety according the embodiments may bind to a skin cancer cell such as a melanoma cell. It has been demonstrated that the gp240 antigen is expressed in a variety of melanomas but not in normal tissues. Thus, in certain aspects of the embodiments, there is provided a cell targeting construct comprising an GrB and a cell targeting moiety that binds to gp240. In some instances, the gp240 binding molecule may be an antibody, such as the ZME-018 (225.28S) antibody or the 9.2.27 antibody. In an even more preferred embodiment, the gp240 binding molecule may be a single chain antibody such as the scFvMEL antibody. Therefore, in a very specific embodiment of the invention, there is provided a cell targeting construct comprising human GrB conjugated to scFvMEL.

In yet further specific embodiments of the invention, cell targeting constructs may be directed to breast cancer cells. For example cell targeting moieties that bind to Her-2/neu, such as anti-Her-2/neu antibodies may conjugated to GrB. One example of such a cell targeting construct is a fusion protein comprising the single chain anti-Her-2/neu antibody scFv23 and GrB. Other scFv antibodies such as scFv(FRP5) that bind to Her-2/neu may also be used in the compositions and methods of the current embodiments (von Minckwitz et al., 2005).

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example are the cell targeting agents described in U.S. patent application no. 2004005647 and in Winthrop et al., 2003 that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy.

Since a large number of cell surface receptors have been identified in hematopoietic cells of various lineages, ligands or antibodies specific for these receptors may be used as cell-specific targeting moieties. IL2 may also be used as a cell-specific targeting moiety in a chimeric protein to target IL2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL4 receptor and may be targeted by moieties that bind these receptors, such as CD40 ligand, IL4, IL5, IL6 and CD28. The elimination of immune cells such as T cells and B cells is particularly useful in the treatment of autoimmunity, hypersensitivity, transplantation rejection responses and in the treatment of lymphoid tumors. Examples of autoimmune diseases are multiple sclerosis, rheumatoid arthritis, insulin-dependent diabetes mellitus, systemic lupus erythemotisis, scleroderma, and uviatis. More specifically, since myelin basic protein is known to be the major target of immune cell attack in multiple sclerosis, this protein may be used as a cell-specific targeting moiety for the treatment of multiple sclerosis (WO 97/19179; Becker et al., 1997).

Other cytokines that may be used to target specific cell subsets include the interleukins (IL1 through IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that bind to the Fn14 receptor, such as TWEAK (see, e.g., Winkles 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β; immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010;

7,781,565; 8,507,445; and 8,450,278, each of which is incorporated herein by reference.

Over the past few years, several monoclonal antibodies have been approved for therapeutic use and have achieved significant clinical and commercial success. Much of the clinical utility of monoclonal antibodies results from the affinity and specificity with which they bind to their targets, as well as long circulating life due to their relatively large size. Monoclonal antibodies, however, are not well suited for use in indications where a short half-life is advantageous or where their large size inhibits them physically from reaching the area of potential therapeutic activity.

Thus, in highly preferred embodiments, cell targeting moieties are antibodies or avimers. Antibodies and avimers can be generated to virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Applns. 20060234299 and 20060223114, each incorporated herein by reference.

A. Antibodies and Antibody-Like Targeting Moieties

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular Immuno-Pharmaceuticals ("$SMIP_S$™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. In some aspects, the antibody can be a VHH (i.e., an antigen-specific VHH) antibody that comprises only a heavy chain. For example, such antibody molecules can be derived from a llama or other camelid antibody (e.g., a camelid IgG2 or IgG3, or a CDR-displaying frame from such camelid Ig) or from a shark antibody. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting.

As used herein, an "antibody fragment" includes a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In some aspects, the antibody fragment can be a VHH antibody.

"Mini-antibodies" or "minibodies" are also contemplated for use with the present embodiments. Minibodies are sFv polypeptide chains which include oligomerization domains at their C-termini, separated from the sFv by a hinge region (Pack et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

In some cases antibody-like molecules are protein scaffolds that can be used to display antibody CDR domains. The origin of such protein scaffolds can be, but is not limited to, the structures selected among: fibronectin (see, e.g., U.S. Patent Publn. No. 20090253899, incorporated herein by reference) and preferentially fibronectin type III domain 10, protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat." The techniques for preparing and using various antibody-based constructs and fragments are well known in the art. Additional antibody-like molecules, such as anti-calins are described in detail in US Patent Publication Nos. 20100285564, 20060058510, 20060088908, 20050106660, PCT Publication No. WO2006/056464 and (Skerra, 2001), incorporated herein by reference.

Antibody-like binding peptidomimetics are also contemplated in the present embodiments. Liu et al. (2003) describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using such peptides are provided in U.S. Patent Publn. 20100317547, incorporated herein by reference.

Monoclonal antibodies (MAbs) are recognized to have certain advantages, e.g., reproducibility and large-scale production. Embodiments of the invention provide monoclonal antibodies of the human, murine, monkey, rat, hamster, rabbit and chicken origin. Due to the ease of preparation and ready availability of reagents, murine monoclonal antibodies will often be preferred.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. Methods for humanizing antibodies such as those provided here are well known in the art, see, e.g., Harvey et al., 2004, incorporated herein by reference.

B. R-Spondins (RSPOs)

The LGR family of G-protein-coupled 7-transmembrane spanning receptors contains 8 members all of which have large extracellular domains consisting of up to 18 copies of a leucine-rich repeat motif. The κ receptors fall into 3 groups. The first consists of LGR1 which is the FSH receptor, LGR2 the LH receptor, and LGR3 the TSH receptor. The second consists of LGR4, LGR5, and LGR6 which are receptors for the R-spondins (RSPOs) and the third group contains LGR7 and LGR8 which are receptors for relaxin and the insulin-like 3 protein, respectively. LGR5 and LGR6 are the best defined markers for stem cells in the gut (LGR5) and skin and Fallopian tube epithelium (LGR6), respectively. LGR5 was shown to be positively regulated by the Wnt signaling pathway that controls the proliferation of the stem cells that form the epithelium of the colon, small intestine and stomach. During embryonic development LGR5 is expressed in multiple tissues, but in the adult its expression is very restricted to rare cells in the gut, breast, ovary, testis, hair follicles, brain and eye. Using a genetic marking technique, cells that express LGR5 were found to function as stem cells capable of giving rise to all the other types of cells found in the epithelium of the colon and stomach. In contrast to LGR5, LGR6 is not regulated by Wnt signaling. In LGR6-LacZ$^{LacZ}$ knock-in mice expression was found to be limited to rare cells in the brain, breast, lung and hair follicles. Lineage mapping has shown that LGR6-positive cells residing in the bulb of the hair follicle are located in a different position than the LGR5-positive cells, and that they give rise to the epidermis and sebaceous glands. Subsequent studies demonstrated that LGR6-expressing cells are the stem cells that generate the new skin needed during the wound healing process. There is also evidence that LGR6 is uniquely expressed by tumor stem cells. LGR6 was found to mark the subpopulation of cells isolated from human lung adenocarcinomas that are capable of forming new tumors in injected into mice.

LGR5 and LGR6 are expressed in many types of tumors including cancers of the breast, colon and endometrium. There are several lines of evidence suggesting that LGR6 rather than LGR5 uniquely identifies stem cells in the Fallopian tube epithelium (FTE) and in ovarian cancers. Thus, LGR6 appears to stem cells in tumors arising from the FTE. Therefore, embodiments of the present disclosure concern the use of LGR6 as a target of tumor stem cells as it is expressed on the cell surface where it is potentially accessible to antibodies and other kinds of tumor-targeting toxins.

R-spondins (RSPOs) are the ligands for LGR5 and LGR6. RSPO are a group of 4 cysteine-rich secreted paralogs (R-spondin1-4). They share an overall similarity of 40-60% sequence homology and domain architecture. All 4 RSPO family members contain an N-terminal secretory signal peptide, 2 tandem furin-like cysteine-rich (Fu-CRD) domains, a thrombospondin type1 repeat (TSP) domain, and a C-terminal basic amino acid-rich (BR) domain. RSPO1 and RSPO2 have been identified as the ligands for both LGR5 and LGR6 receptors to which they bind with high affinity. Therefore, certain embodiments of the present disclosure concern the use of RSPOs to target a therapeutic agent to cells which tumor stem cells which express LGR6. In one particular aspect, RSPO1 and/or RSPO2 are linked to a cytotoxic agent, such as the toxin monomethylaurostatin E (MMAE), to selectively target tumors that express high levels of the LGR6.

IV. Fusion Proteins and Conjugates

A. Linkers

A variety of linkers can be used in constructs, such as truncated serine protease constructs, of the embodiments. In some aspects a linker can be a random string of one or more amino acids (e.g., 2, 3, 4, 5, 10, 15, 20 or more amino acids). Some specific linkers for use according the embodiments include the 218 (GSTSGSGKPGSGEGSTKG; SEQ ID NO: 34), the HL (EAAAK; SEQ ID NO: 35) and the G$_4$S (GGGGS; SEQ ID NO: 36) linkers (e.g., Robinson et al., 1998; Arai et al., 2004 and Whitlow et al., 1993, each incorporated herein by reference).

In further aspects, a linker can serve as a way of separating different domains of a polypeptide construct, such as by proteolytic cleavage. For example, a linker region may comprise a protease cleavage site, such as the cleavage site recognized by an endogenous intracellular protease. In still further aspects, a protease cleavage site can be a site that is only cleaved in certain cell types (e.g., a site cleaved by a viral protease, such as HIV protease, which is only cleaved in infected cells). Example of protease cleavage site for use according to the embodiments include, without limitation, thrombin, furin (Goyal et al., 2000) and caspase cleavage sites.

The cell targeting constructs of the embodiments may be joined by a variety of conjugations or linkages that have been previously described in the art. In one example, a biologically-releasable bond, such as a selectively-cleavable linker or amino acid sequence may be used. For instance, peptide linkers that include a cleavage site for an enzyme preferentially located or active within a tumor environment are contemplated. For example, linkers that are cleaved by urokinase, plasmin, thrombin, Factor IXa, Factor Xa, or a metalloproteinase, such as collagenase, gelatinase, or stromelysin. In a preferred embodiment, a linker that is cleaved by an intracellular proteinase is preferred, since this will allow the targeting construct to be internalized intact into targeted cells prior to cleavage.

Amino acids such as selectively-cleavable linkers, synthetic linkers, or other amino acid sequences such as the glycine rich linkers are described above and may be used to separate proteinaceous components. In some specific examples linkers for use in the current embodiments include the 218 linker (GSTSGSGKPGSGQGSTKG) (SEQ ID NO: 37) or the G$_4$S linker (GGGGS) (SEQ ID NO: 36). Additionally, while numerous types of disulfide-bond containing linkers are known that can successfully be employed to conjugate the GrB with a cell targeting moiety, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

C. Conjugates

Additionally, any other linking/coupling agents and/or mechanisms known to those of skill in the art can be used to combine the components of the present embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is contemplated that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Thorpe et al., 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

D. Cell Penetrating and Membrane Translocation Peptides

Furthermore, in certain aspects, library sequences can include segments of sequence that encode polypeptides having a known function, such as a cell-binding domain or cell penetrating peptide (CPP) in the ORF sequence along with sequence derived from cDNA or randomized sequence (i.e., to generate an ORF encoding a fusion protein). Thus, in certain aspects, DNA molecules of the embodiments comprise an ORF that comprises a CPP coding sequence along with a segment of library sequence (such as randomized sequence), 5' of the CPP coding sequence 3' of the CPP coding sequence or both. As used herein the terms "cell penetrating peptide" and "membrane translocation domain" are used interchangeably and refer to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ; SEQ ID NO: 27), herpes virus VP22, the Drosophila Antennapedia homeobox gene product, protegrin I, Penetratin (RQIKIWFQNRRMKWKK; SEQ ID NO: 28) or melittin (GIGAVLKVLTTGLPAL-ISWIKRKRQQ; SEQ ID NO: 29). In certain aspects the CPP comprises the T1 (TKIESLKEHG; SEQ ID NO: 30), T2 (TQIENLKEKG; SEQ ID NO: 31), 26 (AALEA-LAEALEALAEALEALAEAAAA; SEQ ID NO: 32) or INF7 (GLFEAIEGFIENGWEGMIEGWYGCG; SEQ ID NO: 33) CPP sequence.

V. Administration and Pharmaceutical Formulations

In some embodiments, an effective amount of a cell targeting construct is administered to a cell. In other embodiments, a therapeutically effective amount of the targeting construct is administered to an individual for the treatment of disease. The term "effective amount" as used herein is defined as the amount of the cell targeted cytotoxic agent, such as truncated serine protease, particularly GrB, of the present embodiments that is necessary to result in a physiological change in the cell or tissue to which it is administered either when administered alone or in combination with a cytotoxic therapy. The term "therapeutically effective amount" as used herein is defined as the amount of the targeting molecule of the present embodiments that eliminate, decrease, delay, or minimize adverse effects of a disease, such as cancer. A skilled artisan readily recognizes that, in many cases, cell targeted cytotoxic agents may not provide a cure but may only provide partial benefit, such as alleviation or improvement of at least one symptom. In some embodiments, a physiological change having some benefit is also considered therapeutically beneficial. Thus, in some embodiments, an amount of cell targeted cytotoxic agents, such as serine protease (e.g., GrB) that provides a physiological change is considered an "effective amount" or a "therapeutically effective amount." It will additionally be clear that a therapeutically effective amount may be dependent upon the inclusion of additional therapeutic regimens tat administered concurrently or sequentially. Thus it will be understood that in certain embodiments a physical change may constitute an enhanced effectiveness of a second therapeutic treatment.

The cell targeting compounds of the embodiments may be administered to a subject per se or in the form of a pharmaceutical composition for the treatment of cancer, autoimmunity, transplantation rejection, post-traumatic immune responses and infectious diseases, for example by targeting viral antigens, such as gp120 of HIV. More specifically, the targeted compounds may be useful in eliminating cells involved in immune cell-mediated disorder, including lymphoma; autoimmunity, transplantation rejection, graft-versus-host disease, ischemia and stroke. Pharmaceutical compositions comprising the proteins of the embodiments may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

In preferred embodiments, cancer cells may be treated by methods and compositions of the embodiments. Cancer cells that may be treated with cell targeting constructs according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In preferred embodiments systemic formulations of the cell targeting compounds are contemplated. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. In the most preferred embodiments, the cell targeted cytotoxic agent is delivered by direct intravenous or intratumoral injection.

For injection, the proteins of the embodiments may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

A. Effective Dosages

The cell targeted cytotoxic agent, such as serine protease, of the embodiments will generally be used in an amount effective to achieve the intended purpose. For use to treat or prevent a disease condition, the molecules of the embodiments, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with serine protease constructs of the embodiments include, but are not limited to, steroid and non-steroid anti-inflammatory agents.

B. Toxicity

Preferably, a therapeutically effective dose of the cell targeted cytotoxic agent, such as GrB, described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

C. Pharmaceutical Preparations

Pharmaceutical compositions of the present embodiments comprise an effective amount of one or more the present compounds and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The cell targeted cytotoxic agent, such as serine protease, may comprise different types of carriers depending on whether it is to be administered in solid, liquid or aerosol form, and whether it need to be sterile for such routes of administration as injection. The present therapies of the embodiments can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present embodiments administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VI. Combination Therapies

In order to increase the effectiveness of a nucleic acid, polypeptide or nanoparticle complex of the present embodiments, it may be desirable to combine these compositions with other agents effective in the treatment of the disease of interest.

As a non-limiting example, the treatment of cancer may be implemented with a cell-targeted therapeutic, such as serine protease, of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the anti-cancer peptide or nanoparticle complex and the other includes the second agent(s). In particular embodiments, an anti-cancer peptide can be one agent, and an anti-cancer nanoparticle complex can be the other agent.

Treatment with the anti-cancer peptide or nanoparticle-complex may precede or follow the other agent treatment by intervals ranging from minutes to weeks. In embodiments where the other agent and the anti-cancer peptide or nanoparticle complex are applied separately to the cell, one would generally ensure that a significant period of time did not expire between the time of each delivery, such that the agent and the anti-cancer peptide or nanoparticle complex would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where the targeted cytotoxic agent-based therapy is "A" and the secondary agent, such as radiotherapy, chemotherapy or anti-inflammatory agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In certain embodiments, administration of the therapy of the present embodiments to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies. In some aspects a serine protease therapeutic of the embodiments is administered (or formulated) in conjunction with a chemotherapeutic agent. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD- 6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifo sfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

B. Radiotherapy

Radiotherapy has been used extensively in treatments and includes what are commonly known as γ-rays, X-rays, and/or the directed delivery of radioisotopes to tumor cells. Other forms radiotherapy are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a serine protease therapy of the present embodiments. The general approach for combined therapy is discussed below. Generally, the tumor cell must bear some marker that is amenable to targeting, i.e., is not present on the majority of other cells. Many tumor markers exist and any of these may be suitable for targeting in the context of the present embodiments. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these method are well known in the art (see, e.g. Sambrook et al., 1989; Ausubel et al., 1998; Ausubel, 1996).

Delivery of a vector encoding one of the following gene products will have a combined anti-hyperproliferative effect on target tissues. A variety of proteins are encompassed within the present embodiments and are well known in the art.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

VII. Examples

The following examples are included to demonstrate preferred embodiments of the embodiments. It should be appreciated by those of skill in the art that the techniques disclosed in the examples which follow represent techniques discovered by the inventor to function well in the practice of the embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Granzyme B Construct for Sortase Reaction

Currently, GrB immunotoxins have been made with the GrB already fused to the targeting moiety which poses substantial production problems. Thus, a GrB cassette was constructed that can be snapped onto the N-terminal end of any of a wide variety of proteins that target tumors using the sortase reaction.

Sortase A is a transpeptidase found in most gram positive bacteria that can form new peptide bonds between two proteins one of which contains the sequence LPXTG(G) (SEQ ID NO: 89) at its C-terminal end and the other of which contains a GGG sequence at it N-terminal end. As shown in FIG. 1, sortase cleaves the Thr-Gly bond in the LPXTG(G) (SEQ ID NO: 89) sequence and forms an intermediate in which it is linked to the Thr via a thioester bond. The intermediate then reacts with the GGG sequence on the recipient to form a new peptide bond that links them together (Ton-That et al., 2000; Aulabaugh et al., 2007). The sortase reaction is remarkably specific and, since it takes place under physiologic conditions, it can be used to couple together two recombinant proteins that cannot be produced in high yield if already linked as a fusion protein. It can also be used to couple a drug, or a scaffold that can be loaded with drug, to a recombinant protein (Tsukiji et al., 2009).

Figure 2:
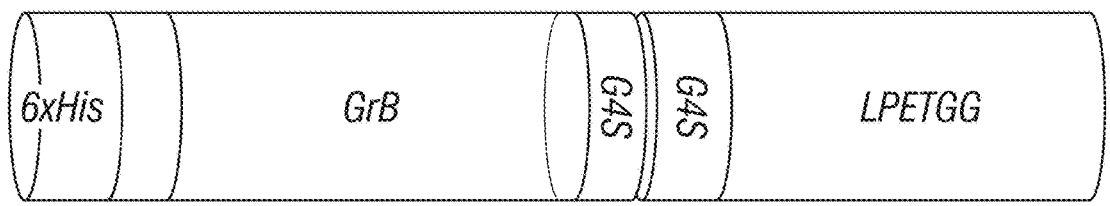
FIG. 2: Schematic of the GrB-$(G_4S)_2$-LPETGG (LPETGG is SEQ ID NO:79; $G_4S$ is SEQ ID NO:36) construct for use in sortase reaction.

To create a form of a serine protease, such as GrB, that can be snapped on to the N-terminal end of any recombinant protein that can be produced with a GGG sequence at its N-terminal end, a construct was achieved by modifying the structure of GrB to include two flexible spacers followed by the LPETGG (SEQ ID NO:79) sequence that allows the sortase reaction to form a peptide bond between the spacers at the C-terminal end of GrB and the N-terminal end of a tumor targeting protein. A GrB-$(G_4S)_2$-LPETGG (LPETGG is SEQ ID NO:79; $G_4S$ is SEQ ID NO:36) expressing vector was designed to have a 6×His tag on the N-terminal end for purification followed by an EK cut site that allows removal of the 6×His tag in the final product (FIG. 2). The vector was transfected into CHO-S cells, selected in zeocin under serum-free conditions for three weeks and then dilutionally cloned at 0.5 cell/well into 16 96-well plates. After single clones were grown and expanded, the expression levels of the recombinant GrB-$(G_4S)_2$-LPETGG (LPETGG is SEQ ID NO:79; $G_4S$ is SEQ ID NO:36) clones were assessed by Western blot analysis using anti-GrB antibody (FIG. 3). 17 positive clones were identified out of total 112 clones screened with Clone #31 producing the highest level of GrB-$(G_4S)_2$-LPETGG (LPETGG is SEQ ID NO:79; $G_4S$ is SEQ ID NO:36).

Example 2—Characterization of GrB-$(G_4S)_2$-LPETGG Construct

Figure 4A:
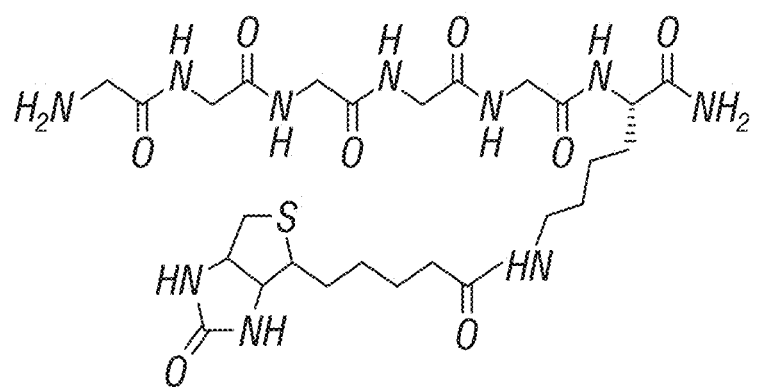
FIGS. 4A-B: Structure of acceptor peptides capable of reporting on kinetics of the sortase reaction.
Figure 4B:
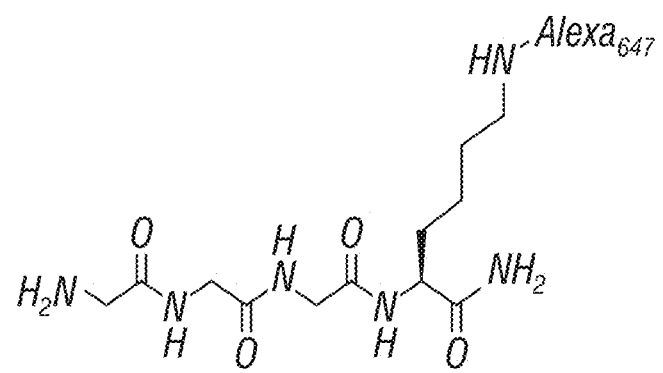

To facilitate a detailed study of the ability of the GrB-$(G_4S)_2$-LPETGG (LPETGG is SEQ ID NO:79; $G_4S$ is SEQ ID NO:36) and other warheads to form a peptide bond in the sortase reaction, two tagged peptides that have been reported to function well as acceptors in the sortase reaction (FIG. 4) were synthesized. The peptide shown in FIG. 4A (GGG-biotin) contains a biotin tag so that the product of the sortase reaction can be captured by streptavadin and its amount quantified by Western blot analysis. The peptide shown in FIG. 5B (GGG-fluorochrome) contains a fluorochrome that can be visualized directly. In order to allow the use of a Licor Odyssey instrument for precise quantification, the fluorochrome can be changed from Alexa$_{647}$ to Alexa$_{700}$ or Alexa$_{720}$ depending on solubility. These peptides, in combination with the 6×His tag on the N-terminal end of the GrB will allow the determination of the kinetics and completeness of the sortase reaction in detail.

Having established that the novel GrB warhead functions in the sortase reaction, a targeting moiety was attached in the form of yoked human chorionic gonadotropin (YCG) in which the α and β chains of the hCG hormone have been fused together to form a single protein as reported previously (Kanatani et al, 2011). The YCG was molecularly modified to add a triglycine sequence (GGG) followed by either 1 or 2 G$_4$S (SEQ ID NO:36) spacers to the N-terminal end of YCG so that it can function as an acceptor in the sortase reaction. These experiments established the principle that GrB warhead can be snapped onto another protein and will lead to further exploration of this reaction by attempting to snap GrB onto additional tumor targeting systems including those based on dendrimer folates.

Figure 7:
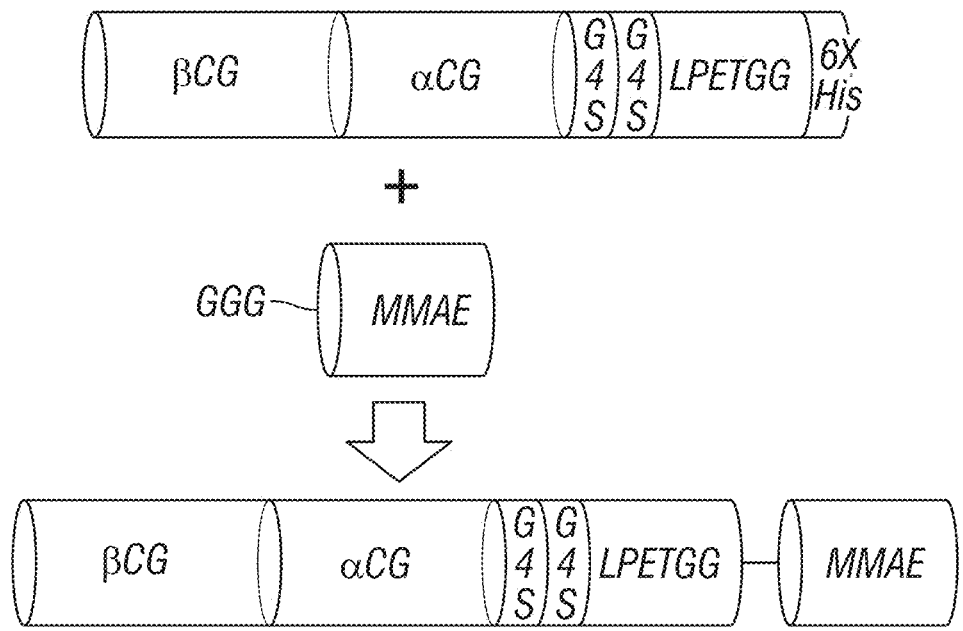
FIG. 7: Schematic of sortase-mediated reaction of YCG-$(G_4S)_2$-LPETGG (LPETGG is SEQ ID NO:79; $G_4S$ is SEQ ID NO:36) with GGG-vc-MMAE.

Example 3—Use of Sortase Reaction to Create a Molecule Consisting of YCG Linked to MMAE The results of Example 2 and studies using with GrB-YCG produced in Sf9 cells confirmed earlier studies suggesting that the LHR is selectively expressed on reproductive system tumors, and that it can be targeted effectively with YCG. Thus, there is a strong rationale for attempting to arm it with several different types of warheads. The extremely potent cytotoxic monomethylaurostatin E (MMAE) is being widely used to arm antibodies by linking it through a citrulline-valine protease-cleavable linker. It was hypothesized that the sortase reaction can be used to arm YCG by attaching a single molecule of valine-citrulline-MMAE (vc-MMAE) to the C-terminal end (FIG. 7).

Figure 8:
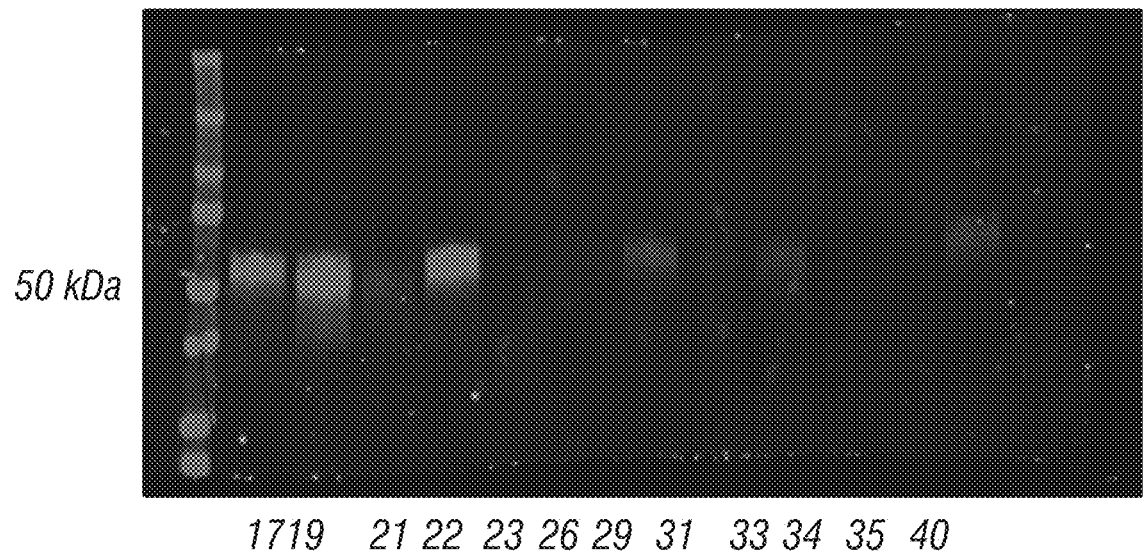
FIG. 8: Expression of YCG-$(G_4S)_2$-LPETGG (LPETGG is SEQ ID NO:79; $G_4S$ is SEQ ID NO:36) in individual single clones was determined by Western blot analysis using anti-hCG Ab at 1:2000 dilution.

The sortase reaction required an LPETGG (SEQ ID NO:79) sequence at the C-terminal end of the donor molecule and a GGG sequence at the N-terminal end of the acceptor molecule. The MMAE had a triglycine sequence and a citrulline-valine cleavable linker added [(glycine)$_3$-valine-citruline-MMAE, abbreviated (GGG-vc-MMAE) and sortase was produced as a recombinant protein in *E. coli*. Previous attempts to link YCG-LPETGG (SEQ ID NO:79) produced in Sf9 and CHO cells to chemically synthesized GGG-vc-MMAE in the presence of sortase were unable to obtain the final YCG-vc-MMAE product. It was suspected that access of the sortase to the LPETGG (SEQ ID NO:79) sequence at the C terminus of YCG may have been sterically hindered. Thus, a flexible spacer was added between the C-terminus and the LPETGG (SEQ ID NO:79) sequence. The molecule was re-engineered to put two (G$_4$S) (G$_4$S is SEQ ID NO:36) (spacers between YCG and LPETGG (SEQ ID NO:79). Simultaneously, based on the success in producing other proteins at higher yield in CHO cells, YCG-(G$_4$S)$_2$-LPETGG (LPETGG is SEQ ID NO:79; G$_4$S is SEQ ID NO:36) was cloned into the pSecTag vector and transfected in CHO-S cells for selection of YCG-(G$_4$S)$_2$-LPETGG (LPETGG is SEQ ID NO:79; G$_4$S is SEQ ID NO:36) expressing stable clones. Twenty YCG-(G$_4$S)$_2$-LPETGG (LPETGG is SEQ ID NO:79; G$_4$S is SEQ ID NO:36) expressing clones were identified out of 75 clones screened and Clone #22 was chosen for large-scale expression and subsequent experiments since it produces the highest level and cleanest YCG-(G$_4$S)$_2$-LPETGG (LPETGG is SEQ ID NO:79; G$_4$S is SEQ ID NO:36) (FIG. 8).

Figure 9:
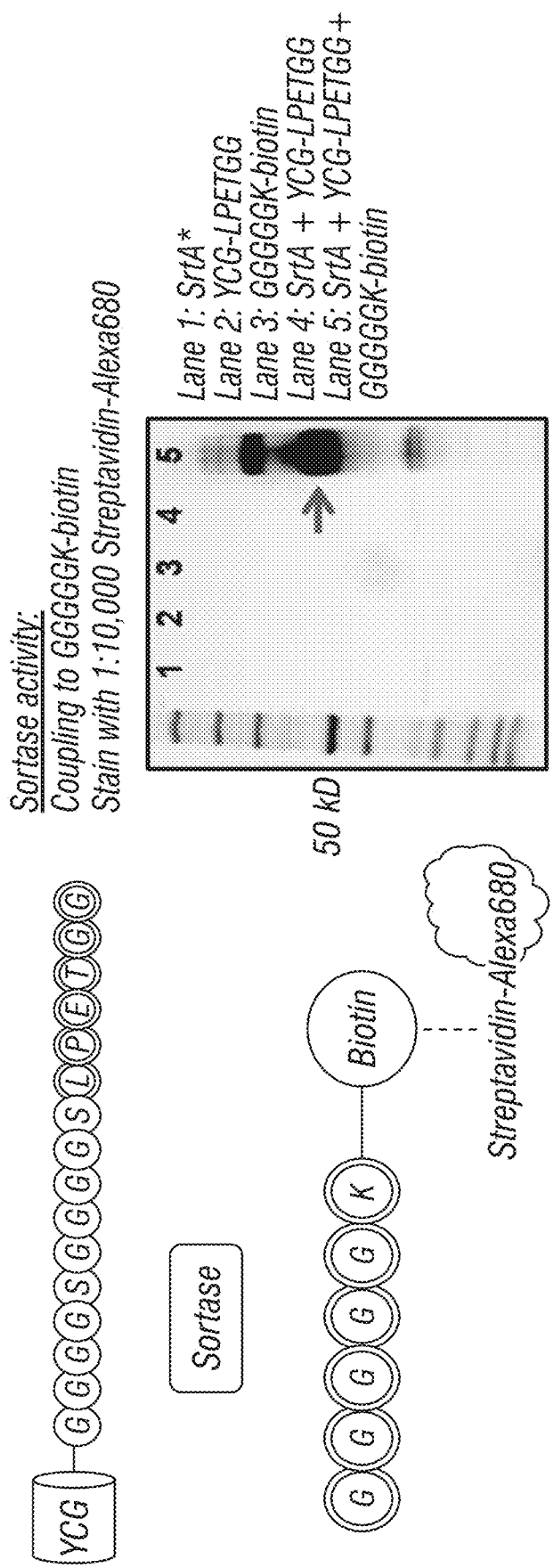
FIG. 9: Western blot analysis showing successful conjugation of YCG-LPETGG (SEQ ID NO:79) with G5K-biotin using the sortase reaction. Product increased with increasing concentrations of G5K-biotin.

Following IMAC purification, it was next determined whether YCG-(G$_4$S)$_2$-LPETGG (LPETGG is SEQ ID NO:79; G$_4$S is SEQ ID NO:36) would work in the sortase reaction by using G5K-biotin as the acceptor. As shown in FIG. 9, the reaction ran well and the amount of product increased with the concentration of G5K-biotin.

Figure 10:
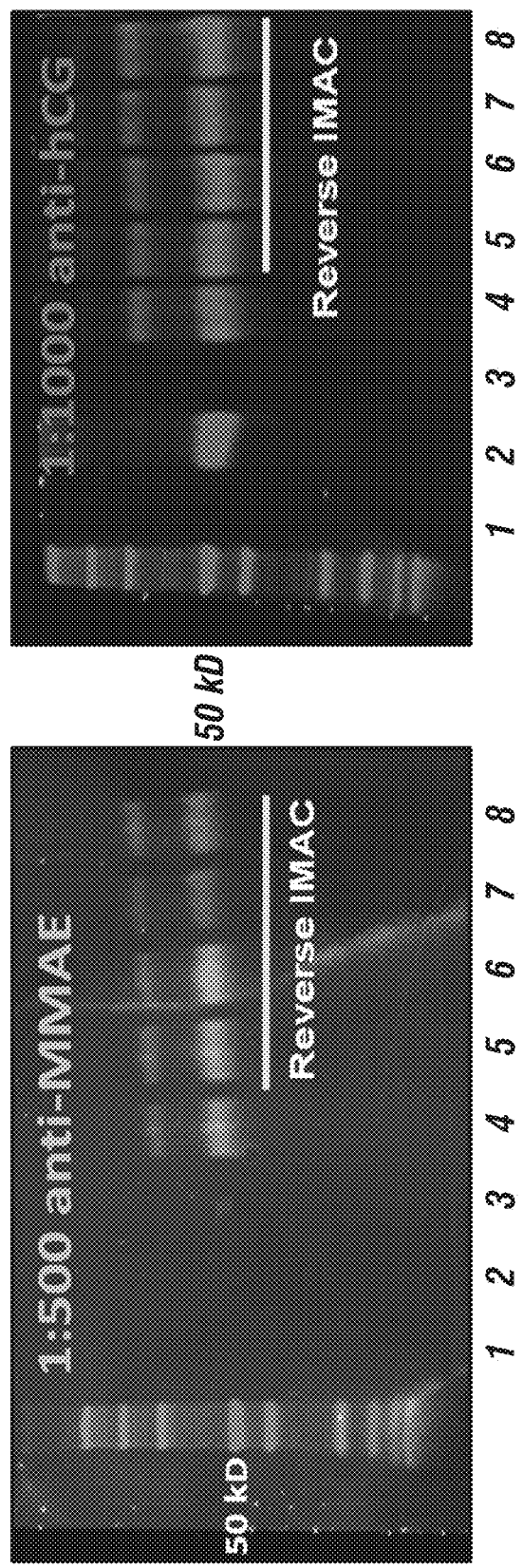
FIG. 10: Sortase-mediated ligation of YCG-(G$_4$S)$_2$-LPETGG (LPETGG is SEQ ID NO:79; G$_4$S is SEQ ID NO:36) with GGG-vc-MMAE and subsequent reverse IMAC purification. The components of reaction mixture were analyzed by Western blot analysis using anti-MMAE and anti-hCG antibody. Lane 1: SrtA; Lane 2: YCG-LPETGG (SEQ ID NO:79); Lane 3: GGG-vc-MMAE; Lane 4: SrtA+YCG-LPETGG+GGG-vc-MMAE (LPETGG is SEQ ID NO:79); Lane 5: Flow through of sortase reaction mixture; Lane 6: Wash; Lane 7: Elution; Lane 8: Dialyzed flow through+Wash.

The sortase reaction of YCG-(G$_4$S)$_2$-LPETGG (LPETGG is SEQ ID NO:79; G$_4$S is SEQ ID NO:36) with GGG-vc-MMAE was carried out at the ratio of 1:1:5 (sortase:donor:acceptor) at 37° C. for 6 h. As shown in FIG. 10, anti-MMAE antibody was able to detect a signal at a MW close to YCG-(G$_4$S)$_2$-LPETGG (LPETGG is SEQ ID NO:79; G$_4$S is SEQ ID NO:36) in the reaction mixture of sortase (lane 4) indicating that MMAE was successfully ligated to YCG-(G$_4$S)$_2$-LPETGG (LPETGG is SEQ ID NO:79; G$_4$S is SEQ ID NO:36) yielding the YCG-MMAE final product, which was also confirmed by blotting with anti-hCG antibody. The YCG-MMAE product is further purified using a combination of IMAC and dialysis, and its cytotoxicity is tested in vitro against isogenic LHR$^{WT}$ and LHR$^{KD}$ cells which express high levels of the LH receptor and a subline in which expression has been knocked down.

Figure 11A:
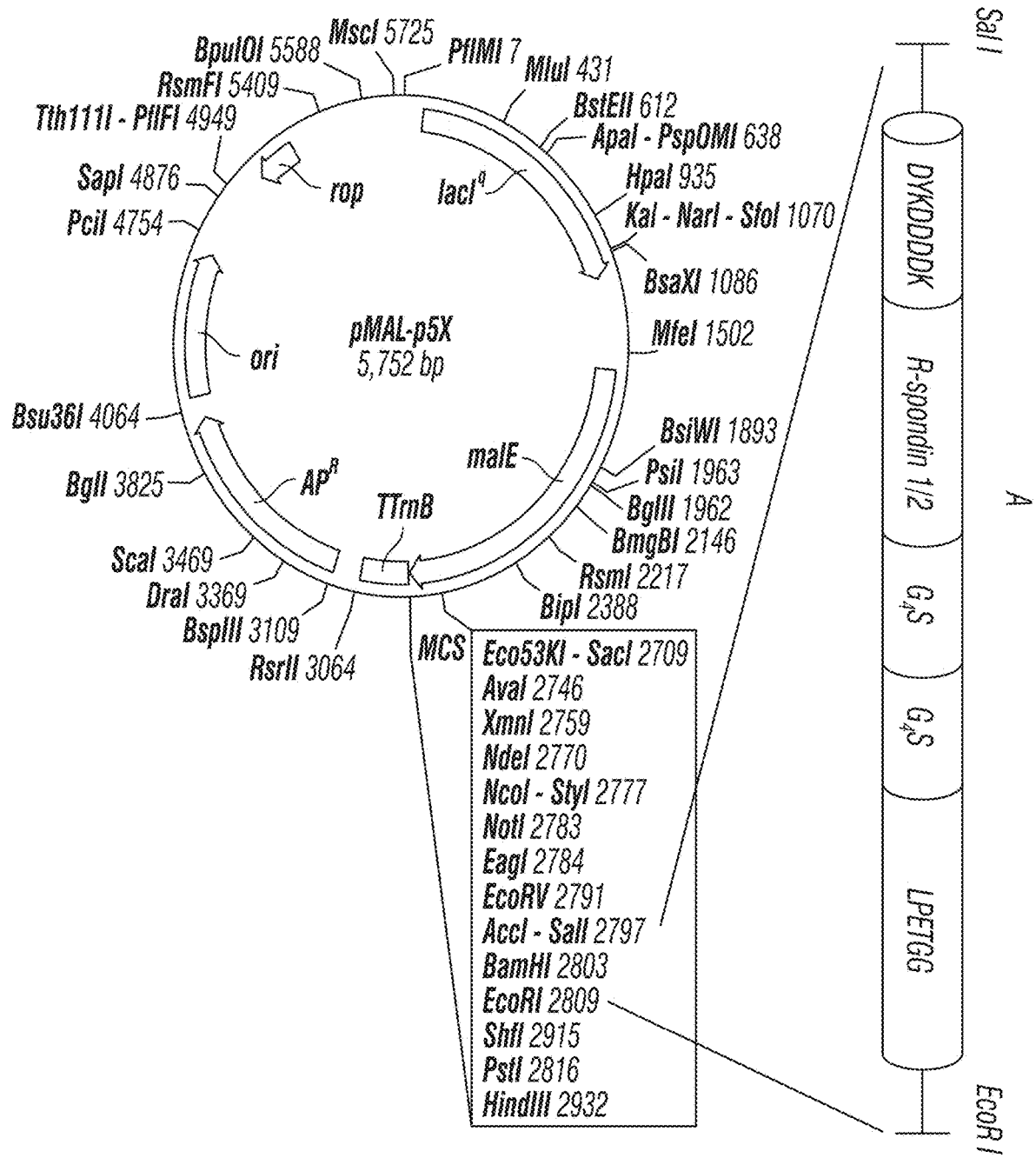
FIGS. 11A-C: Expression and purification of MBP-FLAG-RSPO1/2-(G$_4$S)$_2$-LPETGG (LPETGG is SEQ ID NO:79; G$_4$S is SEQ ID NO:36) in *E. coli*. (A) Schematic of the MBP-FLAG-RSPO1/2-(G$_4$S)$_2$-LPETGG (LPETGG is SEQ ID NO:79; G$_4$S is SEQ ID NO:36) construct for use in sortase reaction. (B) IMAC purification of MBP-FLAG-RSPO1-(G$_4$S)$_2$-LPETGG (LPETGG is SEQ ID NO:79; G$_4$S is SEQ ID NO:36) (see arrow denoting purified MBP-FLAG-RSPO1-(G$_4$S)$_2$-LPETGG) (LPETGG is SEQ ID NO:79; G$_4$S is SEQ ID NO:36). (C) IMAC purification of MBP-FLAG-RSPO2-(G$_4$S)$_2$-LPETGG (LPETGG is SEQ ID NO:79; G$_4$S is SEQ ID NO:36). Lane 1: whole cell lysate before induction; Lane 2: whole cell lysate after 4 h induction; Lane 3: clear lysate; Lane 4: flow through; Lane 5: wash 1; Lane 6: wash 2; Lane 7: elution 1; Lane 8: elution 2; Lane 9: elution 3.
Figure 11B:
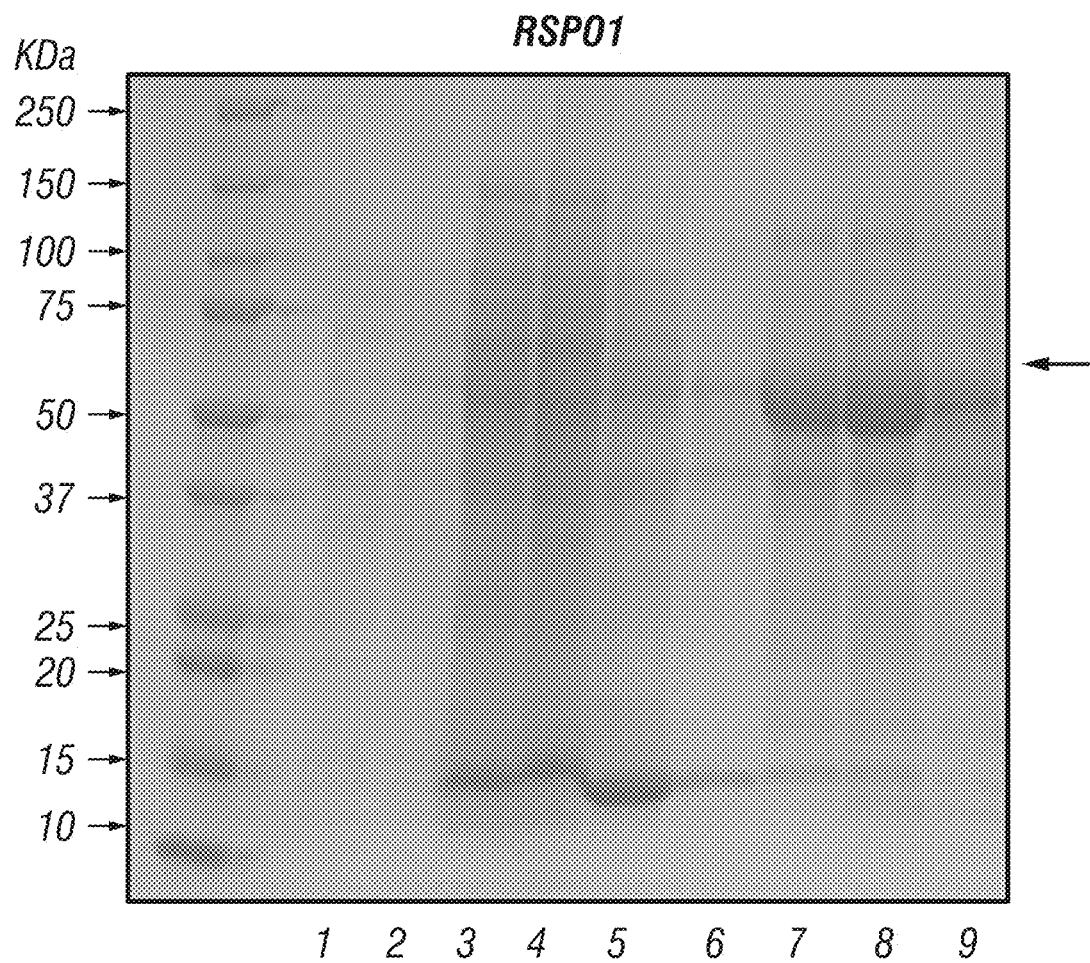
Figure 11C:
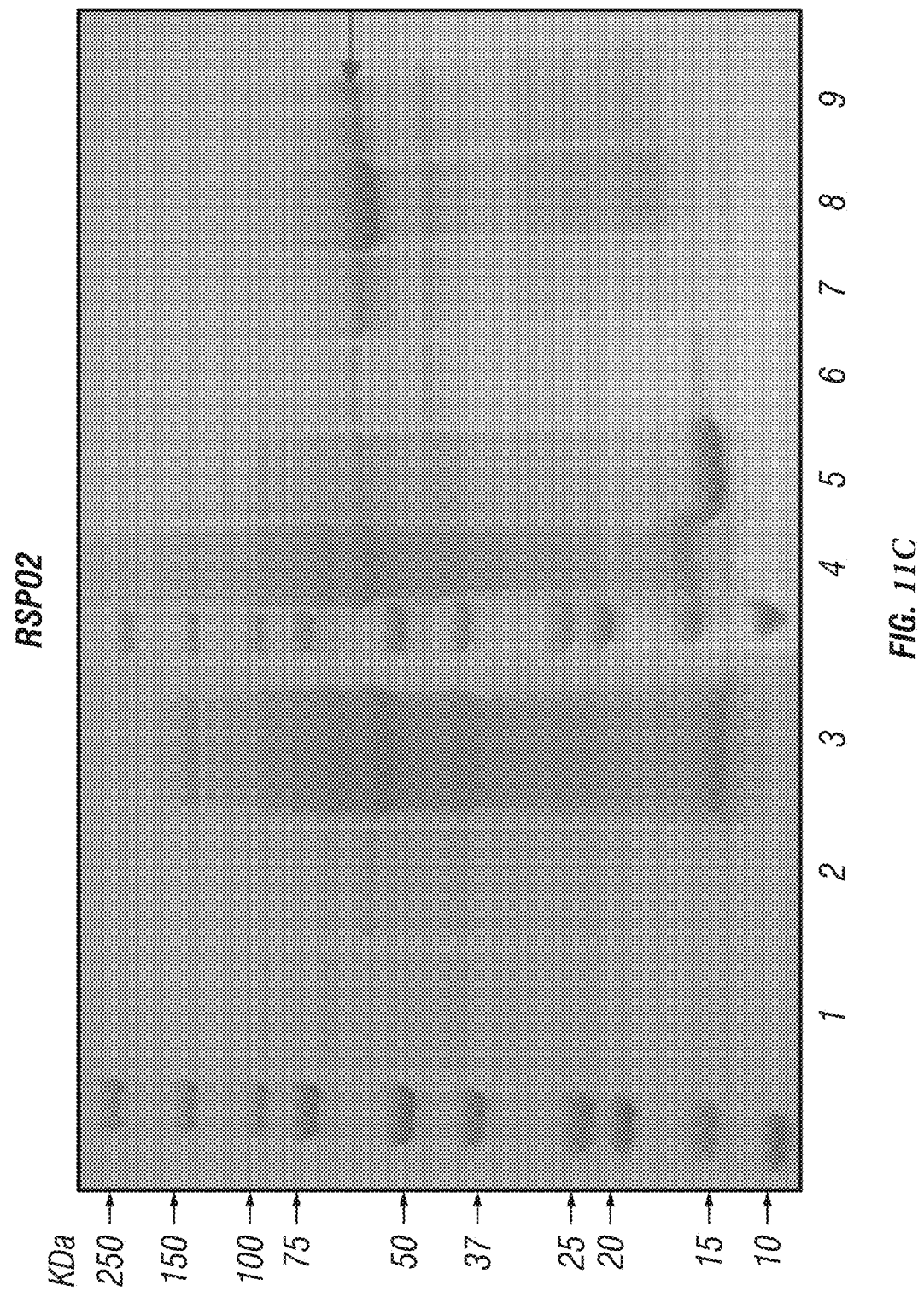

Example 4—Use of R-Spondins to Target Cytotoxin to LGR6-Expressing Tumor Stem Cells The pMAL-p5X vector was used to construct vectors that express either R-spondin 1 or R-spondin 2 connected through a pair of GGGGS (SEQ ID NO: 36) linkers to the LPETGG (SEQ ID NO:79) sequence (RSPO1-(G$_4$S)$_2$-LPETGG (LPETGG is SEQ ID NO:79; G$_4$S is SEQ ID NO:36) and RSPO2-(G$_4$S)$_2$-LPETGG) (LPETGG is SEQ ID NO:79; G$_4$S is SEQ ID NO:36). These were designed to have a MBP tag and EK cut site on the N-terminal end and 6×His tag on the C-terminal end for initial purification and final isolation of the end product (FIG. 11). The recombinant RSPO1-(G$_4$S)$_2$-LPETGG (LPETGG is SEQ ID NO:79; G$_4$S is SEQ ID NO:36) and RSPO2-(G$_4$S)$_2$-LPETGG (LPETGG is SEQ ID NO:79; G$_4$S is SEQ ID NO:36) proteins were effectively expressed as a soluble MBP fusion proteins in *E. coli*, and after purification by Ni-NTA metal-affinity chromatography (IMAC) they had the expected molecular masses of 64 kDa and 65 kDa, respectively.

Figure 12:
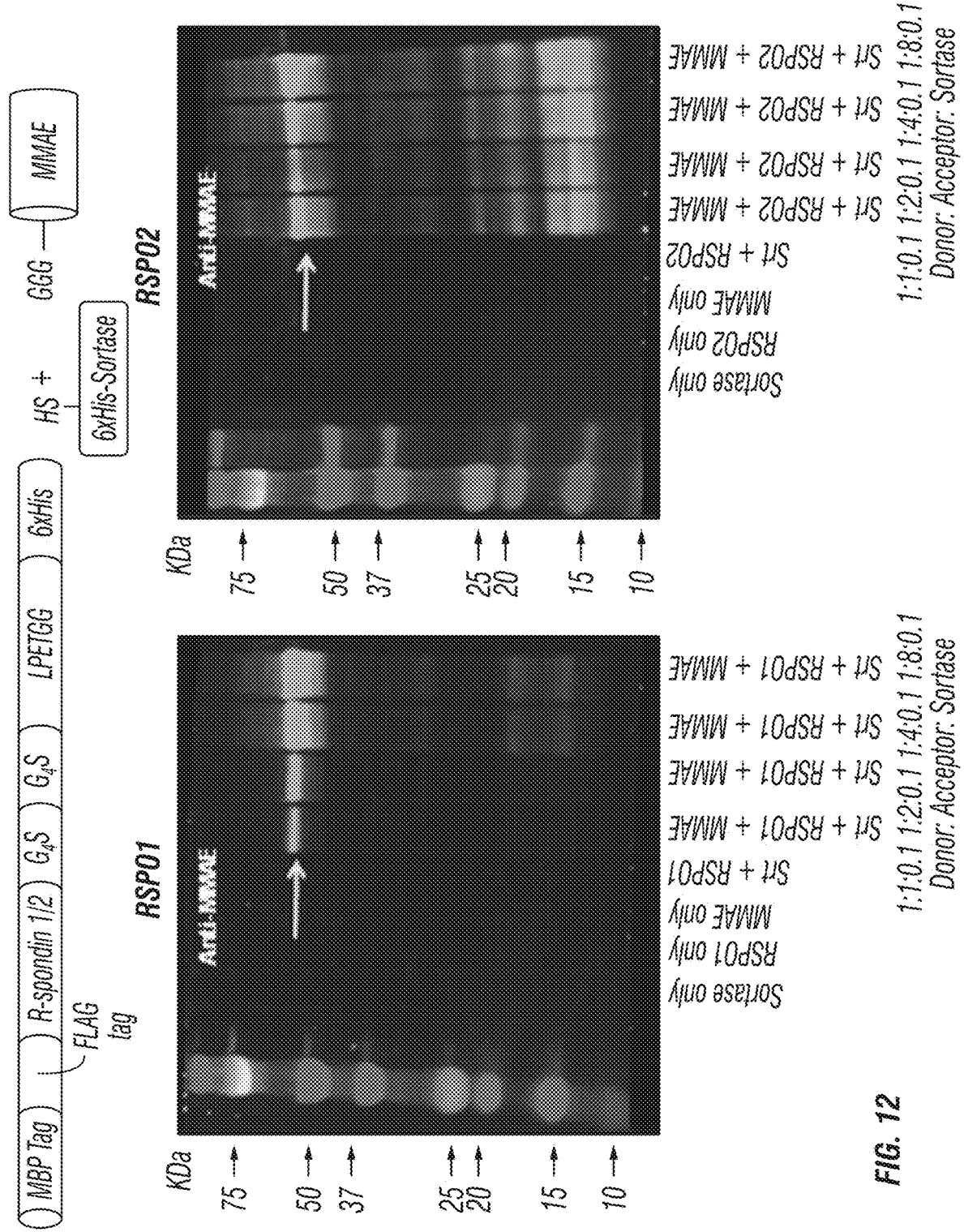
FIG. 12: Western blot analysis of sortase-mediated reaction of MBP-FLAG-RSPO1/2-(G$_4$S)$_2$-LPETGG (LPETGG is SEQ ID NO:79; G$_4$S is SEQ ID NO:36) with GGG-vc-MMAE using anti-MMAE antibody. Anti-MMAE antibody was able to detect a ligated product with MW close MBP-FLAG-RSPO1/2 indicating successful ligation of MMAE to the donor, and the yield increased with amount of acceptor MMAE input.
Figure 13:
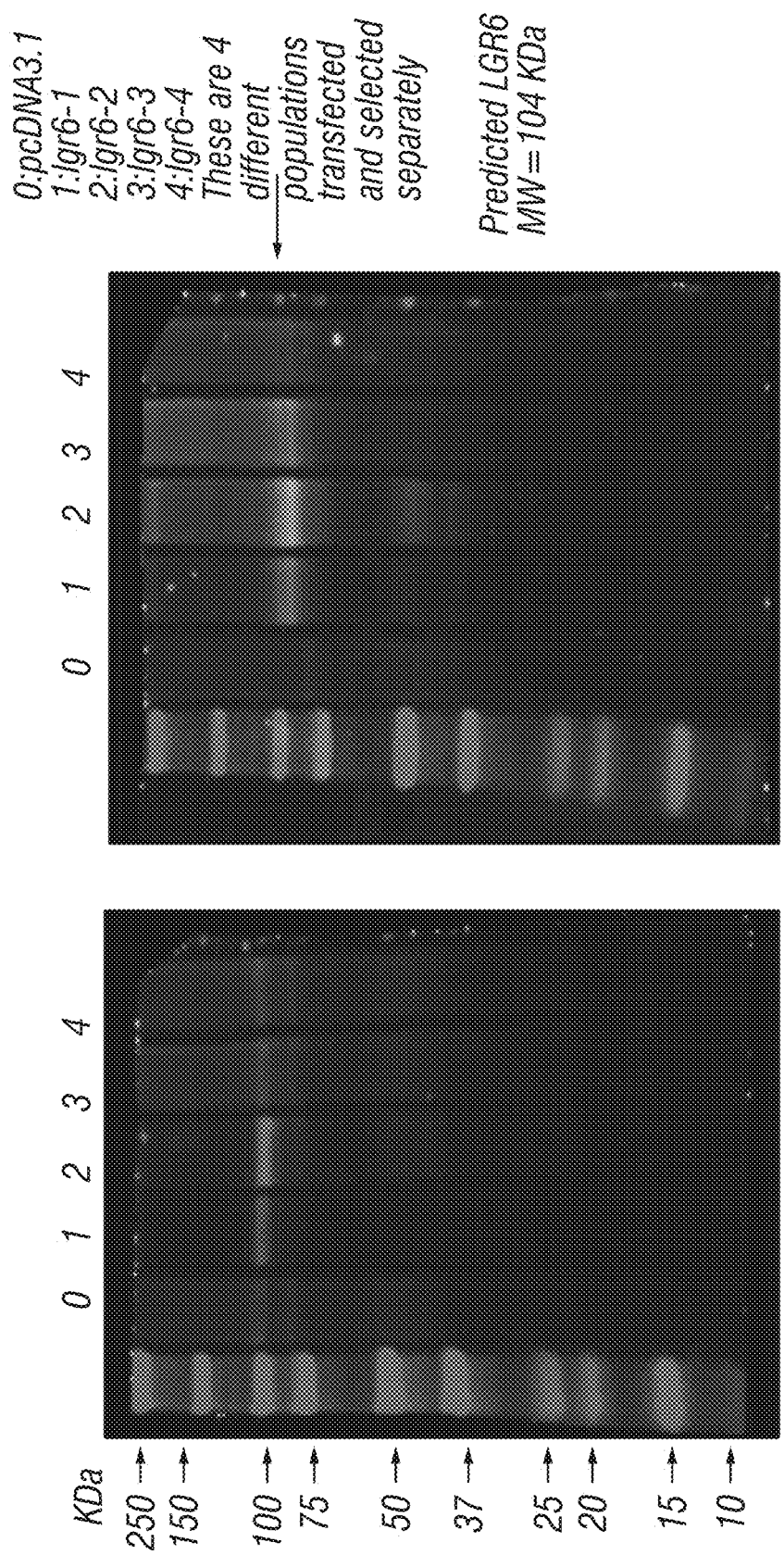
FIG. 13: LGR6 expression in 4 populations of HEK293T cells transfected with pcDNA3.1/LGR6-myc-his and selected with G418

Experiments were conducted to determine whether either RSPO1-(G$_4$S)$_2$-LPETGG (LPETGG is SEQ ID NO:79; G$_4$S is SEQ ID NO:36) or RSPO2-(G$_4$S)$_2$-LPETGG (LPETGG is SEQ ID NO:79; G$_4$S is SEQ ID NO:36) would serve as a donor in the sortase reaction. As shown in FIG. 12, using a small bioreactor, GGG-vc-MMAE was effectively coupled to both of these proteins in a concentration-dependent manner.

Figure 3:
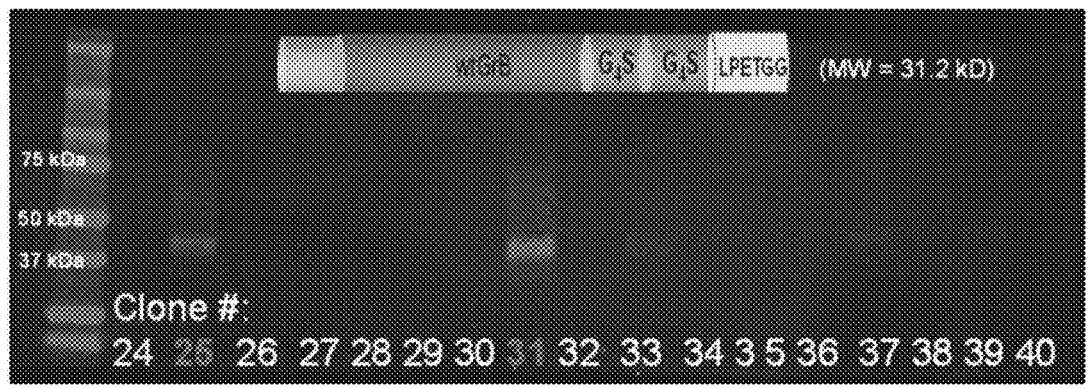
FIG. 3: Expression of GrB-$(G_4S)_2$-LPETGG (LPETGG is SEQ ID NO:79; $G_4S$ is SEQ ID NO:36) in individual single clones was determined by Western blot analysis using anti-GrB antibody at 1:1000 dilution.

Two approaches were used to establish isogenic test systems for assessment of LGR6-dependent selectivity of killing by RSPO-MMAE. LGR6 was overexpressed in cells that have a low level of this protein and both alleles of LGR6 were knocked down in an ovarian cancer cell line that expresses high levels of LGR6. Both HEK293 embryonal cells and Kuramochi ovarian cancer cells were transfected with a plasmid expressing the LGR6 cDNA and stable, high-expressing populations were isolated by Western blot screening. As shown in FIG. 3, a population of HEK293 cells that express a much higher level of LGR6 than the parental HEK293 cells was isolated.

Figure 14:
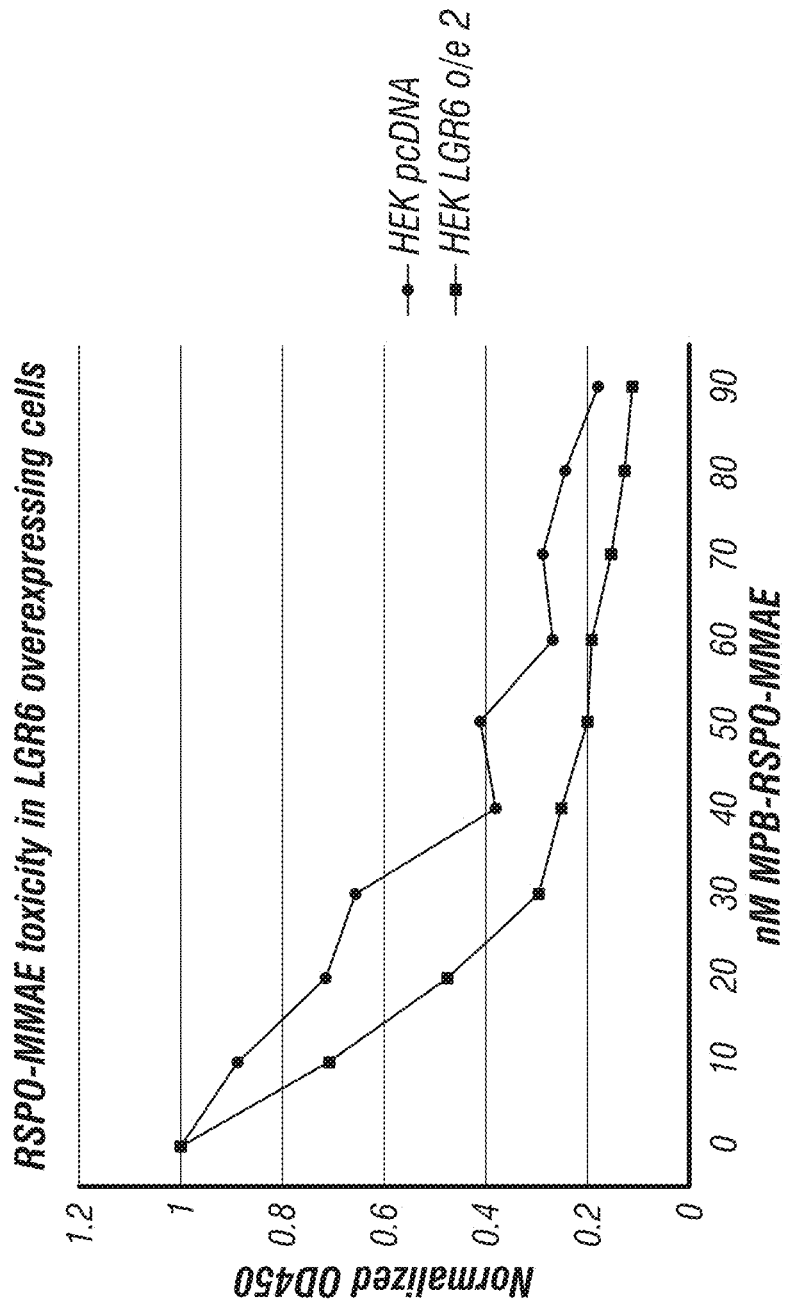
FIG. 14: MBP-RSPO1-MMAE concentration-survival curve. Cells were exposed to increasing concentrations of the drug for 10 days and the cell viability was determined by CCK-8 assay.

Empty vector-transfected HEK293 cells and population #2 of the LGR6 over-expressing HEK293 cells were used to test sensitivity to the "MBP-RSPO1-MMAE". As shown in FIG. 14, MBP-RSPO1-MMAE is 12-fold more potent at killing LGR6-overexpressing HEK-LGR6-2 cells than empty vector-transfected HEK-pcDNA cells (IC$_{50}$ 0.08 nM versus 0.95 nM). Thus, the sortase reaction can be used to develop targeted therapeutic agents.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,680,338
U.S. Pat. No. 5,141,648
U.S. Pat. No. 5,563,250
U.S. Pat. No. 5,856,456
U.S. Pat. No. 5,880,270
U.S. Pat. No. 6,232,287
U.S. Pat. No. 6,528,481
U.S. Pat. No. 7,452,964
U.S. Pat. No. 7,671,010
U.S. Pat. No. 7,781,565
U.S. Pat. No. 8,450,278
U.S. Pat. No. 8,507,445
U.S. Patent Appln. 2004005647
U.S. Patent Publn. 20050106660
U.S. Patent Appln. 20060234299
U.S. Patent Appln. 20060223114
U.S. Patent Publn. 20060058510
U.S. Patent Publn. 20060088908
U.S. Patent Publn. 20090253899
U.S. Patent Publn. 20100285564
U.S. Patent Publn. 20100317547
WO 97/19179
PCT Publication No. WO 1997/19179
PCT Publication No. WO2006/056464
Arai et al., 2004
Aulabaugh A, Ding W, Kapoor B, Tabei K, Alksne L, Dushin R, et al. Development of an HPLC assay for *Staphylococcus aureus* sortase: evidence for the formation of the kinetically competent acyl enzyme intermediate. *Anal Biochem.* 2007; 360:14-22.
Ausubel et al., 1998
Ausubel, 1996
Barclay et al. (eds.), The Leucocyte Antigen Facts Book, 1993, Academic Press.
Becker et al., *J. Neuroimmunol.*, 77:27-38, 1997.
Bedard et al., Beyond trastuzumab: overcoming resistance to targeted HER-2 therapy in breast cancer, *Curr. Cancer Drug Targets*, 9:148-162, 2009.
Bongartz et al., Improved biological activity of antisense oligonucleotides conjugated to a fusogenic peptide, *Nucleic Acids Res.*, 22:4681-4688, 1994.
Burkly et al.: TWEAKing tissue remodeling by a multifunctional cytokine: role of TWEAK/Fn14 pathway in health and disease. *Cytokine* 40:1-16 (2007).
Cao et al., Construction and characterization of novel, recombinant immunotoxins targeting the Her2/neu oncogene product: in vitro and in vivo studies, *Cancer Res.*, 69:8987-8995, 2009.
Cao et al., Single-chain antibody-based immunotoxins targeting Her2/neu: design optimization and impact of affinity on antitumor efficacy and off-target toxicity, *Mol. Cancer Ther.*, 11:143-153, 2012.
Cao Y, Marks J W, Liu Z, Cheung L H, Hittelman W N, Rosenblum M G. Design optimization and characterization of Her2/neu-targeted immunotoxins: comparative in vitro and in vivo efficacy studies. *Oncogene.* 2014; 33:429-39.
Cao Y, Mohamedali K A, Marks J W, Cheung L H, Hittelman W N, Rosenblum M G. Construction and characterization of novel, completely human serine protease therapeutics targeting Her2/neu. *Mol Cancer Ther.* 2013; 12:979-91.
Carter et al., Humanization of an anti-p185HER2 antibody for human cancer therapy, *Proc. Natl. Acad. Sci. U.S.A.*, 89:4285-4289, 1992.
Chowdhury and Lieberman, Death by a thousand cuts: granzyme pathways of programmed cell death, *Annu. Rev. Immunol.*, 26:389-420, 2008.
Cumber et al. (1992)
Fingl et al., In: *The Pharmacological Basis of Therapeutics*, 1:1, 1975.
Garrett and Arteaga, Resistance to HER2-directed antibodies and tyrosine kinase inhibitors:
mechanisms and clinical implications, *Cancer Biol. Ther.*, 11:793-800, 2011.
Goyal et al., 2000
Gully et al., Antineoplastic effects of an Aurora B kinase inhibitor in breast cancer, *Mol. Cancer,* 9:42, 2010.
Harvey et al., 2004
Hilgeroth et al., The impact of the induction of multidrug resistance transporters in therapies by used drugs: recent studies, *Mini. Rev. Med. Chem.*, 12:1127-1134, 2012.
Hurvitz and Kakkar, The potential for trastuzumab emtansine in human epidermal growth factor receptor 2 positive metastatic breast cancer: latest evidence and ongoing studies, *Ther. Adv. Med. Oncol.*, 4:235-245, 2012.
Jerome et al., Recombinant human insulin-like growth factor binding protein 3 inhibits growth of human epidermal growth factor receptor-2-overexpres sing breast tumors and potentiates herceptin activity in vivo, *Cancer Res.*, 66:7245-7252, 2006.
Kanatani I, Lin X, Yuan X, Manorek G, Shang X, Cheung L H, et al. Targeting granzyme B to tumor cells using a yoked human chorionic gonadotropin. *Cancer Chemother Pharmacol.* 2011; 68:979-90.
Kohl et al., 2003
Kovtun et al., Antibody-maytansinoid conjugates designed to bypass multidrug resistance, *Cancer Res.*, 70:2528-2537, 2010.
Kyte and Doolittle, *J. Mol. Biol.*, 157(1):105-132, 1982.
Liu et al., *Mol. Cancer Ther.*, 2:1341-1350, 2003.
Liu et al., Novel mechanism of lapatinib resistance in HER2-positive breast tumor cells: activation of AXL, *Cancer Res.*, 69:6871-6878, 2009.
Liu Y, Zhang W, Niu T, Cheung L H, Munshi A, Meyn R E, Jr., et al. Targeted apoptosis activation with GrB/ scFvMEL modulates melanoma growth, metastatic spread, chemosensitivity, and radiosensitivity. *Neoplasia.* 2006; 8:125-35.

Mohamedali K A, Cheung L H, Rosenblum M G. Characterization of a Human Fusion Protein Composed of Granzyme B and VEGF 121 for Targeting the Vasculatore of Solid Tumors. 2009.

Motyka et al., Mannose 6-phosphate/insulin-like growth factor II receptor is a death receptor for granzyme B during cytotoxic T cell-induced apoptosis, *Cell,* 103:491-500, 2000.

Murphy and Morris, Recent advances in novel targeted therapies for HER2-positive breast cancer, *Anticancer Drugs,* 23:765-776, 2012.

Nechushtan et al., 1997

Onda et al., *Cancer Res.,* 64:1419-1424, 2004.

Pack et al. (1992)

Plank et al., The influence of endosome-disruptive peptides on gene transfer using synthetic virus-like gene transfer systems, *J. Biol. Chem.,* 269:12918-12924, 1994.

Remington's Pharmaceutical Sciences, 18th Ed. Mack Printing Company, 1990.

Remington's Pharmaceutical Sciences, 18th Ed. Mack Printing Company, 1990, pp. 1289-1329.

Robinson et al., 1998.

Sambrook et al., 1989.

Skerra, 2001.

Szakacs et al., Targeting multidrug resistance in cancer, *Nat. Rev. Drug Discov.,* 5:219-234, 2006.

Thompson (ed.), 1994, The Cytokine Handbook, Academic Press, San Diego

Thorpe et al., *J. Natl. Cancer Inst.,* 79(5):1101-1112, 1987.

Ton-That H, Mazmanian S K, Faull K F, Schneewind O. Anchoring of surface proteins to the cell wall of *Staphylococcus aureus.* Sortase catalyzed in vitro transpeptidation reaction using LPXTG peptide and NH(2)-Gly(3) substrates. *J Biol Chem.* 2000; 275:9876-81.

Trapani and Sutton, Granzyme B: pro-apoptotic, antiviral and antitumor functions, *Curr. Opin. Immunol.,* 15:533-543, 2003.

Tsukiji S, Nagamune T. Sortase-mediated ligation: a gift from Gram-positive bacteria to protein engineering. Chembiochem. 2009; 10:787-98.

Turk et al., Characterization of a novel pH-sensitive peptide that enhances drug release from folate-targeted liposomes at endosomal pHs, *Biochim. Biophys. Acta,* 1559:56-68, 2002.

von Minckwitz et al., *Breast Cancer Res.,* 7:R616-626, 2005.

Wang et al., Different mechanisms for resistance to trastuzumab versus lapatinib in HER2-positive breast cancers—role of estrogen receptor and HER2 reactivation, *Breast Cancer Res.,* 13:R121, 2011.

Whitlow et al., 1993

Winkles J A: The TWEAK-Fn14 cytokine-receptor axis: discovery, biology and therapeutic targeting. *Nat Rev Drug Discov* 7:411-425 (2008).

Winthrop et al., *Clin. Cancer Res.,* 9:3845s-3853s, 2003.

Zhou et al.: Development and characterization of a potent immunoconjugate targeting the Fn14 receptor on solid tumor cells. *Mol Cancer Ther.* 10(7):1276-88, 2011.

Zhou H, Hittelman W N, Yagita H, Cheung L H, Martin S S, Winkles J A, et al. Antitumor activity of a humanized, bivalent immunotoxin targeting fn14-positive solid tumors. *Cancer Res.* 2013; 73:4439-50.

What is claimed is:

1. A cell-targeted cytotoxic construct comprising:
   (a) a targeting moiety that is an R-spondin targeting ligand that comprises two-tandem furin-like cysteine-rich (Fu-CRD) R-spondin domains, wherein the R-spondin targeting polypeptide ligand binds to a cell surface human LGR 4, LGR 5 and/or LGR 6 receptors;
   (b) a linking polypeptide that comprises a sortase recognition site, the linking polypeptide being positioned between the targeting moiety and the cytotoxic moiety; and
   (c) a cytotoxic moiety that comprises a toxin or chemotherapeutic, wherein the linking polypeptide is positioned between the targeting moiety and the cytotoxic moiety, and wherein the linking polypeptide comprises LPETG (SEQ ID NO: 66).

2. The cell-targeted construct of claim 1, wherein the linking polypeptide comprises LPETGG (SEQ ID NO: 79).

3. The cell-targeted construct of claim 1, wherein the construct further comprises at least one spacer positioned between the targeting moiety and the polypeptide linker.

4. The cell-targeted construct of claim 3, wherein the construct comprises two spacers.

5. The cell-targeted construct of claim 3, wherein the at least one spacer comprises the sequence G4S (GGGGS; SEQ ID NO: 36).

6. The cell-targeted construct of claim 1, wherein the targeting moiety is bound to the N-terminus of the linking polypeptide and the cytotoxic moiety is bound to the C-terminus of the linking polypeptide.

7. The cell-targeted construct of claim 1, wherein the targeting moiety is bound to the C-terminus of the linking polypeptide and the cytotoxic moiety is bound to the N-terminus of the linking polypeptide.

8. The cell-targeted construct of claim 1, wherein the R-spondin targeting ligand is RSPO1.

9. The cell-targeted construct of claim 1, wherein the R-spondin targeting ligand is RSPO2.

10. The cell-targeted construct of claim 1, wherein the cytotoxic moiety is a maytansinoid, an auristatin, an amanitin, a calicheamycin, a psymberin, a duocarmycin, an anthracyclin, a camptothecin, a doxorubicin, a taxol, a platin, an anthracycline, a podophyllotoxin, a combretastatin, or a pyrrolobenzodiazepine.

11. The cell-targeted construct of claim 10, wherein the cytotoxic drug is paclitaxel, docetaxel, etoposide, tenoposide, vincristine, vinblastine, colchicine, doxorubicin, daunorubicin, mithramycin, actinomycin, puromycin, epirubicin, cyclophosphamide, methotrexate, cytarabine, fluorouracil, cisplatin, streptozotocin, minomycin C, dactinomycin or actinomycin, bleomycin, mithramycin, anthramycin, duocarmycin, ifosfamide, mitoxantrone, daunomycin, carminomycin, animoterin, melphalan, esperamicin, lexitropsin, auristatin E, auristatin F, monomethyl auristatin E (MMAE), monomethyl auristatin F (MMAF), AEB, AEVB, AEFP, eleuthorobin, netropsin, maytansine, or DM1.

12. The cell-targeted construct of claim 9, wherein the cytotoxic moiety is an auristatin.

13. The cell-targeted construct of claim 11, wherein the auristatin is monomethylaurostatin E (MMAE).

14. The cell-targeted construct of claim 1, wherein the linking polypeptide further comprises a protease-cleavable sequence.

15. The cell-targeted construct of claim 14, wherein the protease-cleavable sequence is valine-citrulline.

* * * * *